(12) United States Patent
Prange et al.

(10) Patent No.: US 7,199,376 B2
(45) Date of Patent: Apr. 3, 2007

(54) METHOD AND APPARATUS FOR MONITORING A CONDITION IN CHLOROPHYLL CONTAINING MATTER

(75) Inventors: Robert Prange, Wolfville (CA); John Delong, Kentville (CA); Peter Harrison, Kentville (CA); Jerry Leyte, Kentville (CA); Scott Donald McLean, Hammonds Plains (CA); Jeffrey Garrett Edmund Scrutton, Halifax (CA); John Joseph Cullen, Barss Corners (CA)

(73) Assignee: Her Majesty the Queen in Right of Canada as represented by the Minister of Agriculture and Agri-Food Canada, Kentville, Nova Scotia (CA)

( * ) Notice: Subject to any disclaimer, the term of this patent is extended or adjusted under 35 U.S.C. 154(b) by 155 days.

(21) Appl. No.: 10/332,888

(22) PCT Filed: Jul. 16, 2001

(86) PCT No.: PCT/CA01/01039

§ 371 (c)(1),
(2), (4) Date: Jan. 24, 2003

(87) PCT Pub. No.: WO02/06795

PCT Pub. Date: Jan. 24, 2002

(65) Prior Publication Data

US 2003/0146394 A1      Aug. 7, 2003

Related U.S. Application Data

(60) Provisional application No. 60/218,141, filed on Jul. 14, 2000.

(30) Foreign Application Priority Data

Jul. 6, 2001    (CA)  .................................. 2352639

(51) Int. Cl.
G01N 21/64    (2006.01)

(52) U.S. Cl. ................. 250/458.1; 250/459.1

(58) Field of Classification Search ............ 250/458.1, 250/459.1, 461.1; 356/417, 318
See application file for complete search history.

(56) References Cited

U.S. PATENT DOCUMENTS

| | | | |
|---|---|---|---|
| 4,104,410 A | 8/1978 | Malecki | 426/399 |
| 4,768,390 A | 9/1988 | Baker et al. | 73/865.6 |
| 5,426,306 A | 6/1995 | Kolber et al. | 250/458.1 |
| 5,822,068 A | 10/1998 | Beaudry et al. | 356/417 |
| 6,563,122 B1 * | 5/2003 | Ludeker et al. | 250/458.1 |

FOREIGN PATENT DOCUMENTS

| | | |
|---|---|---|
| DE | 35 18 527 A | 11/1986 |
| WO | WO/2000/025114 | * 5/2000 |

OTHER PUBLICATIONS

Prange et al., "Chlorophyll Fluorescence Detects Low Oxygen Stress In 'Elstar' Apples," *Proceedings of the National Controlled Atmosphere Research Conference on Controlled Atmospheres for Storage and Transport of Perishable Agricultural Commodities* (1997) 2:57-64.

* cited by examiner

*Primary Examiner*—Otilia Gabor
(74) *Attorney, Agent, or Firm*—Clark & Elbing, LLP; Kristina Bieker-Brady

(57) ABSTRACT

A method of monitoring health in chlorophyll containing matter comprises exposing the matter to a light source to cause chlorophyll to fluoresce and emit a fluorescence signal. Any changes in a parameter indicative of changes in the intensity of the fluorescence signal are detected and compared with a predetermined threshold. A change which exceeds the predetermined threshold is interpreted as a transition of the level of stress in the chlorophyll containing matter. An apparatus for monitoring health in chlorophyll containing matter is also provided and comprises a light source for causing chlorophyll in the matter to fluoresce, a detector for detecting the intensity the fluorescent signal, means for measuring changes in a parameter indicative of changes in the intensity of the fluorescent signal and a detector to detect an increase in the change of the parameter above a predetermined threshold.

85 Claims, 51 Drawing Sheets

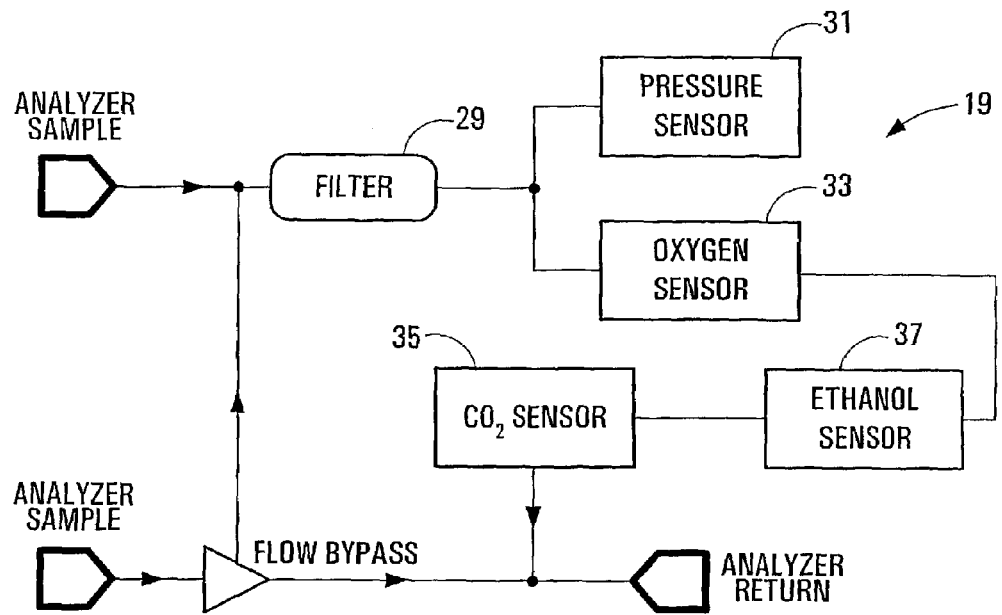
FIG. 22
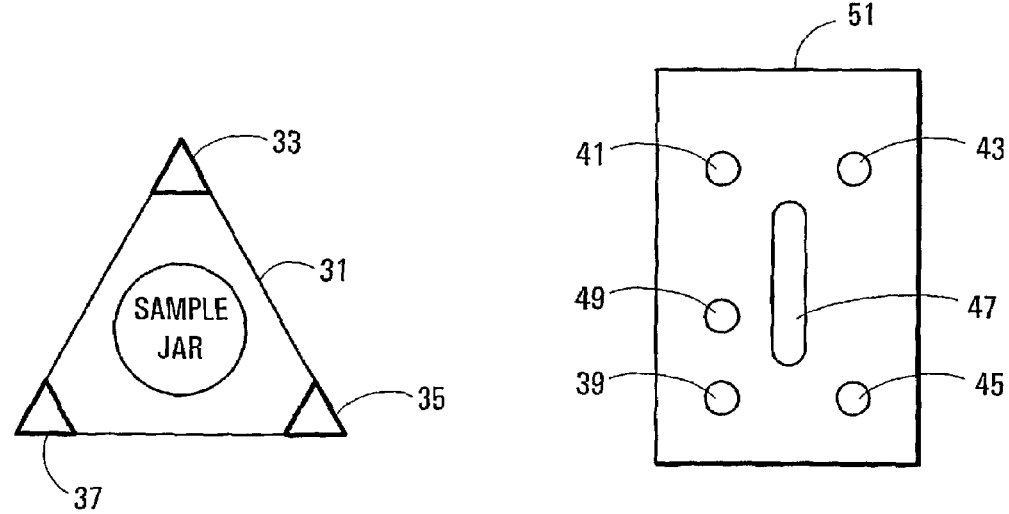
FIG. 23     FIG. 24

| | | | | | | | | | |
|---|---|---|---|---|---|---|---|---|---|
| 100 | 1.3 | 0 | 4718 | ... | 343 | 334 | ... | 2.797203 | 9.33 | 1229 | 0.72 |
| 101 | 1.3 | 0 | 4724 | 995.027 | 338 | 335 | 0.895522 | 3.00 | 1.573134 | 1221 | 0.723 |
| 102 | 1.29 | -0.1 | 4742 | 995.027 | 336 | 337 | -0.148588 | -0.50 | 1.394048 | 1236 | 0.728 |
| 103 | 1.24 | 0 | 4764 | 996.897 | 340 | 338 | 0.641342 | 2.17 | 1.19419 | 1213 | 0.719 |
| 104 | 1.2 | 0 | 4773 | 997.458 | 349 | 340 | 2.546523 | 8.67 | 1.356742 | 1231 | 0.716 |
| 105 | 1.15 | 0 | 4788 | 999.702 | 353 | 343 | 2.865469 | 9.83 | 1.599578 | 1230 | 0.713 |
| 106 | 1.15 | 0 | 4794 | 1001.759 | 355 | 345 | 2.848865 | 9.83 | 1.608189 | 1219 | 0.708 |
| 107 | 1.16 | 0 | 4811 | 1001.011 | 347 | 347 | 0.096154 | 0.33 | 1.474961 | 1210 | 0.713 |
| 108 | (1.13) | 0 | 4824 | 1001.572 | 358 | 350 | 2.188392 | 7.67 | 1.864457 | 1220 | 0.706 |
| 109 | 1.07 | 0 | 4851 | 1001.946 | 367 | 355 | 3.42884 | 12.17 | 2.32904 | 1221 | 0.699 |
| 110 | 1.03 | 0 | 4861 | 1003.255 | 364 | 357 | 1.865672 | 6.67 | 2.215565 | 1212 | 0.699 |
| 111 | 0.97 | 0 | 4873 | 1004.751 | 375 | 361 | 3.878116 | 14.00 | 2.38434 | 1203 | 0.688 |
| 112 | 0.95 | 0 | 4886 | 1005.125 | 365 | 363 | 0.643382 | 2.33 | 2.016759 | 1208 | 0.697 |
| 113 | 0.96 | 0 | 4900 | 1009.239 | 375 | 367 | 2.087114 | 7.67 | 2.348586 | 1226 | 0.694 |
| 114 | 0.97 | * | * | 1005.125 | 377 | 371 | 1.754386 | 6.50 | 2.276252 | * | 0.69 |
| 115 | 0.95 | * | * | * | 380 | 373 | 1.9678 | 7.33 | 2.032745 | * | 0.685 |
| 116 | 0.97 | * | * | * | 385 | 376 | 2.34825 | 8.83 | 2.113175 | * | 0.68 |
| 117 | 0.96 | * | * | * | 395 | 380 | 4.084321 | 15.50 | 2.147542 | * | 0.676 |
| 118 | 0.98 | * | * | * | 400 | 385 | 3.806228 | 14.67 | 2.674683 | * | 0.669 |
| 119 | 0.97 | * | * | * | 415 | 392 | 5.867347 | 23.00 | 3.304722 | * | 0.664 |
| 120 | 0.96 | * | * | * | 425 | 400 | 6.25 | 25.00 | 4.053991 | * | 0.661 |
| 121 | 0.97 | * | * | * | 430 | 408 | 5.306122 | 21.67 | 4.610378 | * | 0.657 |
| 122 | 0.97 | * | * | * | 435 | 417 | 4.4 | 18.33 | 4.952337 | * | 0.652 |
| 123 | 0.98 | * | * | * | 440 | 424 | 3.732809 | 15.83 | 4.893751 | * | 0.648 |
| 124 | 1 | * | * | * | 445 | 432 | 3.088803 | 13.33 | 4.77418 | * | 0.638 |
| | ... | ... | ... | ... | ... | ... | ... | ... | ... | ... | ... |
| 128 | 2.87 | 0 | 4153 | 1005.125 | 268 | 362 | -25.96685 | -94.00 | -12.45491 | 1154 | 0.767 |
| 129 | 2.9 | -0.1 | 4056 | 1004.003 | 272 | 334 | -18.56287 | -62.00 | -16.17086 | 1139 | 0.761 |
| 130 | 2.91 | 0 | 4049 | 1001.198 | 264 | 304 | -13.11026 | -39.83 | -18.8707 | 1166 | 0.773 |
| 131 | 2.91 | 0 | 4058 | 1001.011 | 269 | 274 | -1.884498 | -5.17 | -19.56617 | 1159 | 0.767 |

MORE SEVERE →

FIG. 25B (CONT.)

Pear Run # 3
Jar # 4   10/13/99

| Hours | O2 % | CO2 % | EtOH | Pressure | Fo | Fo Avg. | Change | % Chng. | Avg % Chng. | Fm | Fv/Fm |
|---|---|---|---|---|---|---|---|---|---|---|---|
| 0 | 20.89 | 0 | 4706 | 1001.011 | 247 | 247 | 0.00 | 0 | 0 | 1024 | 0.758 |
| 1 | 20.44 | 0 | 4752 | 1002.32 | 251 | 249 | 2.00 | 0.803213 | 0.401606 | 1025 | 0.755 |
| 2 | 20.08 | 0 | 4800 | 1003.068 | 249 | 249 | 0.00 | 0 | 0.267738 | 1020 | 0.755 |
| 3 | 20.08 | 0.1 | 4803 | 1003.442 | 252 | 250 | 2.25 | 0.900901 | 0.426028 | 1004 | 0.749 |
| 4 | 19.58 | 0.1 | 4813 | 1002.507 | 251 | 250 | 1.00 | 0.4 | 0.420823 | 1007 | 0.75 |
| 5 | 19.04 | 0.1 | 4798 | 1001.759 | 252 | 250 | 1.67 | 0.665779 | 0.461649 | 1012 | 0.75 |
| 6 | 18.43 | 0.1 | 4783 | 1000.45 | 254 | 252 | 2.50 | 0.994036 | 0.627321 | 1002 | 0.746 |
| 7 | 17.79 | 0.1 | 4760 | 999.702 | 252 | 252 | 0.33 | 0.13245 | 0.515528 | 997 | 0.747 |
| 8 | 17.17 | 0.1 | 4735 | 998.393 | 251 | 252 | -1.00 | -0.396825 | 0.449939 | 997 | 0.748 |
| 9 | 16.52 | 0.2 | 4711 | 998.767 | 258 | 253 | 5.00 | 1.976285 | 0.628621 | 973 | 0.734 |
| 10 | 15.12 | 0.2 | 4688 | 997.645 | 252 | 253 | -1.17 | -0.460829 | 0.485149 | 971 | 0.74 |
| .... | .... | .... | .... | .... | .... | .... | .... | .... | .... | .... | .... |
| 24 | 4.45 | 0.4 | 3902 | 980.254 | 241 | 250 | -9.33 | -3.728362 | -0.566821 | 885 | 0.727 |
| 25 | 3.82 | 0.4 | 3805 | 979.88 | 249 | 251 | -1.50 | -0.598802 | -0.544318 | 893 | 0.721 |
| 26 | 3.32 | 0.4 | 3693 | 978.384 | 264 | 252 | 12.17 | 4.831238 | -0.014867 | 900 | 0.706 |
| 27 | 2.87 | 0.4 | 3604 | 977.6931 | 261 | 253 | 7.67 | 3.026316 | 0.544452 | 891 | 0.707 |
| STRESS | | | | | | | | | | | |
| 28 | 2.46 | 0.4 | 3498 | 980.254 | 263 | 255 | 8.00 | 3.137255 | 1.056341 | 905 | 0.709 |
| 29 | 2.13 | 0.4 | 3396 | 980.6281 | 273 | 259 | 14.50 | 5.609284 | 2.046155 | 921 | 0.703 |
| 30 | 1.85 | 0.4 | 3302 | 981.7501 | 284 | 266 | 18.33 | 6.900878 | 3.817695 | 906 | 0.686 |
| 31 | 1.6 | 0.4 | 3206 | 982.498 | 293 | 273 | 20.00 | 7.326007 | 5.138496 | 905 | 0.676 |
| 32 | 1.44 | 0.4 | 3124 | 983.059 | 298 | 279 | 19.33 | 6.937799 | 5.48959 | 916 | 0.674 |
| 33 | 1.28 | 0.4 | 3055 | 985.303 | 309 | 287 | 22.33 | 7.790698 | 6.283654 | 934 | 0.669 |
| .... | .... | .... | .... | .... | .... | .... | .... | .... | .... | .... | .... |
| 50 | 0.65 | 0.3 | 2757 | 994.653 | 365 | 367 | -1.50 | -0.409277 | 1.793073 | 941 | 0.612 |
| 51 | 0.64 | 0.3 | 2747 | 995.027 | 379 | 369 | 9.83 | 2.663657 | 1.748673 | 937 | 0.595 |
| 52 | 0.64 | 0.4 | 2749 | 995.027 | 374 | 372 | 2.50 | 0.672948 | 1.586321 | 935 | 0.6 |
| 53 | 0.64 | 0.4 | 2755 | 993.718 | 381 | 373 | 7.83 | 2.099151 | 1.387069 | 929 | 0.589 |
| 54 | 0.63 | 0.4 | 2750 | 993.905 | 372 | 374 | -1.83 | -0.490415 | 1.044677 | 926 | 0.598 |
| 55 | 0.61 | 0.3 | 2752 | 995.027 | 377 | 375 | 2.33 | 0.622776 | 0.859807 | 947 | 0.601 |
| 56 | 0.63 | 0.3 | 2751 | 993.3441 | 385 | 378 | 7.00 | 1.851852 | 1.236661 | 933 | 0.587 |
| 57 | 0.63 | 0.3 | 2750 | 992.222 | 385 | 379 | 6.00 | 1.583113 | 1.056571 | 928 | 0.585 |

START →

FIG. 28B

| Banana Run #4 | | | | | | | | | | |
|---|---|---|---|---|---|---|---|---|---|---|
| Jar #5 10/29/99 | | | | | | | | | | |
| Hours | O2 % | CO2 % | EtOH | Pressure | Fo | Fo Avg. | Change | % Chng. | Avg % Chng. | Fm | Fv/Fm |
| 0 | 19.15 | .2 | 5225 | 984.742 | 190 | | | | 0 | 653 | 0.709 |
| 1 | 16.83 | 3.7 | 5168 | 979.506 | 176 | | | | -1.912568 | 634 | 0.722 |
| 2 | 14.58 | 5.3 | 5120 | 975.9531 | 178 | | | -3.825137 | -1.887791 | 616 | 0.711 |
| 3 | 12.42 | 6.9 | 5070 | 973.709 | 171 | 181.3333 | -3.333333 | -1.838235 | -2.499759 | 603 | 0.716 |
| 4 | 10.23 | 8.7 | 5003 | 970.343 | 174 | 178.75 | -7.75 | -4.335664 | -2.427254 | 584 | 0.702 |
| 5 | 8.09 | 9.9 | 4930 | 970.53 | 173 | 177.8 | -3.8 | -2.137233 | -2.399359 | 566 | 0.694 |
| 6 | 6.07 | 11 | 4829 | 969.0341 | 161 | 177 | -4 | -2.259887 | -3.480353 | 561 | 0.713 |
| 7 | 4 | 12 | 4712 | 968.286 | 170 | 172.1667 | -11.16667 | -6.485963 | -0.681597 | 557 | 0.694 |
| 8 | 2.22 | 12.7 | 4524 | 970.156 | 165 | 171.1667 | -1.166667 | -0.681597 | -2.95643 | 547 | 0.698 |
| 9 | 1.18 | 12.7 | 4295 | 978.197 | 169 | 169 | -4 | -2.366864 | -3.044535 | 535 | 0.684 |
| 10 | 0.61 | 12.6 | 3987 | 989.043 | 176 | 168.6667 | 0.333333 | 0.197628 | -2.288986 | 539 | 0.673 | START →
| 11 | 0.4 | 12.4 | 3722 | 996.897 | 202 | 169 | 7 | 4.142012 | -1.242445 | 545 | 0.629 |
| 12 | 0.32 | 12.4 | 3470 | 1004.377 | 239 | 173.8333 | 28.16667 | 16.20326 | 1.834746 | 540 | 0.557 |
| 13 | 0.29 | 12.3 | 3332 | 1007.93 | 272 | 186.8333 | 52.16667 | 27.9215 | 7.569323 | 555 | 0.509 |
| 14 | 0.29 | 12.3 | 3172 | 1011.109 | 300 | 203.8333 | 68.16667 | 33.44235 | 13.25665 | 565 | 0.469 |
| 15 | 0.25 | 12.3 | 3051 | 1011.109 | 309 | 226.3333 | 73.66667 | 32.54786 | 19.07577 | 571 | 0.458 |
| 16 | 0.13 | 12.3 | 2937 | 1012.231 | 323 | 249.6667 | 59.33333 | 23.76502 | 23.00367 | 572 | 0.435 |
| ... | ... | ... | ... | ... | ... | 274.1667 | 48.83333 | 17.81155 | 25.28192 | ... | ... |
| 35 | 16.46 | 0.1 | 5243 | 978.945 | 139 | 146.8333 | -7.833333 | -5.334847 | -20.66201 | 378 | 0.632 |
| 36 | 16.46 | 0.1 | 5238 | 978.571 | 134 | 142.6667 | -8.666667 | -6.074766 | -14.91434 | 375 | 0.642 |
| 37 | 16.51 | 0.1 | 5249 | 978.01 | 137 | 139 | -2 | -1.438849 | -10.02595 | 358 | 0.617 |
| 38 | 16.56 | 0.1 | 5253 | 978.7581 | 132 | 137.3333 | -5.333333 | -3.883495 | -6.787808 | 352 | 0.625 |
| 39 | 16.56 | 0.1 | 5254 | 979.6931 | 122 | 133.8333 | -11.83333 | -8.841843 | -5.966642 | 344 | 0.645 |
| 40 | 16.54 | 0.1 | 5246 | 980.6281 | 135 | 133.1667 | 1.833333 | 1.376721 | -4.032847 | 341 | 0.604 |
| 41 | 16.56 | 0.1 | 5248 | 980.254 | 126 | 131 | -5 | -3.816794 | -3.779838 | 330 | 0.618 |
| 42 | 16.52 | 0.2 | 5248 | 981.7501 | 124 | 129.3333 | -5.333333 | -4.123711 | -3.454662 | 324 | 0.617 |
| 43 | 16.52 | 0.1 | 5252 | 981.563 | 129 | 128 | 1 | 0.78125 | -3.084645 | 329 | 0.607 |
| 44 | 16.5 | 0.1 | 5252 | 982.872 | 120 | 126 | -6 | -4.761905 | -3.231047 | 315 | 0.619 |
| 45 | 16.49 | 0.2 | 5183 | 982.311 | 127 | 126.8333 | 0.166667 | 0.131406 | -1.735506 | 315 | 0.596 |
| 46 | 16.46 | 0.1 | 5096 | 983.246 | 121 | 124.5 | -3.5 | -2.811245 | -2.4335 | 309 | 0.608 |
| 47 | 16.44 | 0.1 | 5032 | 983.6201 | 118 | 123.1667 | -5.166667 | -4.194858 | -2.49651 | 297 | 0.602 |
| 48 | 16.43 | 0.1 | 5053 | 981.7501 | 119 | 122.3333 | -3.333333 | -2.724796 | -2.263358 | 295 | 0.596 |

STRESS (at hours 10-11)

FIG. 30B

TABLE 7

| SAMPLE TYPE | STANDARD FIRMNESS /lbs | STEPPED FIRMNESS /lbs |
|---|---|---|
| MARSHALL 1 | 14.66 | 14.56 |
| MARSHALL 2 | 13.48 | 15.20 |
| REDMAC | 11.39 | 14.26 |
| AVERAGE FIRMNESS | 13.18 | 14.67 |

FIG. 31

METHOD AND APPARATUS FOR MONITORING A CONDITION IN CHLOROPHYLL CONTAINING MATTER

CROSS REFERENCE TO RELATED APPLICATIONS

This application is the U.S. National Stage of International Application No. PCT/CA01/01039, filed Jul. 16, 2001, which was published in English, and which claims priority from U.S. Provisional Patent Application No. 60/218,141, filed Jul. 14, 2000 and Canadian Patent Application No. 2,352,639, filed Jul. 6, 2001.

FIELD OF THE INVENTION

The present invention relates to a method and apparatus for monitoring a condition in chlorophyll containing matter, for example fruits, vegetables and plants. The present invention also relates to a method and apparatus for controlling environmental conditions in which fruit, vegetables and plants can be stored over prolonged periods of time.

BACKGROUND OF THE INVENTION

A number of techniques presently exist for extending the time over which fruit and vegetables can be successfully stored without seriously affecting their quality between harvest and consumption. Such storage techniques are used to preserve various crops during transportation from one part of the world to another and to make seasonal commodities available to the consumer during other parts of the year.

Fresh fruits and vegetables are living tissues which continue to respire after harvesting. The process of respiration involves the use of oxygen in breaking down the food reserve contained within the fruit or vegetable, releasing energy and producing carbon dioxide. The rate of respiration, and therefore the rate of loss of the food reserve and deterioration of the commodity, is closely related to the respiration rate.

To prolong the storage periods of fruits and vegetables, their respiration rate is reduced by lowering the temperature and oxygen levels of the environment in which they are stored and by allowing the carbon dioxide level to increase. However, lowering the temperature too far will cause damage by freezing or chilling injury. Reducing the oxygen concentration too much will cause fermentation to occur within the fruit or vegetable which accelerates the ageing process and possibly causes other forms of damage associated with low oxygen levels. A storage environment containing excessive concentrations of $CO_2$ can also cause damage to fruit and vegetables. Damage resulting from incorrect environmental storage conditions reduces the quality and market potential of the produce.

The precise level of temperature, oxygen and carbon dioxide required to maximize storage life and to minimize storage disorders varies widely, depending on the type of produce, cultivars, growing conditions, maturity, harvest conditions, and post-harvest treatments. The ideal storage conditions can also depend upon where the particular product is grown and can vary from season to season. Recommended levels for different kinds of produce, which may be based, for example, on a crop's storage behaviour in previous years, are published by various national research bodies and extension advisors, and are considered to be the best compromise between extending life and minimizing storage disorders. The storage facilities are controlled to maintain the storage environment for a particular product at these recommended fixed levels. Because of the number of factors and their variability on which the ideal storage conditions depend, maintaining the product at the recommended levels may result in premature damage, in which case storage of the product has to be curtailed or loss is incurred. On the other hand, as the recommended levels often include a safety margin above a known damage threshold, the respiration rate of the produce is necessarily above the minimum the produce can tolerate, possibly leading to a shortened storage time.

A system for controlling the air composition in a room for storing vegetable products is disclosed in International Patent Application, Publication No. WO-A-96/18306. In one example, the system includes carbon dioxide and oxygen sensors for sensing the carbon dioxide and oxygen content, respectively, of a storage room in which vegetable products are stored. Under the control of a computer processor, the oxygen level in the storage room is reduced and the ratio between the carbon dioxide and oxygen levels is monitored. For normal respiration, the amount of carbon dioxide produced by the stored product is approximately equal to the oxygen consumed by the product so that the ratio of carbon dioxide to oxygen should be and remain equal to approximately 1, as the oxygen level is reduced. If the oxygen level is decreased too far, fermentation occurs where no oxygen is consumed but carbon dioxide is still produced, in which case the ratio of carbon dioxide to oxygen becomes greater than 1. The control system reduces the oxygen content until the latter condition is observed and thereafter increases the oxygen content slightly. If the ratio returns to 1, the oxygen content is again lowered until an increase in the ratio is detected. In another example, the occurrence of fermentation in the stored vegetable product is detected directly by measuring the presence of metabolites such as ethanol or lactate, formed by the fermentation process. In this case, the oxygen content is lowered until the presence of ethanol or lactate in the storage room is detected by a sensor and thereafter the oxygen content is slightly increased. If the increase is sufficient to bring the ethanol or lactate levels down to an unmeasurable level, the oxygen content is again gradually decreased until a measurable amount of lactate or ethanol is detected.

A method of testing the post-harvest quality of fruits and vegetables, such as firmness, texture, aroma and color using chlorophyll fluorescence is disclosed in U.S. Pat. No. 5,822, 068. The method involves irradiating a fruit or vegetable sample firstly with low level red light to stimulate minimal fluorescence within the chlorophyll and detecting the intensity of the minimal fluorescence, Fo, emitted by the sample, and shortly thereafter irradiating the sample with high level red light to stimulate maximum fluorescence within the chlorophyll and detecting the maximal fluorescence intensity, Fm, emitted by the sample. A relatively high value of either of these signals is taken as an indication of good quality, whereas lower values in the fluorescence signals are correlated to lower quality in the product.

Chlorophyll fluorescence techniques have also been used to detect damage and disorders in apples caused by low oxygen levels. One such study is described in: The Proceedings of the 7th Controlled Atmosphere Conference, Volume 2, pp 57–64 (1997), "Chlorophyll fluorescence detects low oxygen stress in "Elstar" apples", R. K Prange, S. P. Schouten and O. van Kooten, in which the minimal fluorescence intensity signal Of and the ratio (Fm−Fo)/Fm were measured for Elstar apples stored over a period of 20 days in an atmosphere containing 0.07% oxygen. The results show that Fo increased over the test period whereas (Fm−Fo)/Fm decreased. Independent quality measurements indicated that some of the low oxygen treated samples were firmer than the control samples, which were stored in air, and that the only disorder observed in the low oxygen treated apples was a gradual increase in an off-flavour during the 20 day treatment period.

SUMMARY OF THE INVENTION

According to one aspect of the present invention, there is provided a method of monitoring stress in chlorophyll containing matter, comprising the steps of exposing the matter to a light source to cause chlorophyll in the matter to fluoresce and emit a fluorescence signal, detecting any changes in a parameter indicative of changes in the intensity of the fluorescence signal, comparing any changes with a predetermined threshold and interpreting a change which exceeds the predetermined threshold as a transition of the level of stress in the matter.

The inventors have found that the onset of stress in chlorophyll containing produce is detectable by measuring chlorophyll fluorescence and is signified by an increase in the change of fluorescence intensity.

In one embodiment, the detected parameter is the intensity of the fluorescence signal.

According to another aspect of the present invention, there is provided an apparatus for monitoring stress in chlorophyll containing matter, comprising a light source for causing chlorophyll in the matter to fluoresce and emit a fluorescence signal, a detector for detecting the intensity of the fluorescence signal, means for measuring changes in a parameter indicative of changes in the intensity of the fluorescence signal, and means arranged to detect an increase in the change of the parameter above a predetermined threshold.

According to another aspect of the present invention, there is provided a method of controlling the intensity of a light source for stimulating a fluorescence signal from chlorophyll containing matter, comprising the steps of pulsing the light source and controlling the intensity of the light source by controlling the time period over which the light source is pulsed.

According to another aspect of the present invention, there is provided an apparatus for stimulating a fluorescence signal from chlorophyll containing matter comprising a light source, means for pulsing the intensity of the light source, and a controller for controlling the time period over which the light source is pulsed.

According to another aspect of the present invention, there is provided an apparatus for detecting a fluorescence signal emitted from chlorophyll-containing matter comprising a detector for detecting the intensity of the fluorescence signal, means for recording the intensity of each of a plurality of fluorescence signals over time, means for comparing a parameter responsive to the intensity of the fluorescence signal with a predetermined value and means for indicating when a measured intensity exceeds the predetermined value.

According to another aspect of the present invention, there is provided a method of determining an optimum value of an environmental parameter of an environment for storing chlorophyll-containing fruit or vegetables, comprising the steps of: (a) exposing the fruit or vegetable to a light source to cause chlorophyll in the fruit or vegetable to fluoresce and emit a fluorescence signal (b) detecting the intensity of the fluorescence signal, (c) measuring the value of the changing environmental parameter, (d) progressively reducing the oxygen level, (e) measuring the change in the intensity of the fluorescence signal as the environmental parameter is changed, (f) detecting an increase in the change of the intensity of the fluorescence signal, and (g) determining the optimal value of the environmental parameter from the detected increase in the change of the fluorescence intensity.

According to another aspect of the present invention there is provided an apparatus for determining an optimum value of an environmental parameter of an environment for storing chlorophyll containing fruit or vegetables comprising: a light source to cause chlorophyll in said fruit or vegetable to fluoresce and emit a fluorescence signal, a detector for detecting the intensity of said fluorescence signal, a sensor for measuring the value of an environmental parameter, control means arranged to progressively change said environmental parameter, means for measuring changes in the fluorescence intensity as the value of said environmental parameter is progressively changed, and means arranged to detect an increase in the change of the fluorescence intensity above a predetermined threshold.

According to the present invention there is further provided a system and method for controlling an environmental parameter in a storage room for storing chlorophyll containing fruit and vegetables in response to changes in the intensity of chlorophyll fluorescence emitted by the produce.

BRIEF DESCRIPTION OF THE DRAWINGS

Examples of embodiments of the present invention will now be described with reference to the drawings in which:

FIG. 22 shows a diagram of the gas analyzer system of FIG. 20;

FIG. 23 shows a top view of an embodiment of a fluorometer used in the system of FIG. 19;

FIG. 24 shows an arrangement of light sources and light sensors of the fluorometer shown in FIG. 23;

FIG. 28B shows a table of part of the numerical data plotted in the graph FIG. 28A;

FIG. 30B shows a table of part of the numerical data plotted in the graph of FIG. 30A;

FIG. 31 shows a table of the results of measured firmness in apple samples stored over a period of 4 months under two different conditions.

DETAILED DESCRIPTION OF PREFERRED EMBODIMENTS

Figure 1:
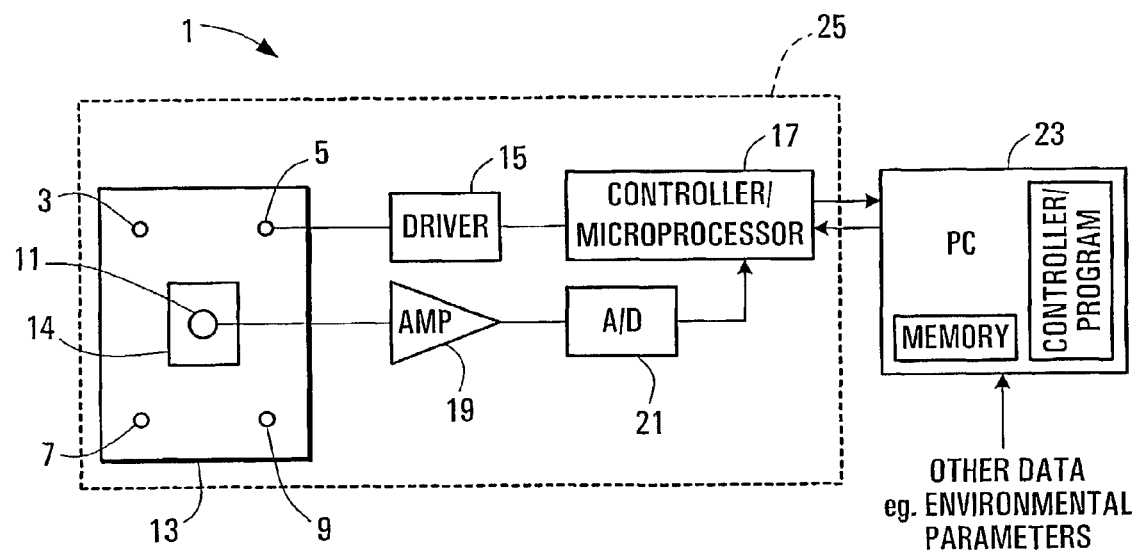
FIG. 1 shows a block diagram of an apparatus for measuring the fluorescence response of chlorophyll containing matter in accordance with an embodiment of the present invention.

FIG. 1 shows an embodiment of an apparatus for detecting stress in chlorophyll containing produce according to an embodiment of the present invention. The apparatus, generally shown at 1 comprises a rectangular array of four light sources, 3, 5, 7, 9 and a light sensor 11 positioned within a central region of the rectangular array of light sources, all mounted on a support panel 13. In this embodiment, the light sources 3, 5, 7, 9 each comprises a light emitting diode (LED) although in other embodiments, any other suitable light source may be used. The sensor comprises a photodiode, although in other embodiments, any other suitable light sensor may be used. An optical filter 14 is arranged in front of the sensor 13 to prevent the sensor receiving light from the light sources. The apparatus further includes a driver 15 for driving the light sources and a controller 17 which may for example be a microprocessor, for controlling the light sources. The apparatus also includes an amplifier 19 for amplifying signals from the light sensor 11 and an analog to digital converter (ADC) 21 for converting the amplified analog signal from the amplifier 19 into a digital signal. The output of the A/D converter is connected to an input of the controller 17. A computer 23 interfaces with the controller 17 to control the operation of the light sources and to record data relating to the signals detected by the light sensor 11. The components of the apparatus enclosed within the dashed line 25 may optionally be housed within a single enclosure or casing for convenience.

Figure 2:
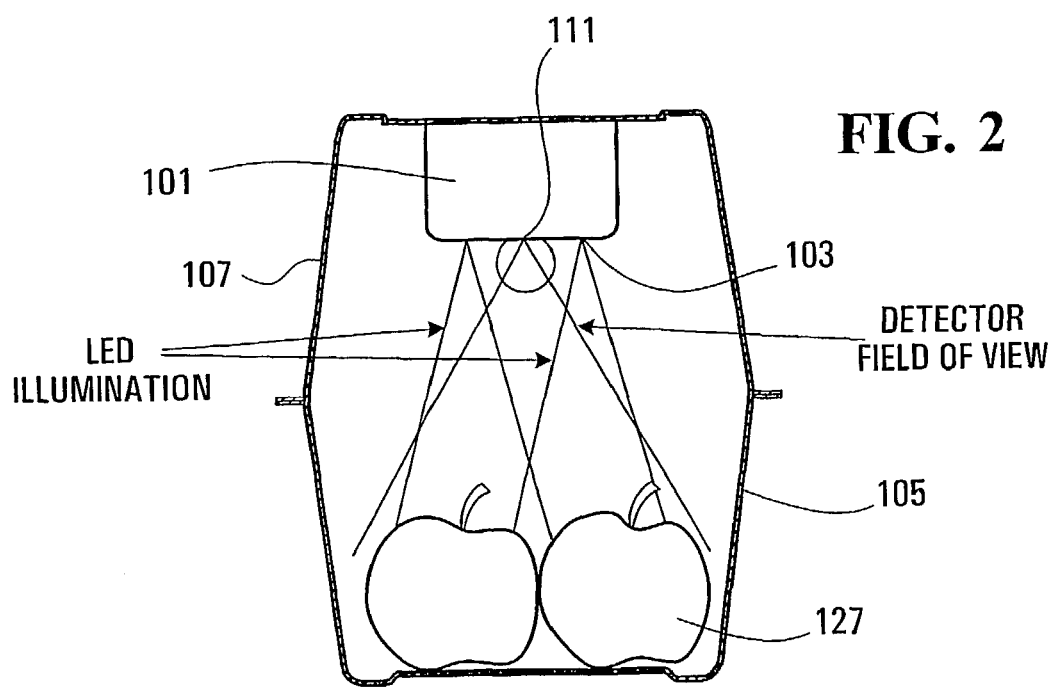
FIG. 2 shows a cross-sectional view of an apparatus for measuring the fluorescence response of chlorophyll containing matter in accordance with an embodiment of the present invention.

FIG. 2 shows an example of an arrangement in which the apparatus is used to monitor stress in chlorophyll containing produce.

Referring to FIG. 2, one or more produce samples 103 are placed in a container 105 having a removable lid 107. A stress sensing device 101 is positioned within the container 105 such that the light sources 103 and the light sensor 111 are directed at the sample(s) 127. The stress sensing device 101 is positioned a fixed distance from the produce sample (s) 127 and may conveniently be mounted to the inside of the lid 107 of the container.

In the arrangement shown in FIG. 2, the distance between the stress sensing device 101 and the produce sample 127 is such that the light sources combine to irradiate a relatively high proportion of the accessible upper surface area of the sample and the sensor can receive fluorescence signals emitted from a relatively high proportion of the sample area.

An example of a method of monitoring stress in chlorophyll containing matter will now be described with reference to FIGS. 1 and 2.

The computer 23 specifies a predetermined light source intensity level to the controller 17 which causes the driver 15 to energize the light sources 3, 5, 7 and 9 at the specified intensity level. The light sources may be energized such that the light intensity at the sample surface is generally at an intensity in the range of about 0.01 to 10 $\mu mol \cdot m^{-2} \cdot s^{-1}$, or more. A fluorescence signal emitted by the chlorophyll in response to light from the light sources is detected by the sensor 11 and converted into an electrical signal which is amplified by the amplifier 19, converted to a digital signal by the A/D converter, and the resulting digital signal is read by the controller 17 and passed to the computer 23 for processing and storage.

In one embodiment, the computer calculates any change in the intensity of the fluorescence signal by comparing a value of intensity measured at one time with the value of the intensity at another time. The computer may be arranged to provide an indication to a user of the measured fluorescence intensity so that the user can compare the current value of intensity with previous values and thereby monitor any change. Such an indication may be provided visually, for example on visual display, or by any other suitable means. The computer 23 may also be arranged to compare any change with a predetermined threshold value and provide an indication of when a change in the intensity of the fluorescence signal exceeds the predetermined threshold.

In a preferred embodiment, the controller 17 controls the A/D converter 21 to process signals from the sensor both when the light source is on and when the light source is off. The measured intensities resulting from both conditions are then read by the microprocessor and passed to the computer 23. The computer 23 subtracts the intensity measured when the light sources are off from the intensity measured when the light sources are on to provide an intensity value which is solely attributable to fluorescence stimulated by the light source without any contribution from other possible background sources.

In one embodiment of a method of monitoring stress in chlorophyll containing produce, the fluorescence intensity is measured for a plurality of different amounts of light or light levels. This methodology may be implemented under the control of the computer which may be arranged to instruct the controller to energize the light source at a first level of integrated photon flux and shortly thereafter to energize the light sources with a second, different level of integrated photon flux. The computer receives the fluorescence intensity values measured at each light level and may record them in memory for further processing. In this way, the intensity of the fluorescence signal emitted from the chlorophyll may be measured for many different light source intensity levels.

The inventors have discovered that the fluorescence intensity emitted by chlorophyll as a function of the light source can be generally described mathematically, for example by a second order polynomial. Advantageously, measuring the fluorescence intensity at a number of different light source levels allows the values of the parameters describing the polynomial to be calculated, one of which is the value $F_\alpha$ which is the theoretical value of the fluorescence intensity when the light source intensity is zero. The inventors have discovered that $F_\alpha$ can be measured with a high degree of accuracy and is extremely sensitive to physiological changes in the chlorophyll due to stress. The parameters A and B which describe the second and first order terms of the polynomial, respectively, have also been discovered to be useful indicators of the physiological state of the chlorophyll containing produce.

Figure 3:
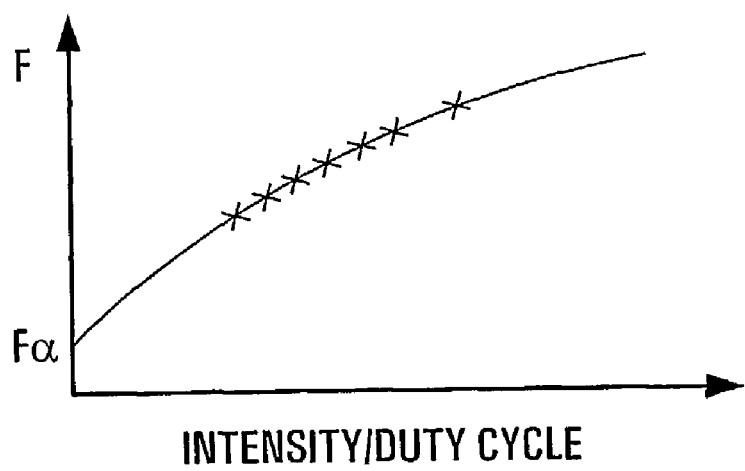
FIG. 3 shows an example of a graph of fluorescence intensity as a function of integral photon flux of a chlorophyll fluorescence stimulating light source.

An example of the dependence of fluorescence intensity on the light source intensity level is shown in FIG. 3. Data points are represented by crosses and the polynomial regression fitted to the data points is shown by the continuous line. The value of $F_\alpha$ corresponds to the value of fluorescence intensity at the intercept of the extrapolated curve at the Y axis (i.e. at light source level=zero).

A particularly advantageous method of varying the intensity of the light source to permit data to be taken at many different light source levels will now be described with reference to FIGS. 4A, 4B and 4C.

Embodiments of the present invention vary the photon flux to which the chlorophyll containing matter is exposed by on-off pulsing the light source and varying various parameters which define the pulses. In one method of generating a given light level, a train or series of pulses is generated each having a defined pulse width and a predefined time between pulses. In this case, the effective light level is the integrated photon flux over the train sequence. To generate a different effective light level, a second train of pulses is generated having the same pulse width and number of pulses but a different time interval between pulses. An example of this method is shown in FIG. 4A. FIG. 4A shows two pulse trains both having the same number of pulses 405 (in this case four although any suitable train of pulse could be used in each train e.g. between 1 and 1000 or more) and with the pulses in both pulse trains having the same pulse width, $t_1$. However, the time $t_2$ between pulses is longer for the first pulse train 401 than the second pulse train 403. Therefore, the integrated photon flux for the second pulse train 403 is greater than the integrated photon flux of the first pulse train 401.

Figure 4A:
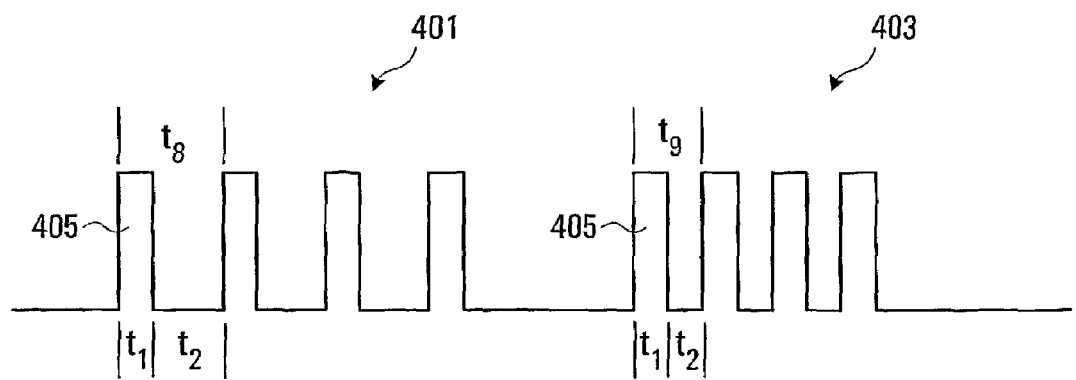
FIGS. 4A, 4B and 4C show examples of light source pulsing methods in accordance with embodiment of the present invention.
Figure 4B:
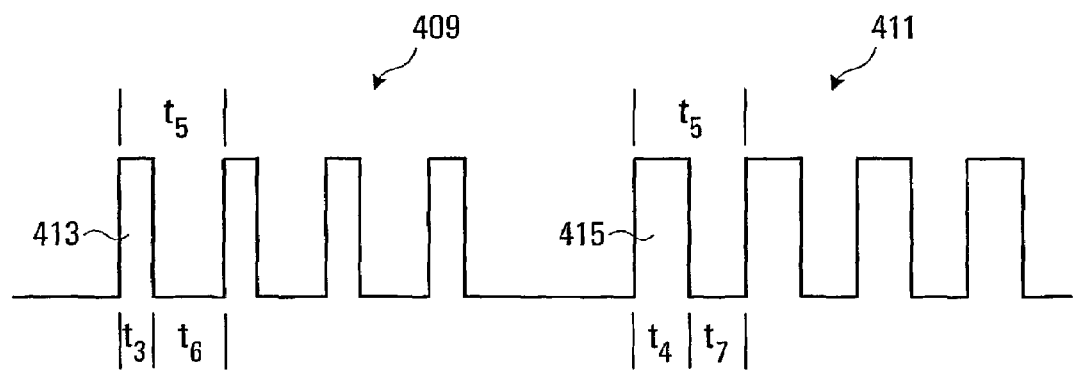

In another embodiment, the light source level or integrated photon flux is varied by varying the pulse width, an example of which is shown in FIG. 4B. FIG. 4B shows two pulse trains 409, 411, both pulse trains having the same number of pulses 413, 415. However, the pulse width $t_3$ of the pulses 413 of the first pulse train 409 is less than the pulse width $t_4$ of the pulses 415 of the second pulse train 411. The pulse period $t_5$ is the same for both pulse trains and therefore the time between pulses $t_6$ for the first pulse train 409 is greater than the time $t_7$ between pulses of the second pulse train 411. Thus, the integrated photon flux is larger for the second pulse train 411 than for the first pulse train 409.

The pulsing technique exemplified in FIG. 4A may be referred to as pulse frequency modulation (PFM) since the frequency of the pulses is varied between different pulse train sequences to vary the integrated photon flux. In this case, as the frequency is increased from $1/t_8$ to $1/t_9$, the integrated photon flux changes from F1 to F2, where $F2=F1 \times t9/t8$. The pulsing technique shown in FIG. 4B in which the pulse width is varied to change the integrated photon flux may be referred to as pulse width modulation (PWM). In PWM mode, the pulse period $t_5$ remains constant and the pulse width is varied. As the pulse width is increased from $t_3$ to $t_4$, the integrated photon flux changes from F3 to F4, where $F4=F3 \times t_4/t_3$. The controller is capable of generating either one or both forms of pulse sequence. In the examples of fluorescence measurements described below and shown in the drawings, the increase in integrated photon flux is represented on the X axis as "LED duty cycle", which for PFM mode would be $t_1/t_8$ (or $t_1/t_9$) and for PWM mode would be $t_3/t_5$ (or $t_4/t_5$). The LED duty cycles may typically vary between 0.00002 and 0.06, which represents an integrated photon flux of approximately 0.01 $\mu mol \cdot m^{-2} \cdot S^{-1}$ to $10$ $\mu mol \cdot m^{-2} \cdot S^{-1}$.

Figure 4C:
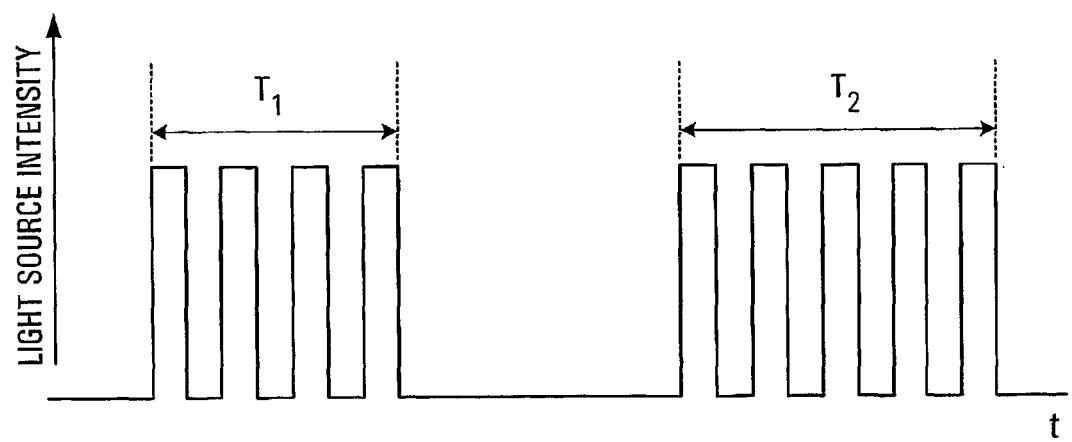

Another example of a pulsing technique which may be used to vary the integrated photon flux is shown in FIG. 4C. In this embodiment, the integrated photon flux is varied by varying the time period of each pulse train sequence.

Referring to FIG. 4C, the controller 17 controls the driver to pulse the intensity of the light sources at a predetermined frequency. For each fluorescence intensity measurement, the light sources are pulsed over a predetermined period of time $T_1$, $T_2$. Thus, the intensity of light to which the chlorophyll is exposed is the integral of the light intensity of each pulse over that time period. Thus, the intensity may be varied very sensitively, i.e. in very small increments, simply by changing the width of the time period over which the light sources are pulsed.

After each time period, the light source may be turned off so that the background fluorescence can be measured and subtracted from the data.

In another embodiment, the integrated photon flux may be varied by varying the intensity of the pulses. In other embodiments, the integrated photon flux may be varied by varying a combination of any two or more parameters which define a sequence of pulses.

The fluorescence received by the sensor may be measured when the light source is off, for example after each pulse in a pulse train, after some of the pulses, or at the end of each pulse train, or less frequently. The measured background fluorescence may be subtracted from the measured fluorescence intensity during each pulse to provide a measurement of the fluorescence intensity emitted solely in response to the light source.

The monitoring apparatus may be generally arranged to sample the fluorescence response of the chlorophyll containing matter periodically, for example under the control of a computer 23 (shown in FIG. 1). In one embodiment, a sample may involve exposing the chlorophyll containing matter to a single level of photon flux and detecting the intensity of the fluorescence signal emitted in response thereto. For example, the chlorophyll containing matter may be exposed to light having an intensity which stimulates a relatively low level of fluorescence, for example minimal fluorescence fo, or near minimal fluorescence, or a higher level of actinic fluorescence.

In another embodiment, a sample may involve exposing the chlorophyll containing matter sequentially to a plurality of different levels of integrated photon flux and detecting the fluorescence intensity or a parameter indicative of the fluorescence intensity at each level of photon flux.

A level of photon flux may be generated by energizing the light source at a predetermined intensity continuously for a predetermined period of time and the level of photon flux may be changed by energizing the light source at a different predetermined intensity continuously for a subsequent predetermined period of time. Between each photon flux level, the intensity of the light source may be reduced, for example to 0. The fluorescence intensity may be measured in response to each different level of photon flux and may also be measured when the light source is off, for example between changes in the intensity of the light source, so that the background fluorescence can be subtracted from the measured fluorescence at each different level of photon flux.

In other embodiments of the present invention, one or more different levels of photon flux may be generated by generating a predetermined series of light pulses. In this case, the level of photon flux is the integrated photon flux over the series of pulses. The integrated photon flux of each series of pulses depends on the parameters which define the pulses in each series, such as pulse intensity, pulse width, pulse rate (or frequency) and the number of pulses in each series, for example as described above in conjunction with FIGS. 4A to 4C. One or more of these parameters may be defined by an operator and input into a control system such as a computer by a user interface (e.g. graphical use interface (GUI), mouse, or keyboard). A plurality of different levels of integrated photon flux may be generated sequentially by generating a plurality of different series of pulses and by changing one or more parameters defining each series, for example the parameters mentioned above. For a single sample scan, the integrated photon flux may be progressively increased or decreased or different integrated photon fluxes may be generated in any selected or arbitrary order. Preferably, each scan includes at least three different levels of integrated photon flux to allow a second order polynomial to be parameterized to the data. The accuracy to which the parameters describing the polynomial regression can be determined increases with the number of fluorescence intensity data at different levels of integrated photon flux, and advantageously, this technique of generating different levels of integrated photon flux by pulsing the light source allows the integrated photon flux to be changed very precisely in very small increments, allowing a single scan to include many different levels of integrated of photon flux. For example, a single scan may include between 10 and 500 or more different levels of photon flux and typical measurements have been made using about 200 different levels of integrated photon flux. Other parameters which define a pulse scan may include the start and end levels of integrated photon flux, the increment of integrated photon flux between each successive level and the length of any pause (i.e. time period) between each successive level of integrated photon flux. In one embodiment where the level of integrated photon flux is progressively changed by changing the frequency (i.e. pulse rate) between successive series of pulses, parameters such as pulse width, start pulse rate, end pulse rate, pulse rate steps, number of pulses to be repeated at each pulse rate and pause between pulse rate steps may be selected.

In one embodiment, the chlorophyll fluorescence intensity may be measured during each pulse of a series of pulses defining a level of integrated photon flux. A single fluorescence intensity may be determined for each level of integrated photon flux by calculating the average fluorescence intensity of some or all of the fluorescence intensity measurements at each pulse.

Figure 5:
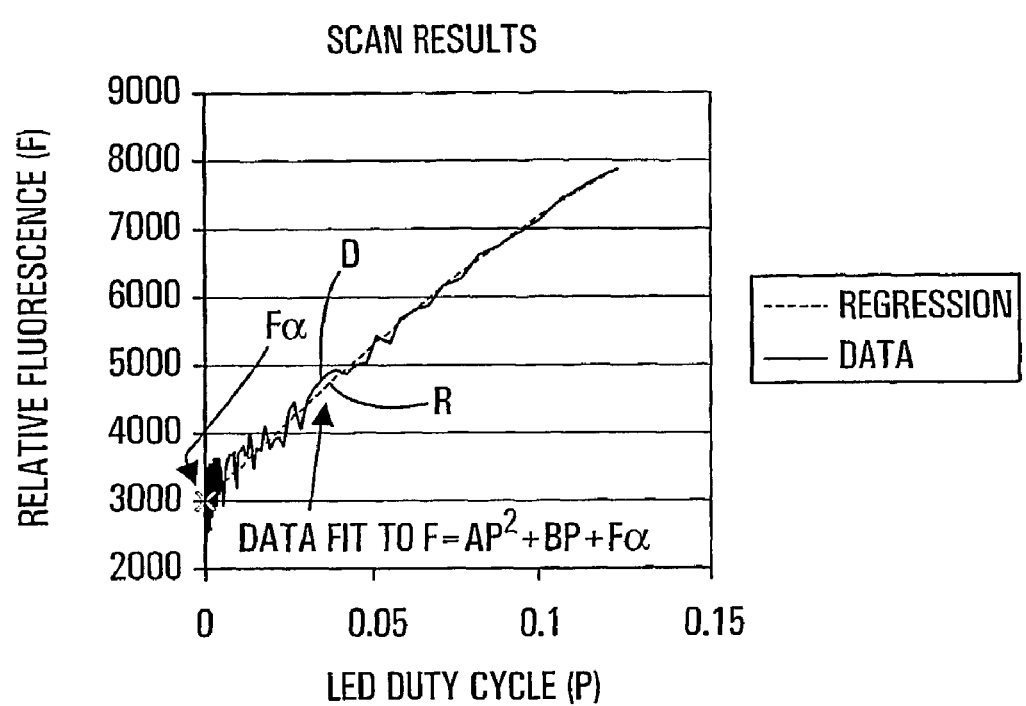
FIG. 5 shows an example of a graph of relative fluorescence intensity as a function of the integral photon flux emitted by a fluorescence stimulating light source.

Preferably, the fluorescence intensity is measured during each pulse and between each pulse (when the light source is off to provide an indication of the background fluorescence, e.g. due to any background light). The fluorescence intensity (D) after the light pulse is then subtracted from the fluorescence intensity (L) during the light pulse to provide a relative fluorescence (F), where F=L–D. Again, the average relative fluorescence intensity is determined over some or all of the series of pulses as mentioned above. For each fluorescence intensity measurement at each level of integrated photon flux, the duty cycle of the light source is also calculated as P=PW/PP, where PW is the pulse width and PP is the pulse period. As shown in FIG. 5, the fluorescence intensity generally increases with the level of integrated photon flux (which may be expressed as the light source duty cycle).

A second order polynomial regression of the form $F = A \times P^2 + B \times P + F\alpha$ is parameterized to the F vs. P curve. The F vs. P curve shitis and changes shape as chlorophyll containing matter experiences stress, for example to changing environmental parameters and this can be observed in the curve parameterizations A, B and $F\alpha$. Since a scan can typically represent a significant number of data points, these parameters have been found to be extremely stable when the chlorophyll containing matter is not undergoing physiological changes (e.g. due to stress). As mentioned above, the parameter $F\alpha$ represents the value of F that would be measured at P=0 (a theoretical point at which the integrated photon flux approaches 0), which has been shown to be a proxy for the traditional reading of Fo. The A and B parameters represent the curvature and slope of the F vs. P curve. These two parameters are very sensitive to physiological changes in chlorophyll containing matter e.g. fruits, vegetables and plants. The parameters $F\alpha$, A and B may be calculated from the data for example by a computer program. Changes in these parameters may also be calculated or may be observed by displaying the data visually, for example on a computer screen. Changes in these parameters may be compared with a determined level of change and the occurrence of a change above a predetermined level may be detected and, for example, signified to an operator. The detection of the parameter exceeding a predetermined level of change may signify that the health of the chlorophyll containing matter is being stressed, and such a determination may be used to control a parameter effecting the chlorophyll containing matter, for example an environmental parameter such gaseous mixture, temperature, moisture level, pressure or any other influence to which parameters derived from fluorescence intensity measurements are sensitive.

While a constant (i.e. non-scanning) pulse can be used to repeatedly measure a single fluorescence reading, it can be difficult to detect changes from that reading because of inherent noise levels. Thus, the scanning technique is preferred because of its greater sensitivity to change. Methods, e.g. algorithms which automatically signal significant change, for example as defined by an operator, can be defined generally or specifically for different applications.

Changes in the fluorescent measurements have been shown to directly relate to changes in the "health" of the chlorophyll containing matter caused by variations, for example, in environmental conditions and parameters such gaseous mixture, temperature, time and moisture. Thus, the state of the health of chlorophyll containing matter (e.g. plants, fruit and vegetables) due to their environment, whether stable, improving or under stress, can be determined with this methodology so that appropriate action can be taken. The detection of a significant change in a parameter based on the chlorophyll fluorescence may be used in an automated system as a control signal to control a parameter affecting the health of the chlorophyll containing matter concerned.

Examples of measurements of the onset of stress and recovery from stress in the health of various chlorophyll containing matter such as fruits and vegetables which are produced by changes in a variety of different environmental conditions will be described below.

Monitoring Health in Fruit Varieties at Low Oxygen Concentrations

The following examples illustrate how embodiments of the present invention can be used to detect the onset of low oxygen stress in fruit varieties. For each fruit variety, samples of the fruit were placed in each of two containers. The fruit samples in one of the containers served as control samples and samples in the other container served as the treatment samples. The treatment containers were sealed and connected to a system which controls and monitors the oxygen levels within the container, an example of which is described below and shown in FIGS. 19, 20, 21 and 22. A cross-sectional view of a typical treatment container is shown in FIG. 2 and contains a stress monitoring device as described above in connection with FIG. 1. The oxygen concentration was initially lowered to 3% and thereafter the oxygen concentration was reduced by 0.5% every 12 hours to 0%. After 12 hours at 0% $O_2$, the oxygen concentration was re-established at 3%. This process created a gradual decrease in the oxygen concentration, ensuring that the fruit samples were subjected to a dangerous oxygen level for fruit health, followed by a recovery to a healthy oxygen level. For each fruit variety, the temperature was maintained at approximately 20° C. and $CO_2$ concentrations within the treatment containers were maintained at between 0 and 0.5% by placing small bags of hydrated lime in the containers which absorbed any $CO_2$ produced by the respiration of the fruit.

The stress monitoring apparatus was operated at regular intervals and for each measurement, the intensity of the fluorescence signal was measured and recorded for a number of different values of light source levels. A second order polynomial was fitted to each set of fluorescence intensity data providing the values of the parameters $F_\alpha$, A and B. An example of a set of measured data and a second order polynomial regression calculated for the data is shown in FIG. 5. The data is shown as the curve labelled 'D' and the polynomial regression is shown by the curve 'R'. This data set and regression is also typical of other experiments described below.

EXAMPLE 1

Low Oxygen Stress in Apple

Figure 6A:
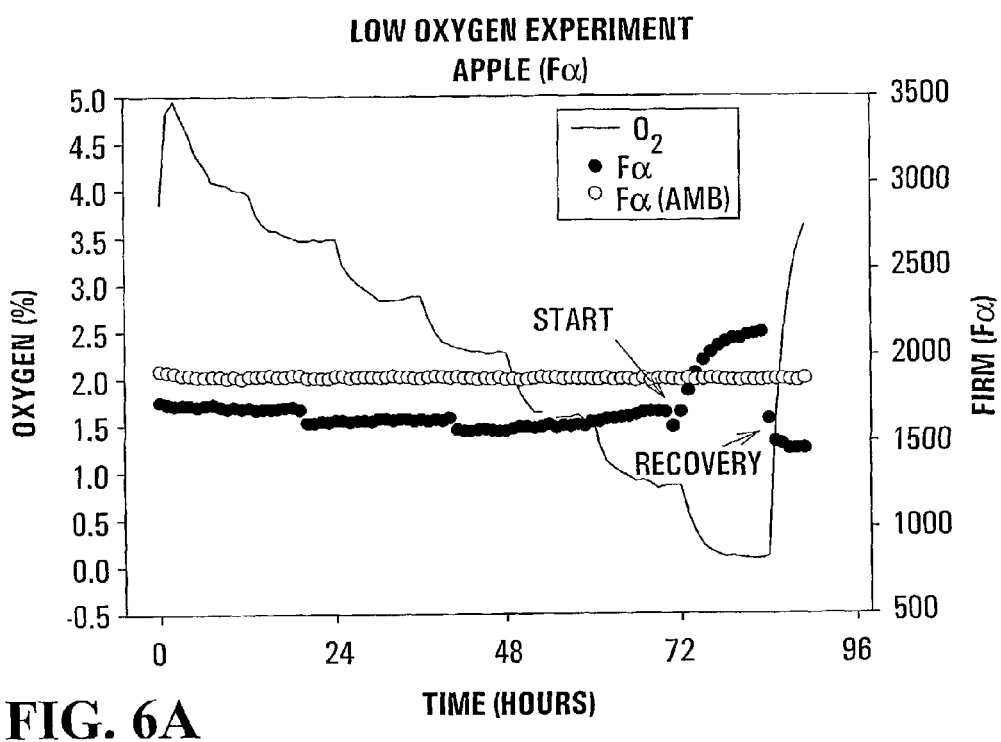
FIGS. 6A to 6D show examples of measurements of low oxygen stress in apple samples.
Figure 6B:
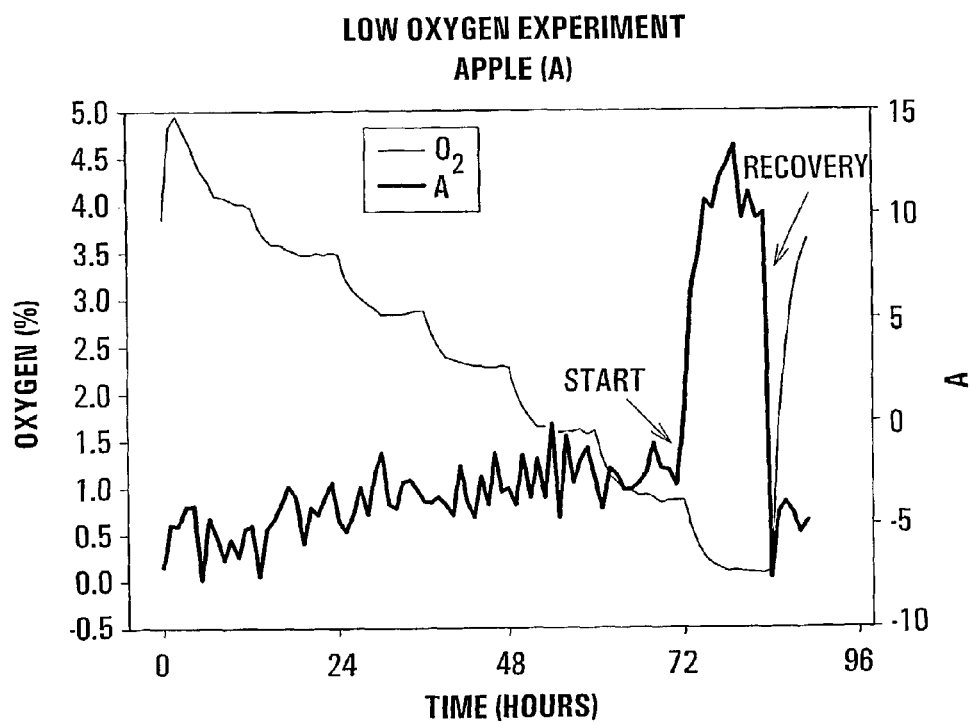
Figure 6C:
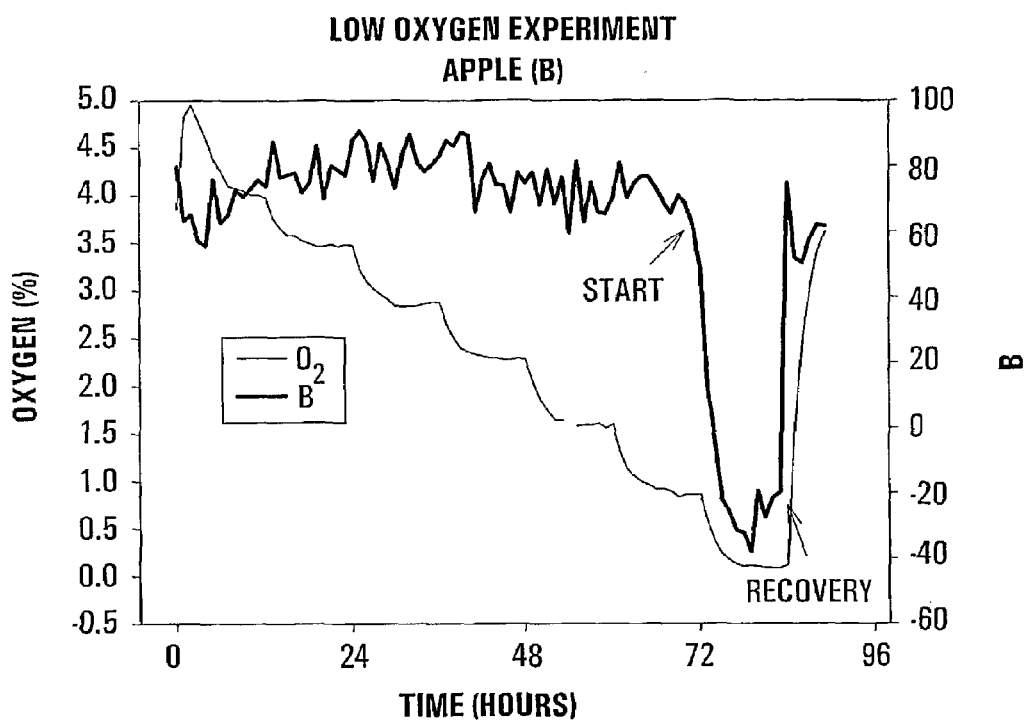
Figure 6D:
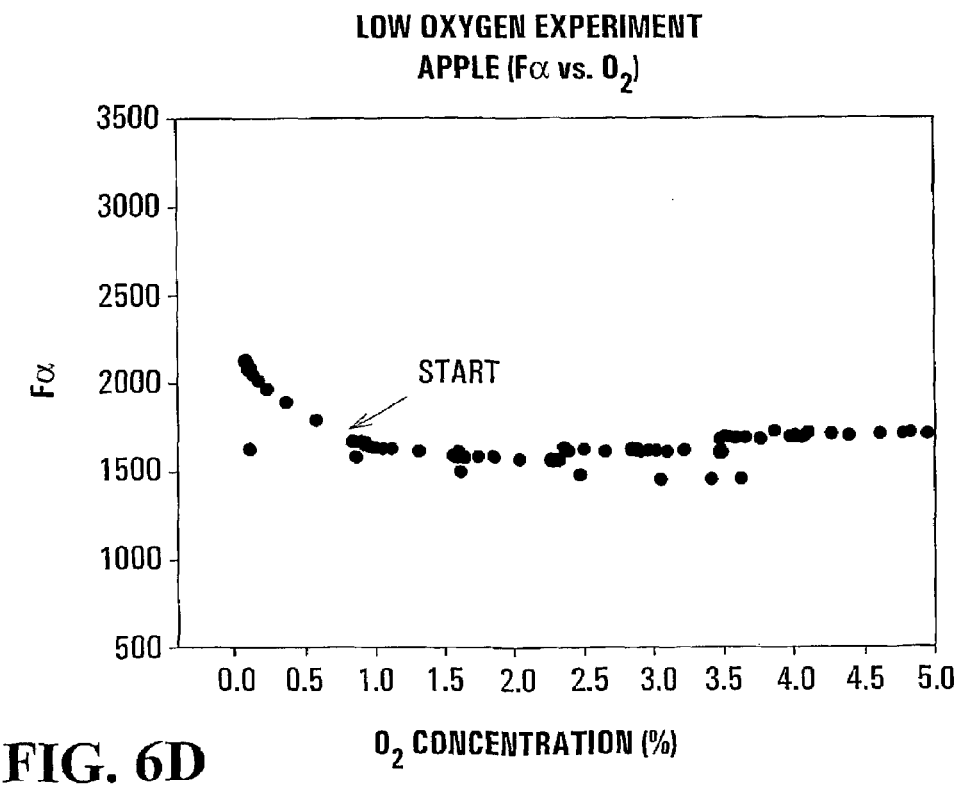
Figure 7A:
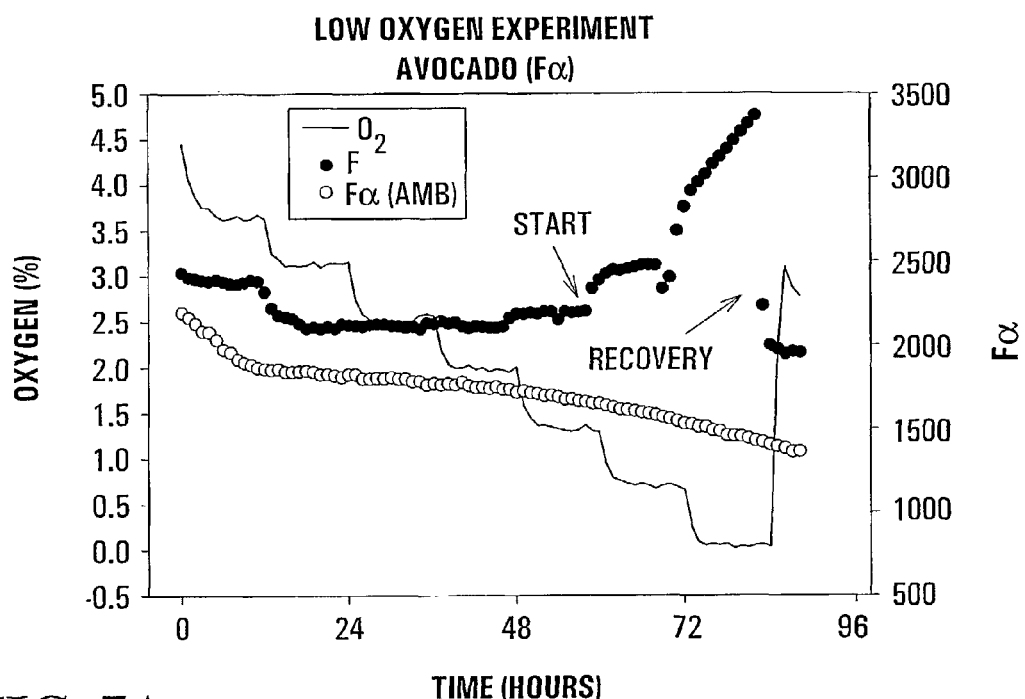
FIGS. 7A to 7D show examples of measurements of low oxygen stress in avocado samples.
Figure 7B:
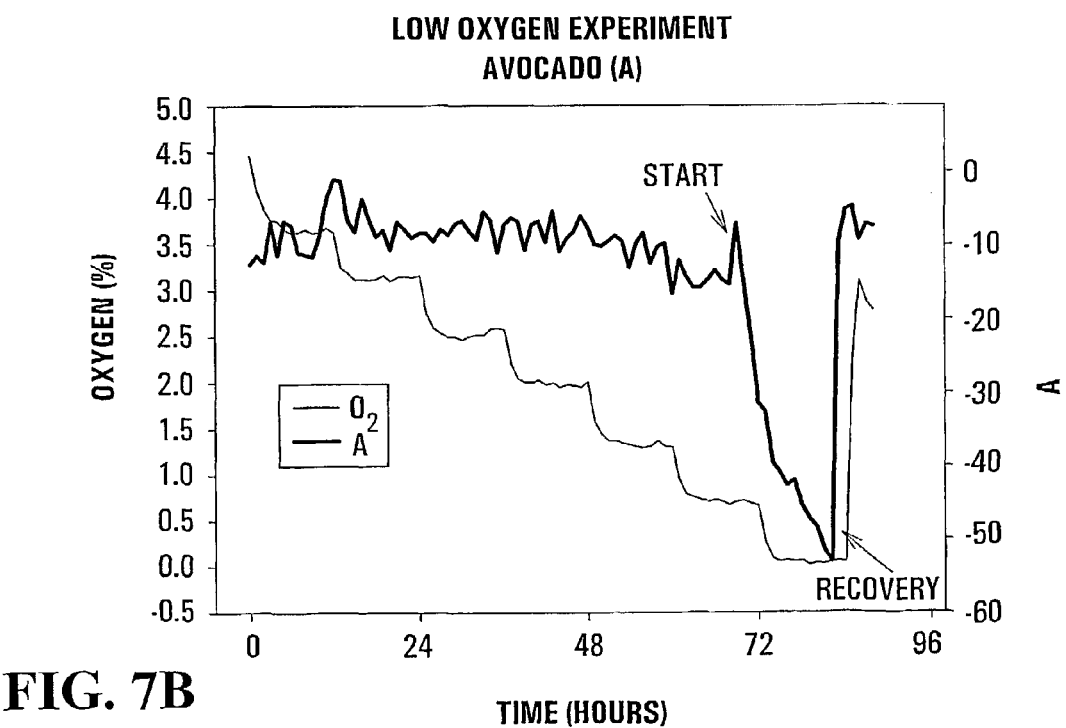
Figure 7C:
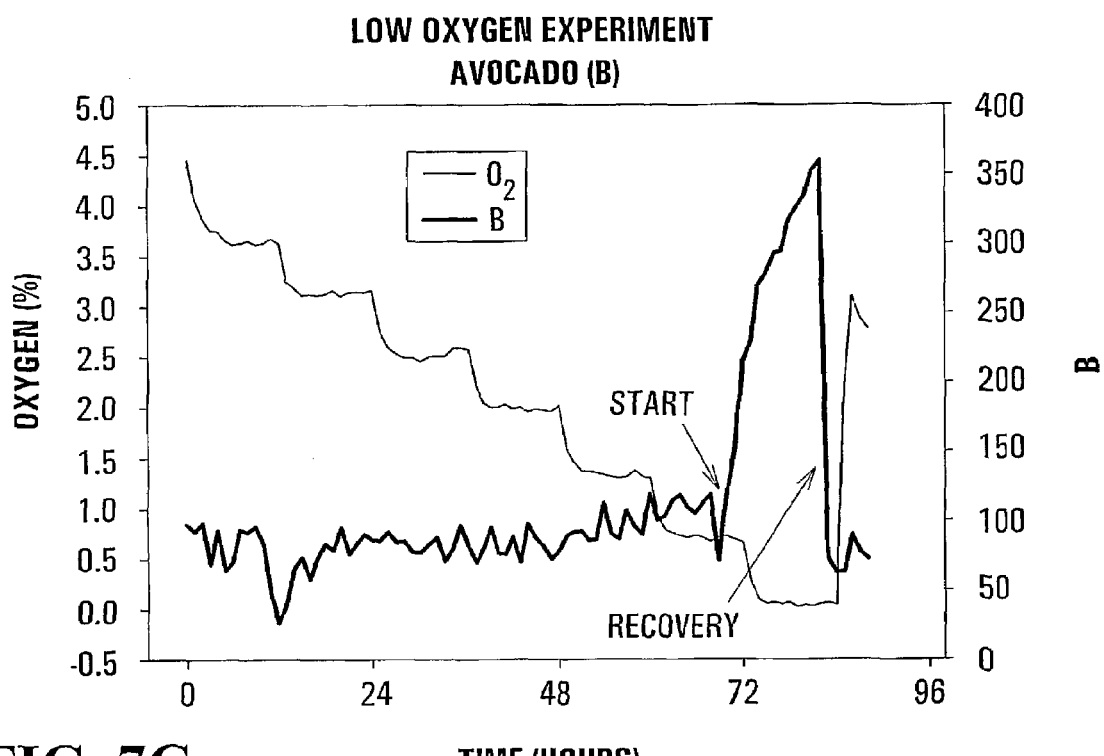
Figure 7D:
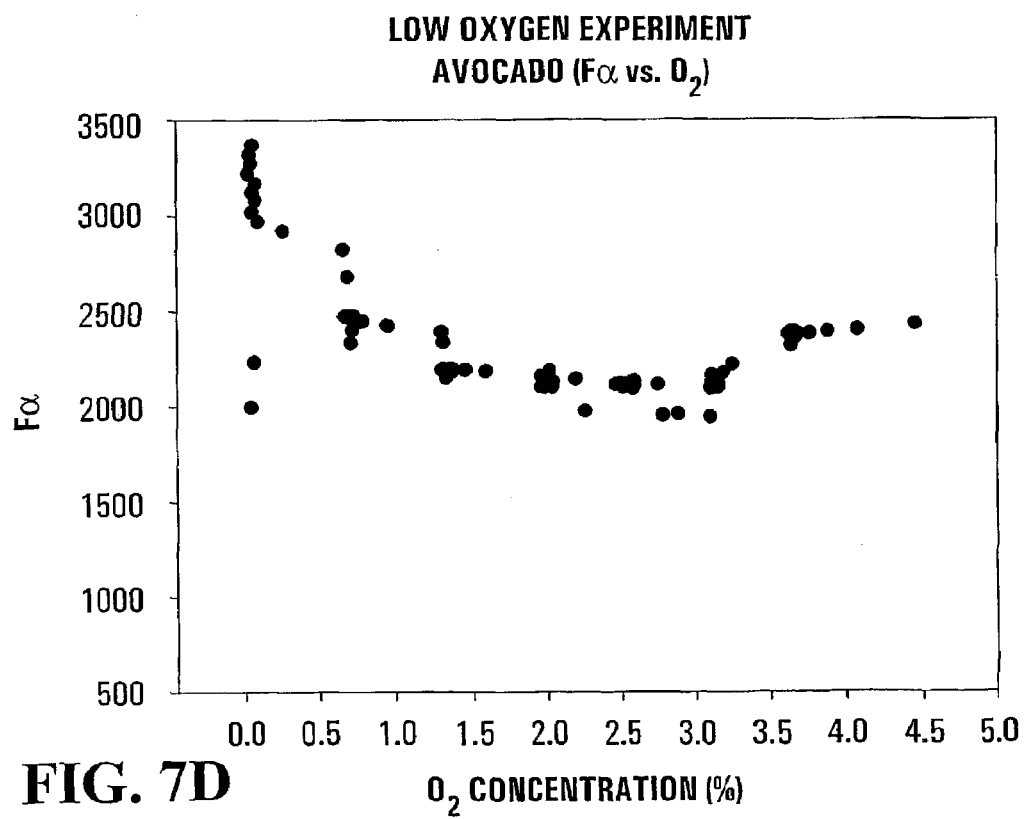

FIGS. 6A to 6D show examples of the measured response of apple samples as the oxygen concentration is progressively reduced. FIGS. 6A, 6B and 6C show the variation of parameters $F_\alpha$, A and B, respectively, as the oxygen concentration is reduced over time, and FIG. 6D shows the variation of $F_\alpha$ with oxygen concentration. Progressing from higher to lower oxygen concentrations, each of the parameters $F_\alpha$, A and B exhibit little change until hour 72 corresponding to an oxygen concentration of about 1%. At this concentration, $F_\alpha$ and parameter A increase abruptly, as shown at 'start', whereas parameter B exhibits a sharp decrease. $F_\alpha$ continues to increase as the oxygen concentration is lowered further and until the oxygen concentration reaches 0%. As the oxygen concentration is rapidly increased, $F_\alpha$ rapidly decreases to a similar level to that just prior to the onset of the rapid increase. Thus, $F_\alpha$ can provide both an indication of the onset of a stress condition and recovery from a stress condition.

From their respective transition points, both parameters A and B continue to increase and decrease, respectively as the oxygen concentration is lowered below 1% and both exhibit a rapid change in the opposite direction when the oxygen concentration is quickly re-established. Thus, both parameters A and B also indicate the onset of a stress condition and recovery from the stress condition.

EXAMPLE 2

Low Oxygen Stress in Avocado

FIGS. 7A to 7D show examples of the response of avocado samples as the oxygen concentration is reduced. Progressing from higher to lower oxygen concentrations, the parameter $F_\alpha$ initially exhibits little change followed by a marked increase at an oxygen concentration of just below 1.5%. As the oxygen concentration is lowered further, $F_\alpha$ makes a second abrupt increase at an oxygen concentration of between 0.5 and 1%. At an oxygen concentration corresponding approximately to the second transition, parameters A and B also exhibit a marked change, with parameter A decreasing and parameter B increasing. This is the opposite change to that observed with the apple sample in which parameter a increased and parameter B decreased. $F_\alpha$ continues to increase until the oxygen concentration drops to zero and then rapidly decreases to a value similar to that just prior to the positive transition when the oxygen concentration is quickly reestablished. Parameters A and B also continue to change rapidly as the oxygen concentration is reduced to 0% and then exhibit a sudden change in the opposite direction after the oxygen concentration has remained at 0% for a certain length of time but before the oxygen concentration is quickly returned to about 3%.

EXAMPLE 3

Low Oxygen Stress in Banana

Figure 8A:
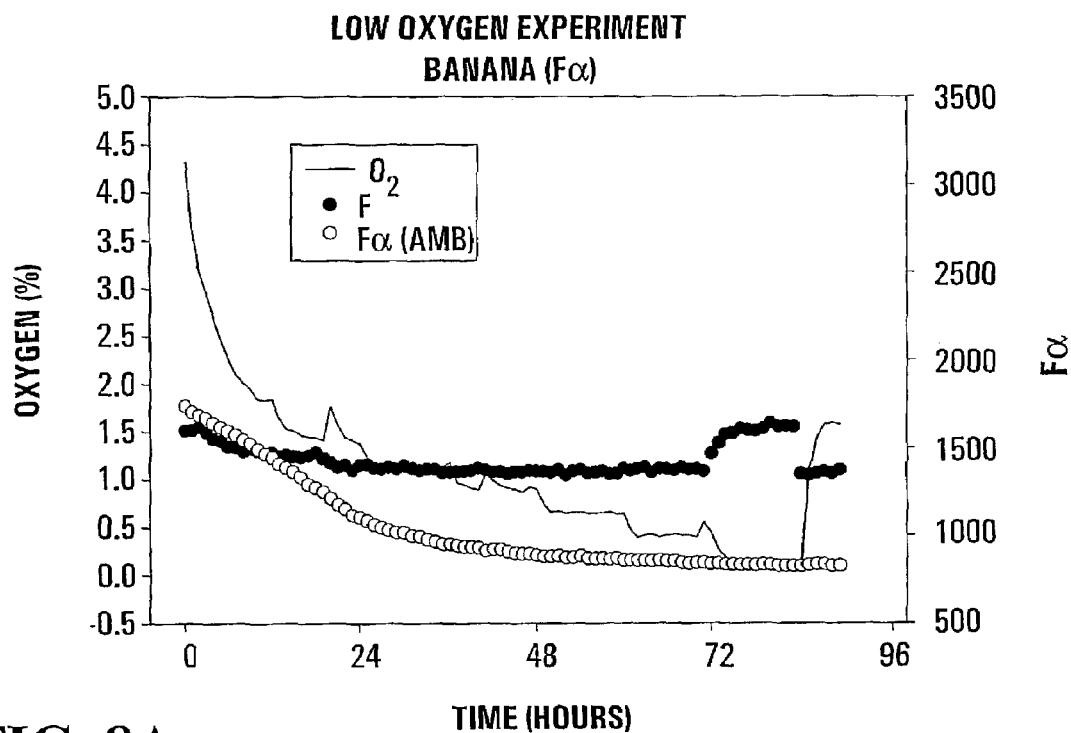
FIGS. 8A to 8D show examples of measurements of low oxygen stress in banana samples.
Figure 8B:
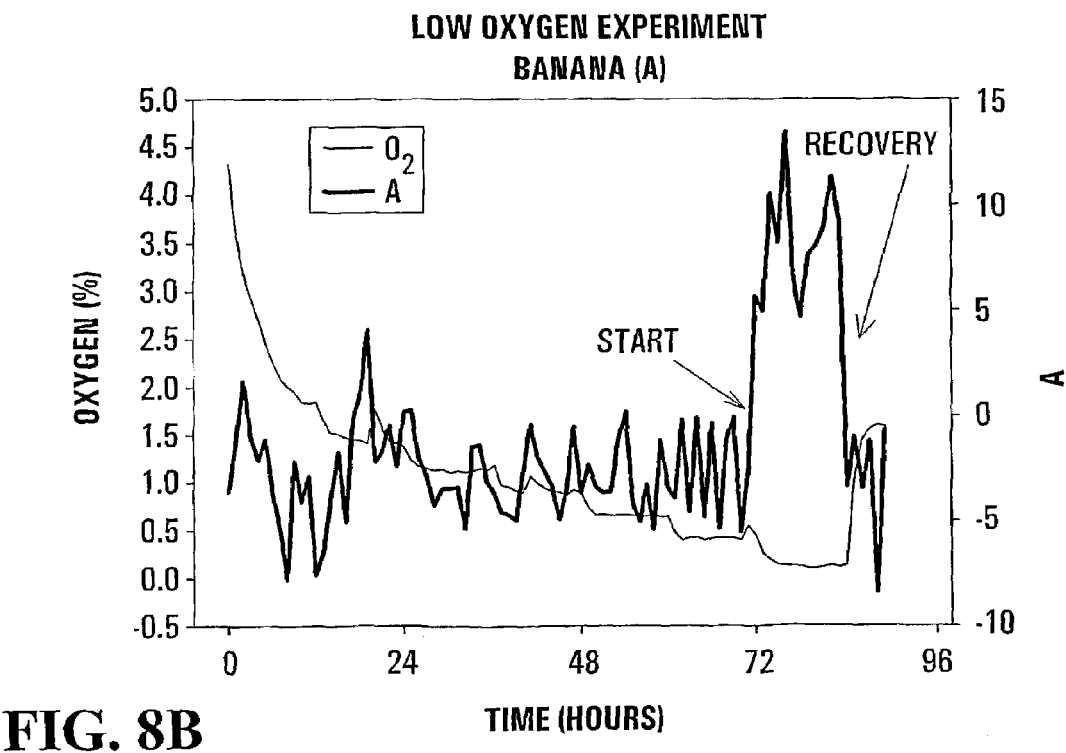
Figure 8C:
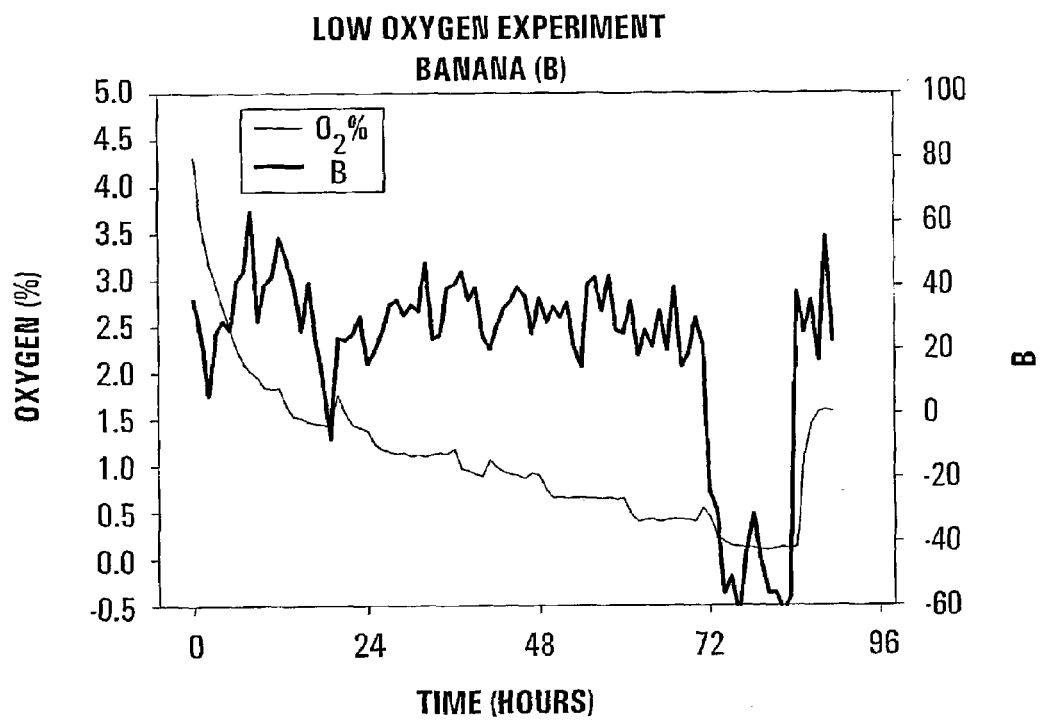
Figure 8D:
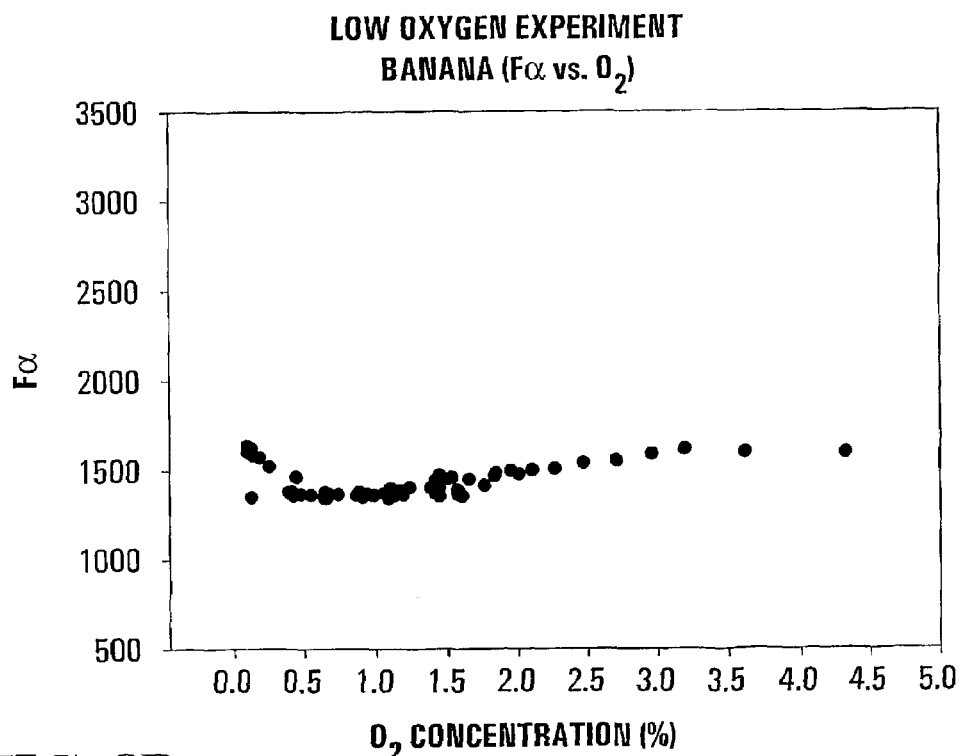

FIGS. 8A to 8D show examples of the measured fluorescence response of banana samples as the oxygen concentration is progressively reduced. FIGS. 8A, 8B and 8C show the variation of parameters $F_\alpha$, A and B, respectively, as the oxygen concentration is reduced over time, and FIG. 8D shows the variation of $F_\alpha$ with oxygen concentration. The banana samples used were initially fully green and therefore had an adequate supply of chlorophyll in the skin to generate fluorescence signals. Progressing from higher to lower oxygen concentrations, $F_\alpha$ remains substantially constant between about hour 24 and hour 70 as the oxygen concentration is progressively reduced from about 1.5 to 0.5%. Over the same time period, parameters A and B fluctuate about a substantially constant value. At an oxygen concentration of approximately 0.5%, $F_\alpha$ and parameter A increase abruptly, whereas parameter B exhibits a sharp decrease, indicating the onset of low oxygen stress in the banana samples. $F_\alpha$ continues to increase as the oxygen concentration is lowered further until the oxygen concentration reaches zero percent. Parameter A generally continues to increase and parameter B generally continues to decrease as the oxygen concentration is lowered from 0.5% to 0%. As the oxygen concentration is rapidly increased to above the level at which the positive transition in $F_\alpha$ occurred, $F_\alpha$ rapidly decreases to a similar value to that just prior to the positive transition, indicating the recovery from stress in the banana samples. As the oxygen concentration is rapidly increased from 0%, the values of parameters A and B decrease and increase, respectively, to within their range of values prior to the onset of low oxygen stress and also provide an indicator of the recovery from stress in banana.

FIG. 8A also shows that the value of $F_\alpha$ for the control sample of bananas held at ambient conditions steadily decreases and then tends to a constant value over time. Over this time period, the control banana samples visibly ripened, thus losing chlorophyll and turning yellow. Therefore, $F_\alpha$ provides a sensitive indicator of the loss of chlorophyll as bananas ripen.

EXAMPLE 4

Low Oxygen Stress in Kiwi Fruit

Figure 9A:
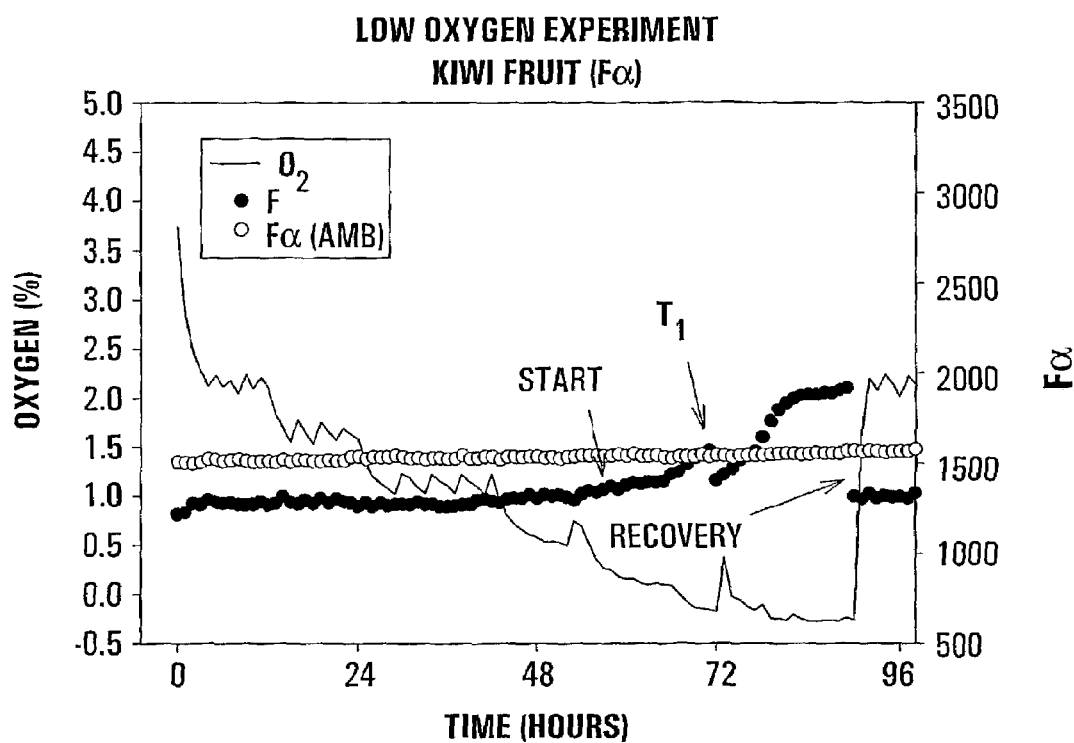
FIGS. 9A to 9D show examples of measurements of low oxygen stress in kiwi fruit samples.
Figure 9B:
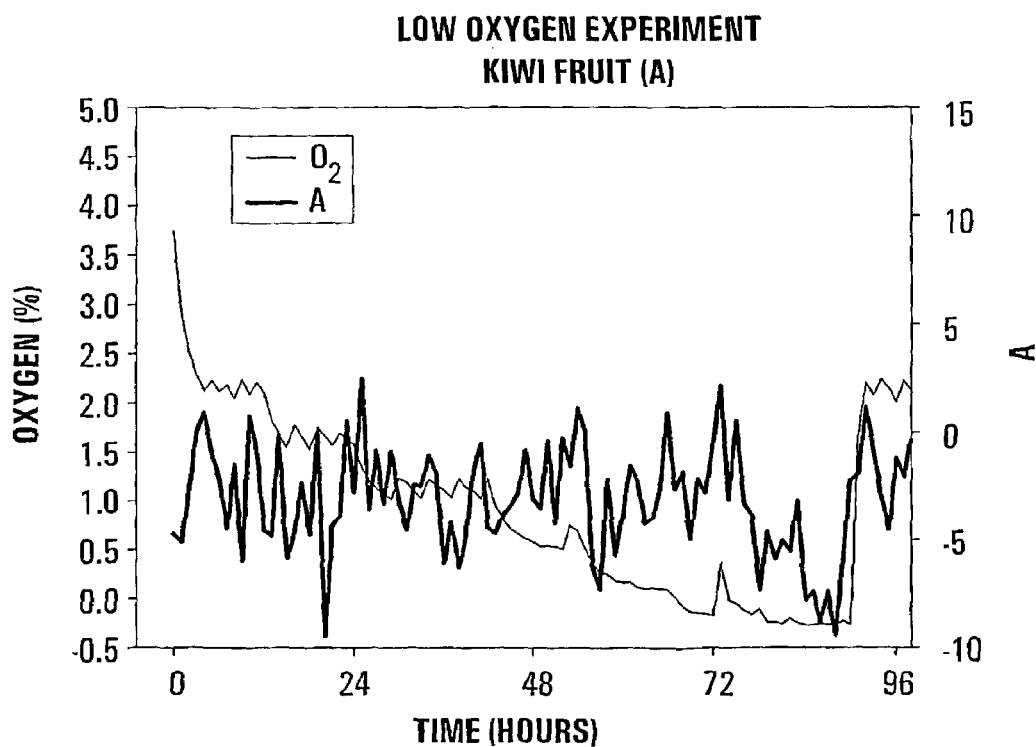
Figure 9C:
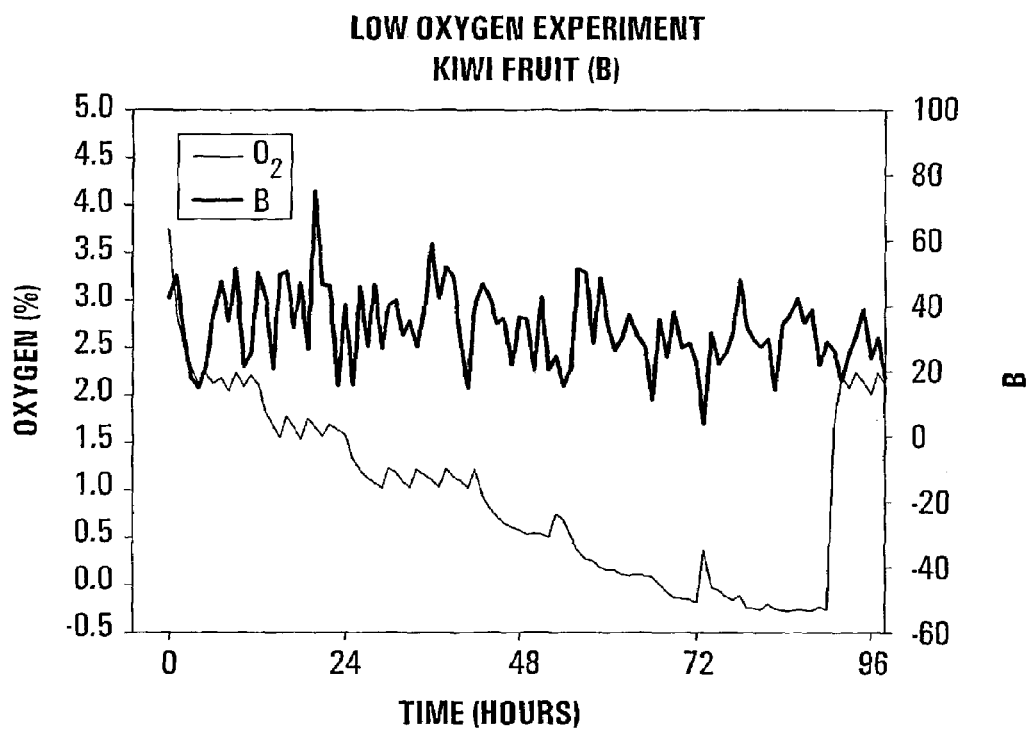
Figure 9D:
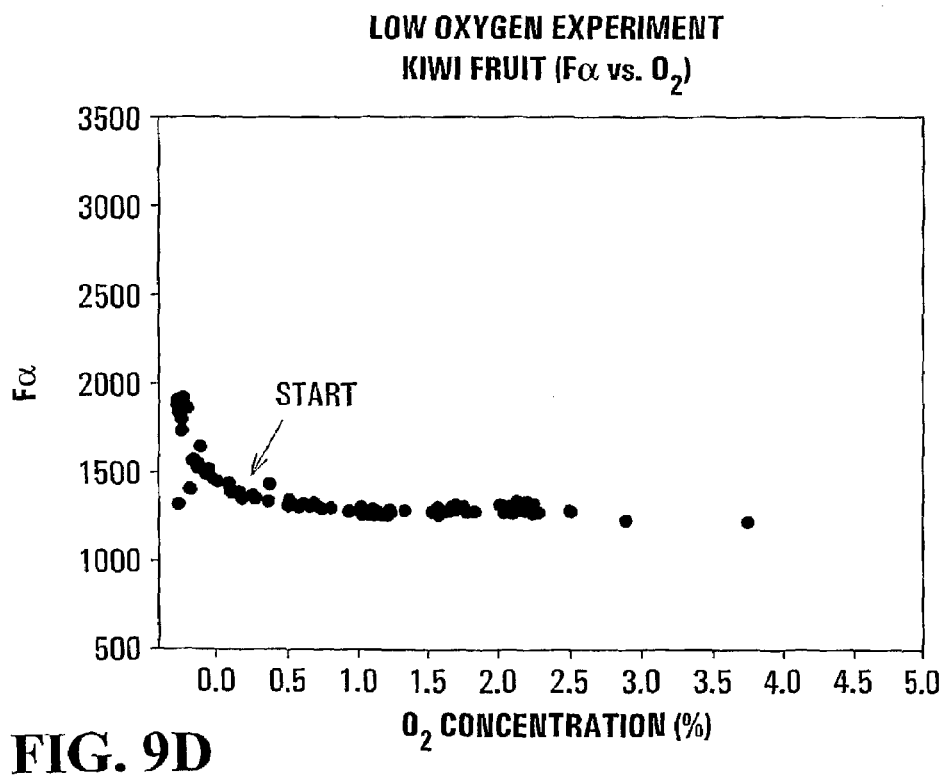

FIGS. 9A to 9D show examples of the measured fluorescence response of kiwi fruit with varying oxygen concentration. Referring to FIGS. 9A and 9D, $F_\alpha$ exhibits little change as the oxygen concentration is reduced until about hour 57 corresponding to an oxygen concentration of about 0.25%. At this point, particularly as shown in FIG. 9D, $F_\alpha$ abruptly increases, indicating the onset of low oxygen stress, and continues to increase as the oxygen concentration is lowered further. As shown in FIG. 9A, $F_\alpha$ rapidly decreases at position $T_1$ as the oxygen concentration is increased again to about 0.5% at approximately hour 72. As the oxygen concentration is again lowered shortly thereafter, $F_\alpha$ again increases rapidly as the oxygen concentration is lowered to 0%, again indicating the onset of low oxygen stress in the kiwi samples. As the oxygen concentration is rapidly increased from 0% to above the low oxygen stress threshold value, $F_\alpha$ rapidly decreases to approximately its former value before the onset of low oxygen stress. Thus, $F_\alpha$ provides a sensitive indicator of both the onset of and recovery from low oxygen stress in kiwi fruit. As shown in FIG. 9A, the value of $F_\alpha$ for the control sample shows very little change during the period over which the tests were conducted and no visible change in the color of the control samples was observed over this period. The values of the parameters A and B fluctuate over the test period but the onset of and recovery from low oxygen stress is not as readily indicated by these parameters in the sample under test, as the measurements of $F\alpha$.

EXAMPLE 5

Low Oxygen Stress in Mango Fruit

Figure 10A:
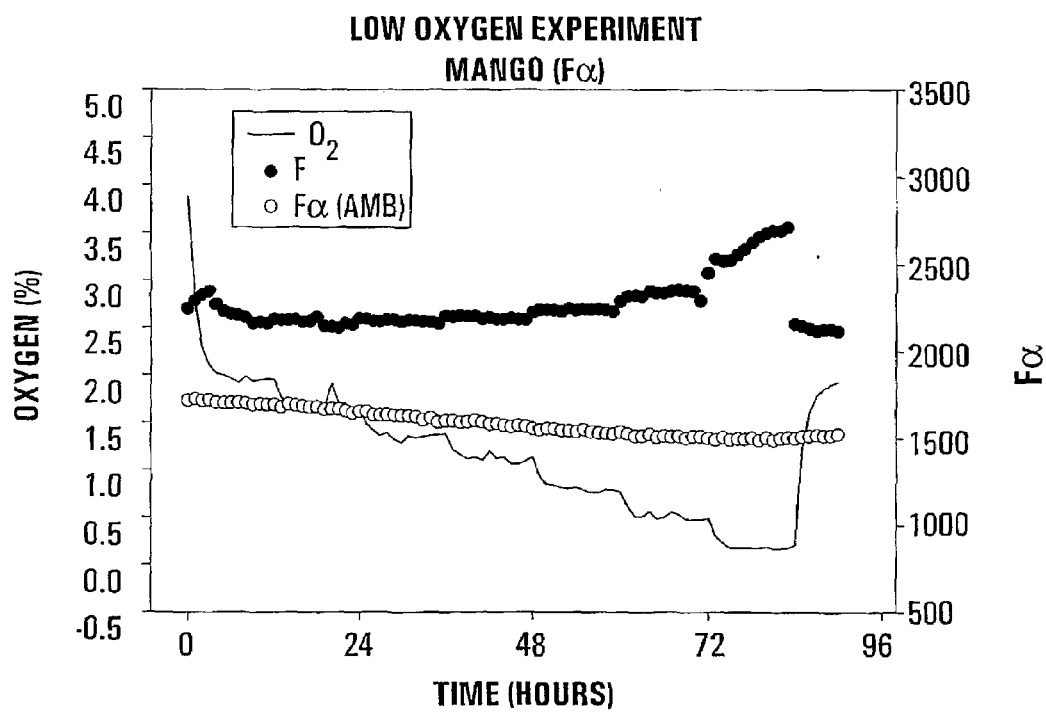
FIG. 10A to 10D show examples of measurements of low oxygen stress in mango samples.
Figure 10B:
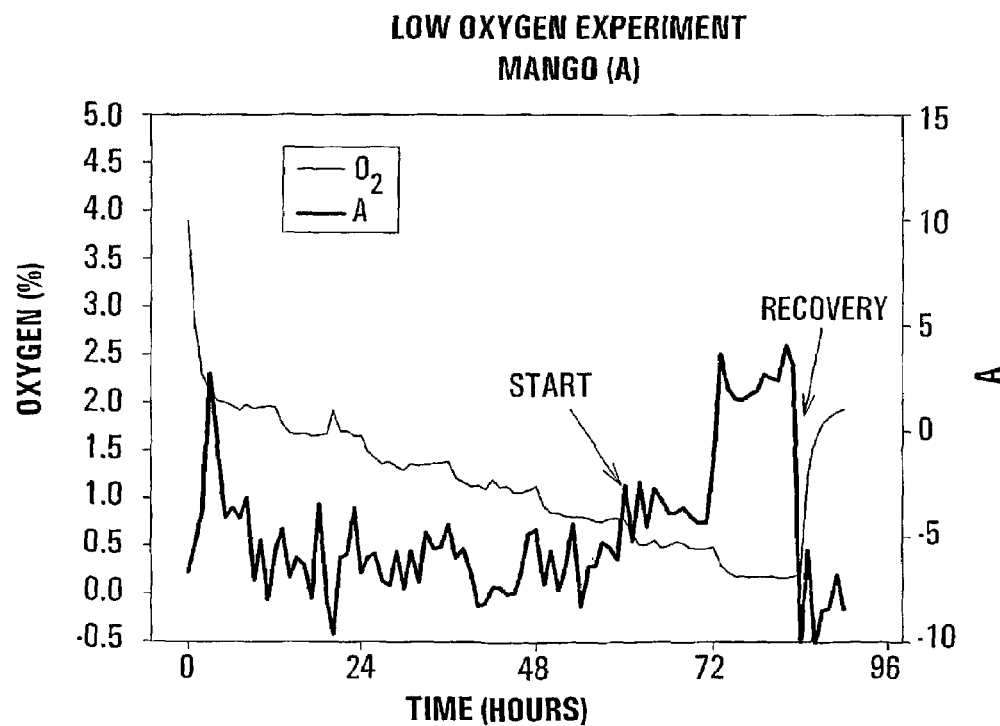
Figure 10C:
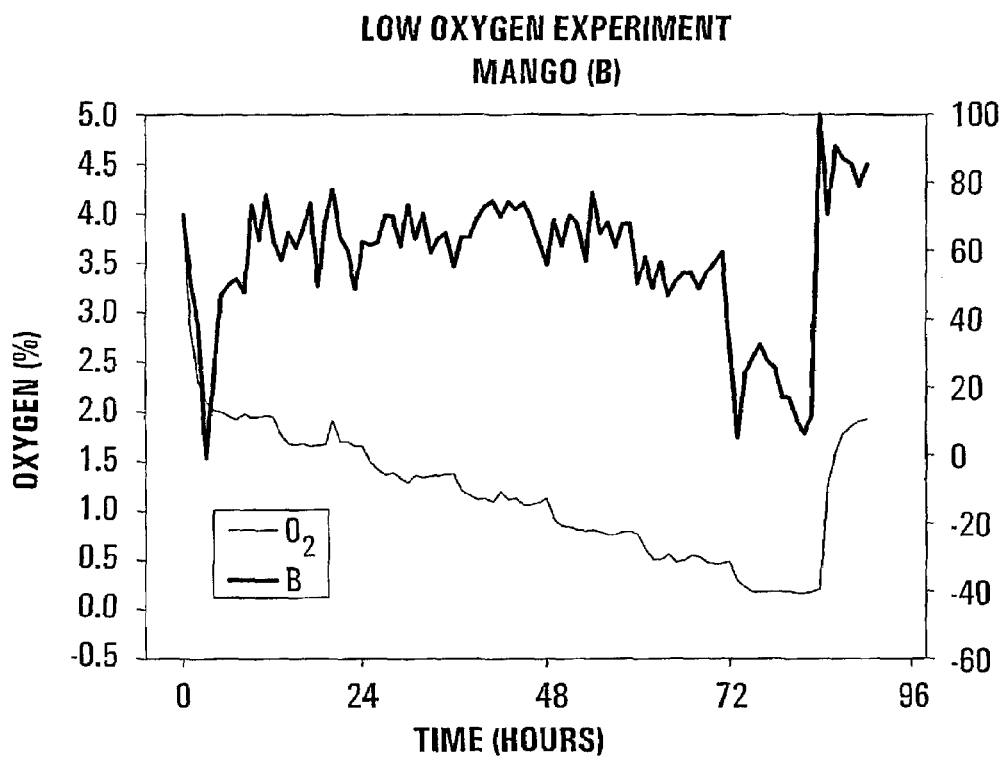
Figure 10D:
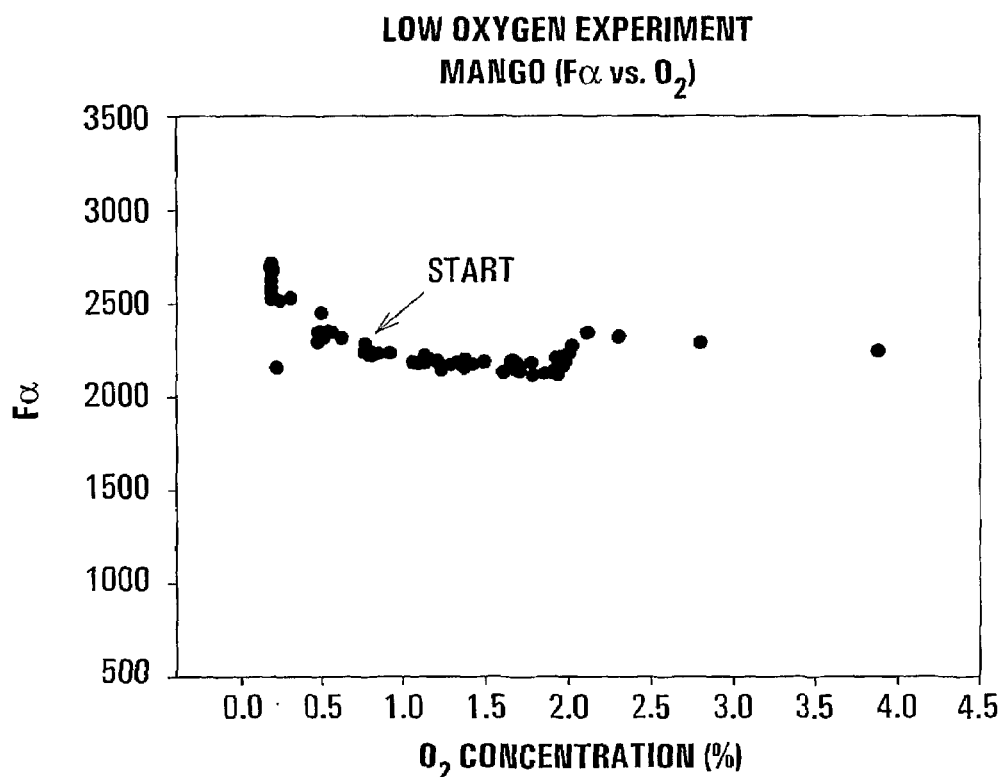

FIGS. 10A to 10D show examples of the measured fluorescence response of mango samples as the oxygen concentration is varied. Initially, as the oxygen concentration is reduced, $F_\alpha$ gradually increases, until at approximately hour 60 corresponding to an oxygen concentration of about 0.75%, the change in $F_\alpha$ abruptly increases (particularly as shown in FIG. 10D) as the oxygen concentration is reduced further to 0%, indicating the onset of stressing the health in the mango samples. Thereafter, $F_\alpha$ rapidly decreases to approximately its former value before the onset of low oxygen stress as the oxygen concentration is rapidly increased again to above the low oxygen stress threshold level, thus indicating the recovery of the mango sample from low oxygen stress.

Parameters A and B fluctuate about a substantially constant value as the oxygen concentration is progressively reduced until an oxygen concentration of approximately 0.75% at which point, parameter A generally increases and parameter B generally decreases, and therefore parameters A and B also provide an indication of the onset of stress. As the oxygen concentration is lowered further from 0.5% to 0%, parameter A exhibits a rapid increase and parameter B exhibits a rapid decrease. This indicates that parameters A and B are particularly sensitive to stress at low oxygen concentrations. After the oxygen concentration has been held at 0% parameter A rapidly decreases and parameter B rapidly increases when the oxygen concentration is increased to levels above the low oxygen stress threshold, indicating the recovery of mango fruit from low oxygen stress.

As shown in FIG. 10A, the value of $F_\alpha$ for the control sample gradually decreases and tends to a constant value over the test period and indicates a gradual loss of chlorophyll as the mangoes ripen which was also indicated visually as the mango samples changed from green to red or red to yellow over the same period.

EXAMPLE 6

Low Oxygen Stress in Pear

FIGS. 11A to 11D show examples of the measured fluorescence response of pear samples with varying oxygen concentration. As the oxygen concentration is reduced, $F_\alpha$ initially decreases to about hour 24 at an oxygen concentration of approximately 1.5% and then remains approximately constant until about hour 48 corresponding to an oxygen concentration of about 0.6%. As the oxygen concentration is lowered below about 0.6%, $F_\alpha$ increases, indicating the onset of low oxygen stress. Above an oxygen concentration of approximately 0.6%, parameters A and B fluctuate about a substantially constant value and parameter A exhibits a general increase and parameter B a general decrease as the oxygen concentration is reduced below approximately 0.6%. $F_\alpha$ and parameter A continue generally to increase as the oxygen concentration is lowered to 0% and parameter B generally continues to decrease. As the oxygen concentration is rapidly increased from 0% to above the low oxygen stress threshold, $F_\alpha$ and parameter A rapidly decrease to approximately their respective values prior to the onset of low oxygen stress and parameter B rapidly increases, again returning to its former value prior to the onset of low oxygen stress.

Figure 11A:
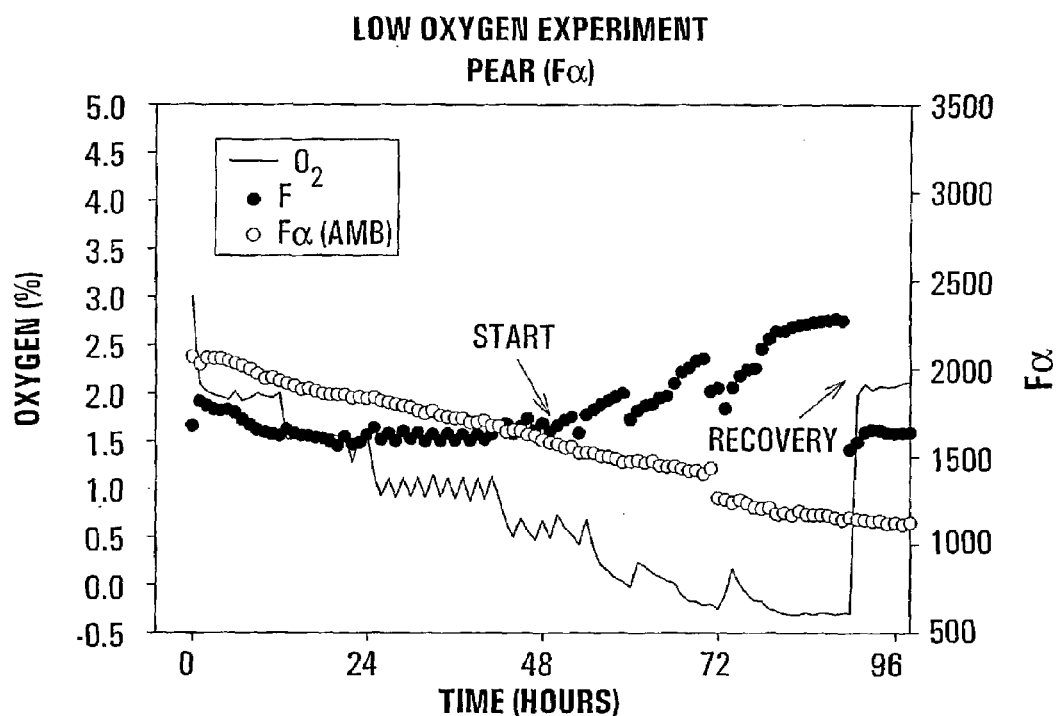
FIG. 11A to 11D show examples of low oxygen stress in pear samples.
Figure 11B:
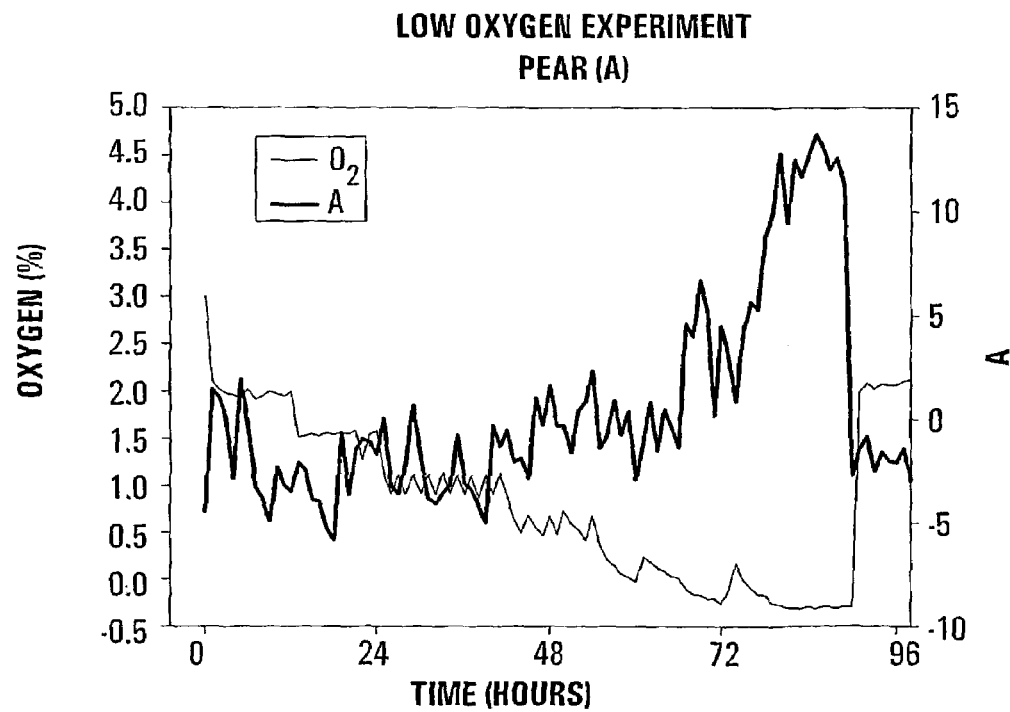
Figure 11C:
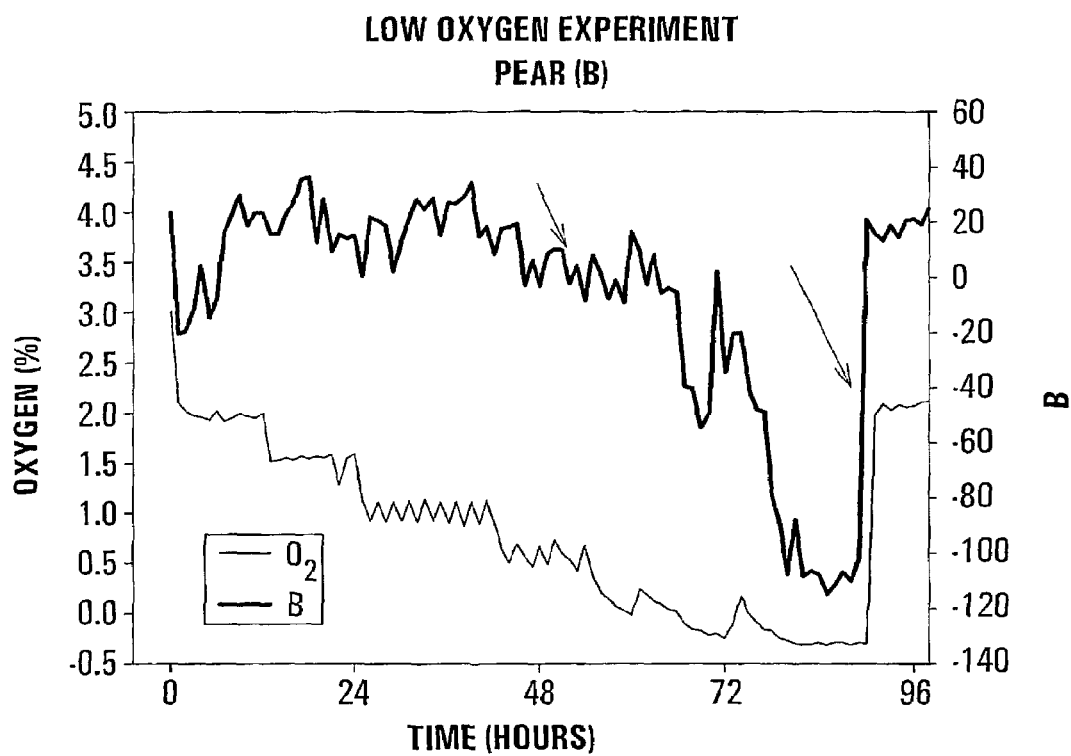
Figure 11D:
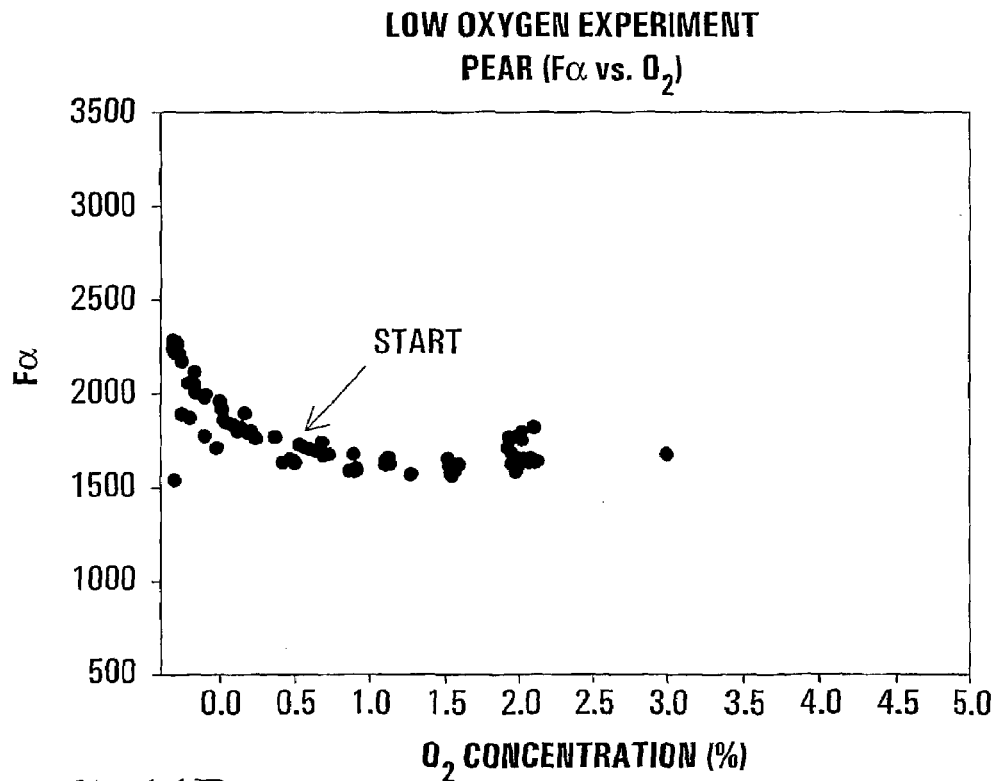
Figure 12A:
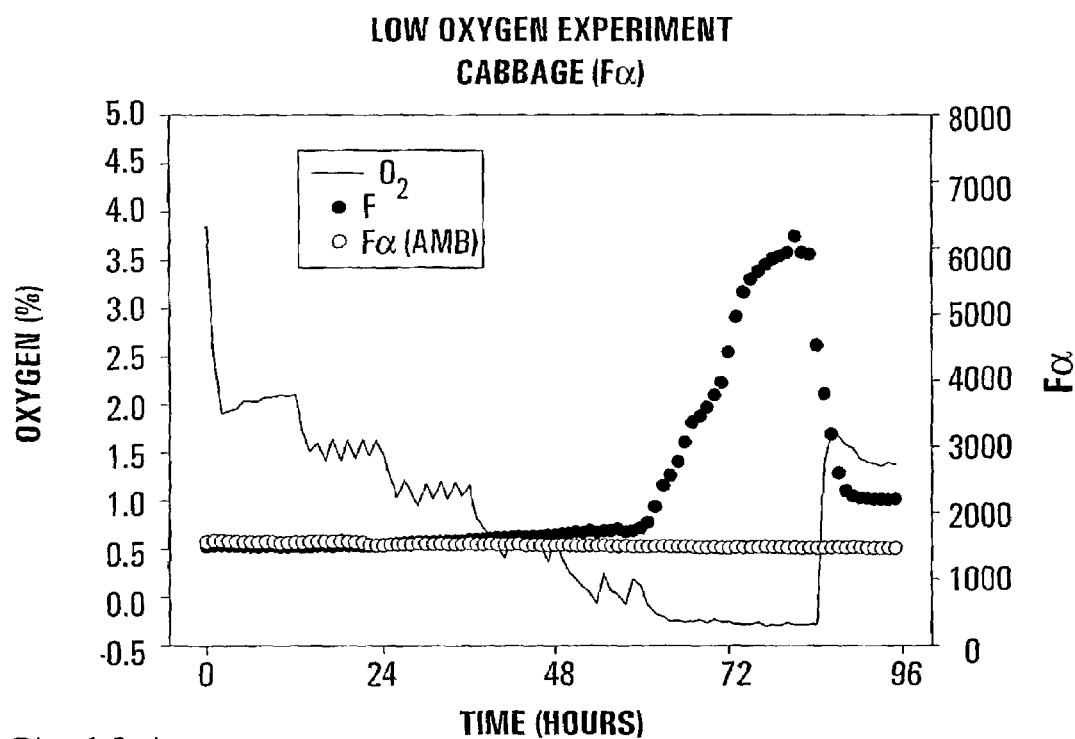
FIGS. 12A to 12D show examples of measurements of low oxygen stress in cabbage samples.
Figure 12B:
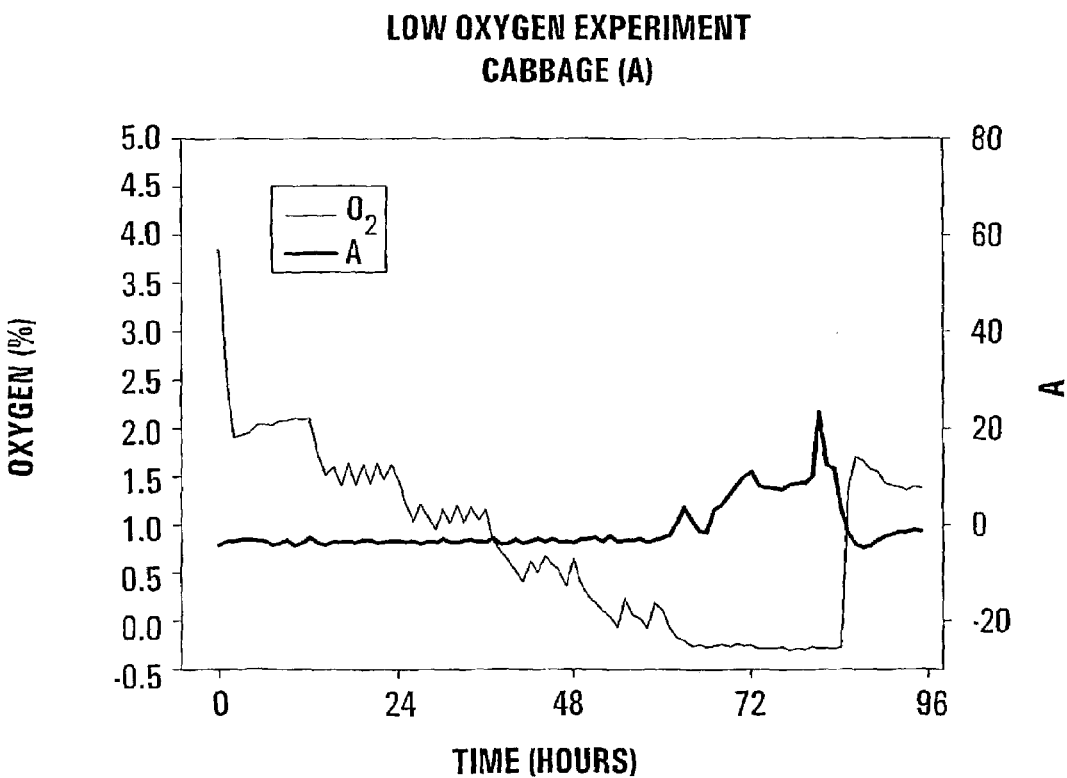
Figure 12C:
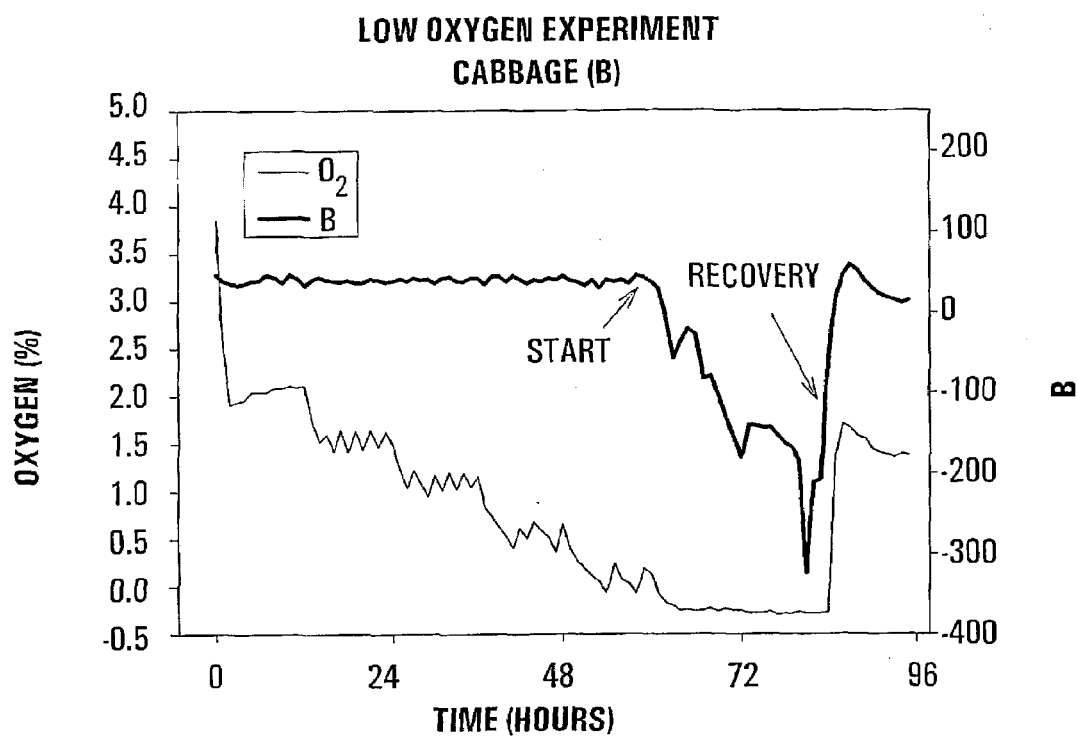
Figure 12D:
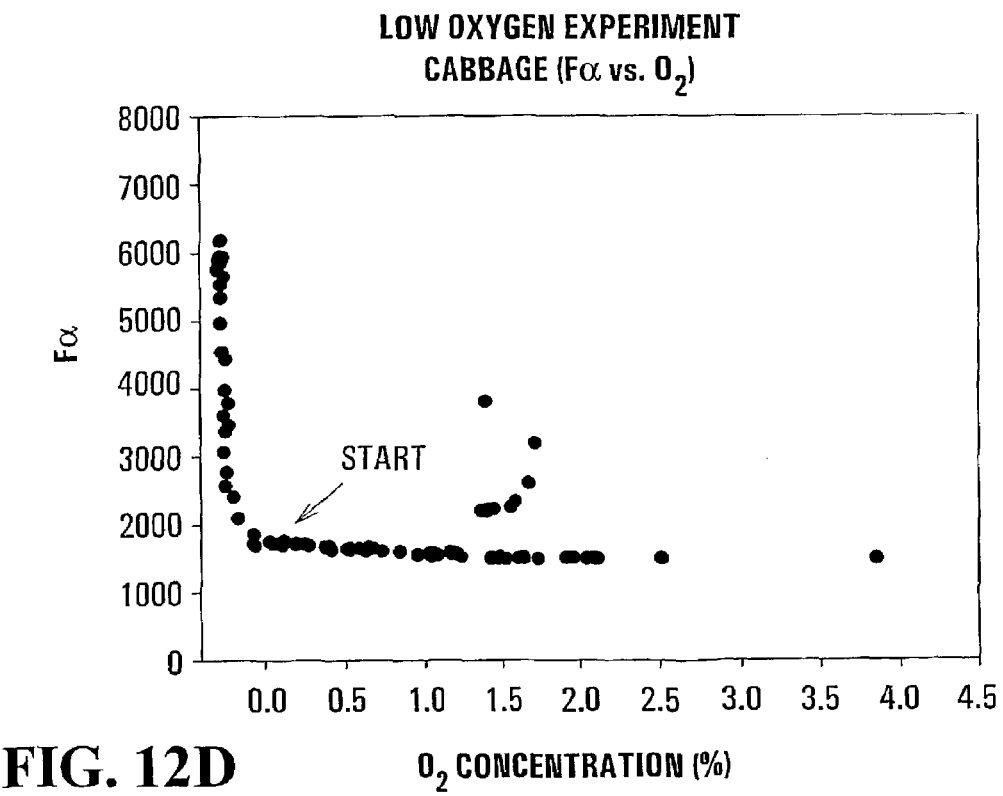
Figure 13A:
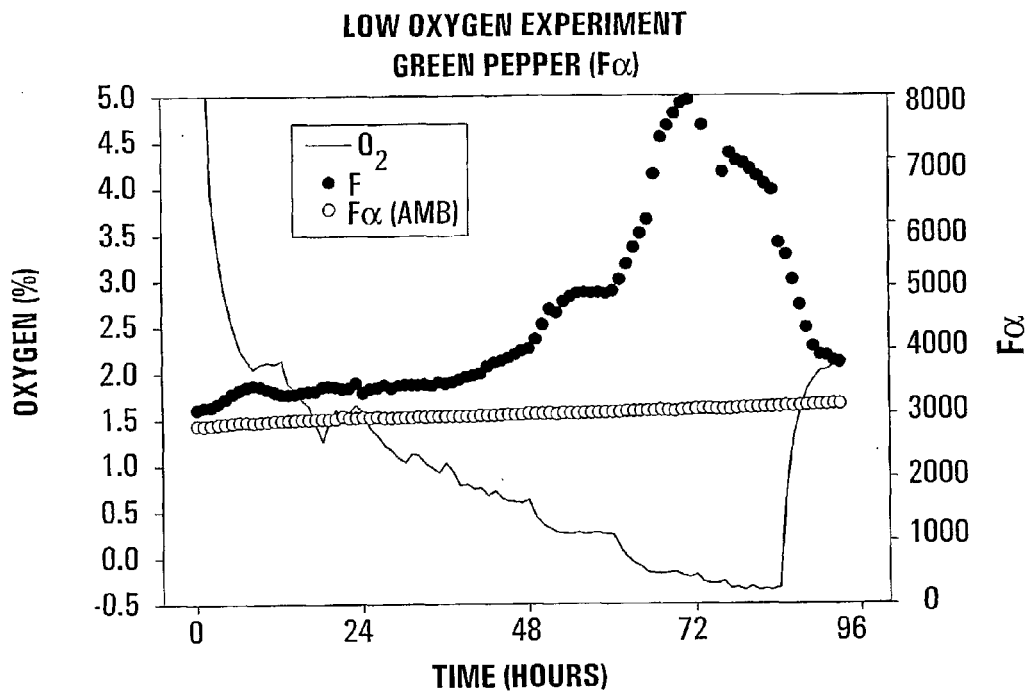
FIGS. 13A to 13D show examples of measurements of low oxygen stress in green pepper samples.
Figure 13B:
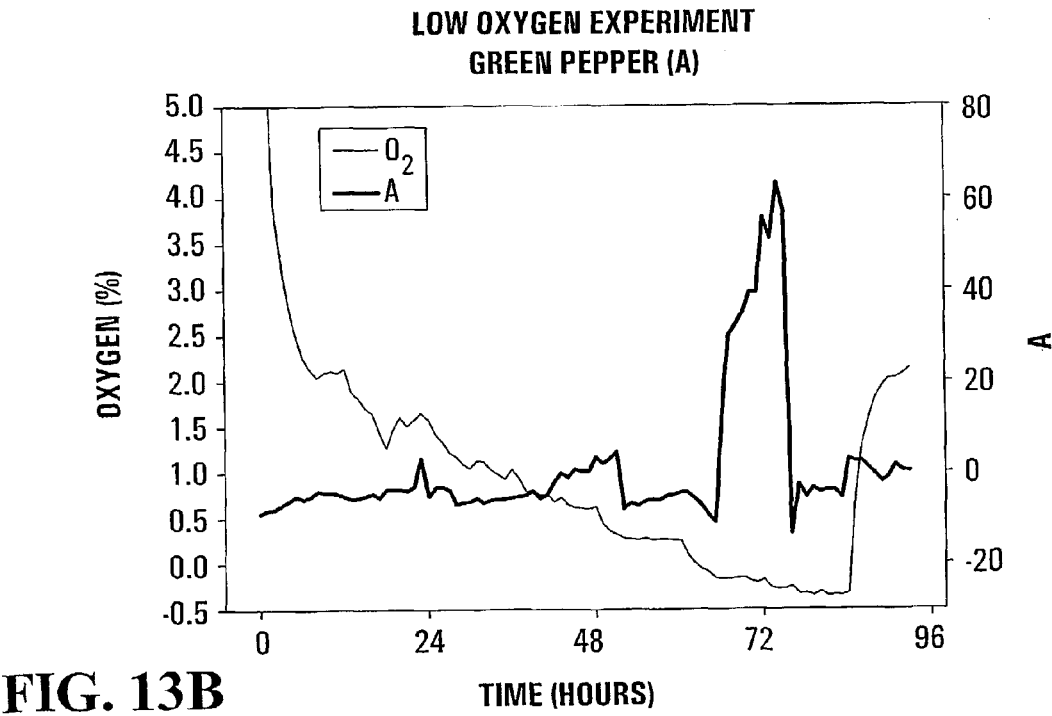
Figure 13C:
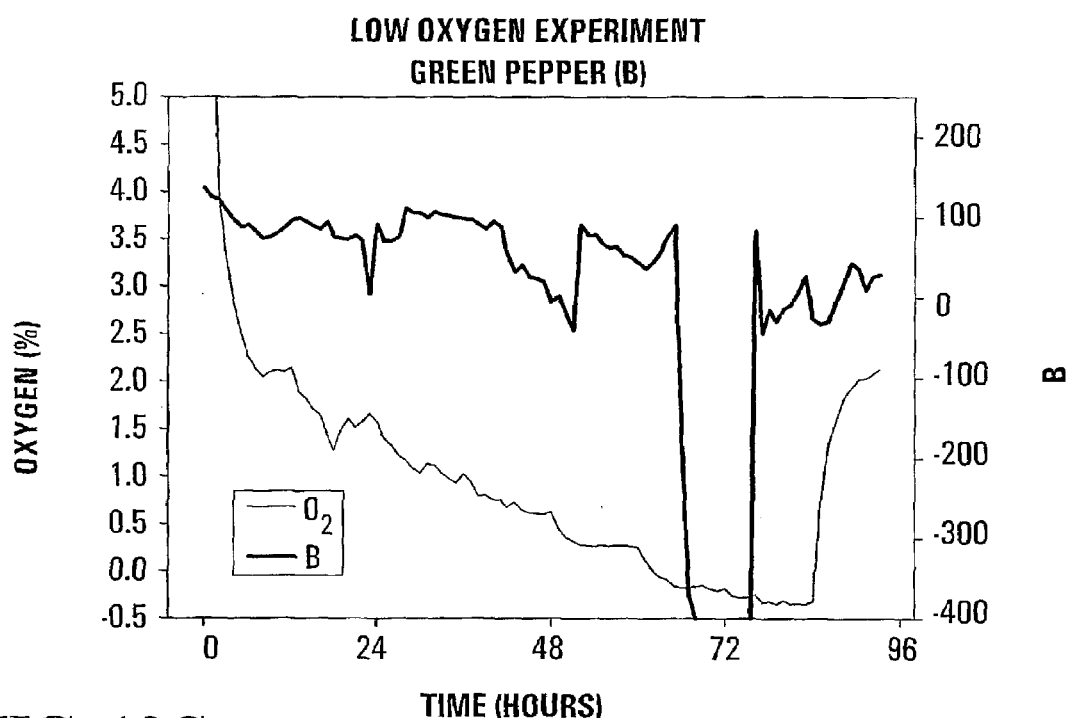
Figure 13D:
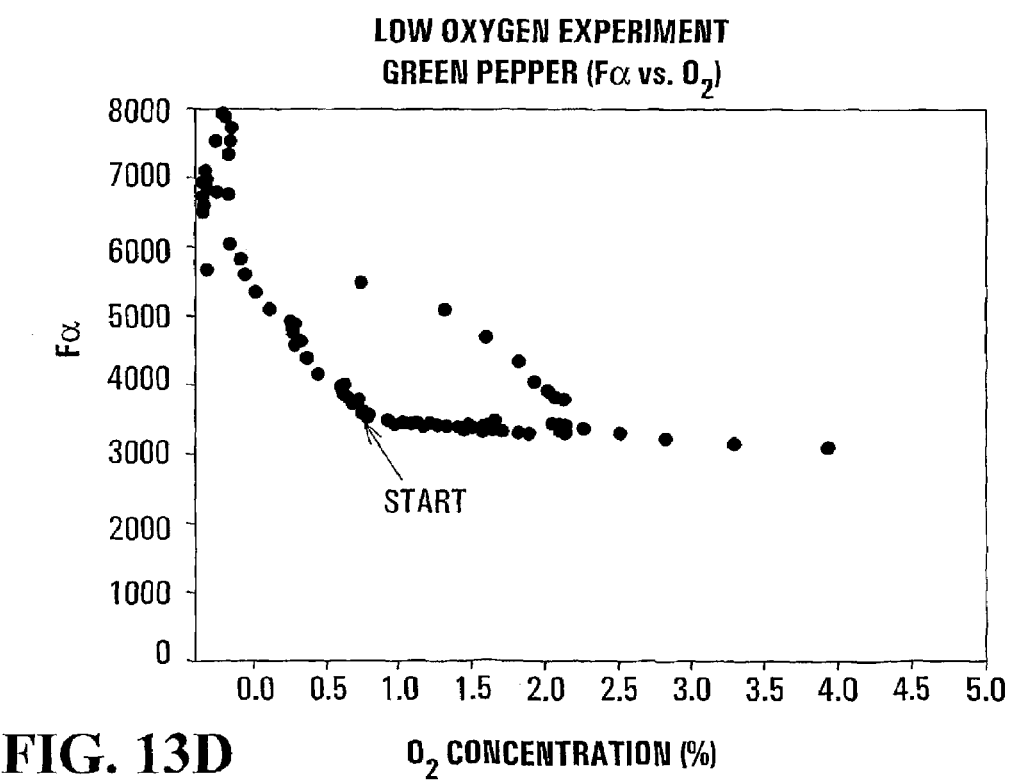
Figure 14A:
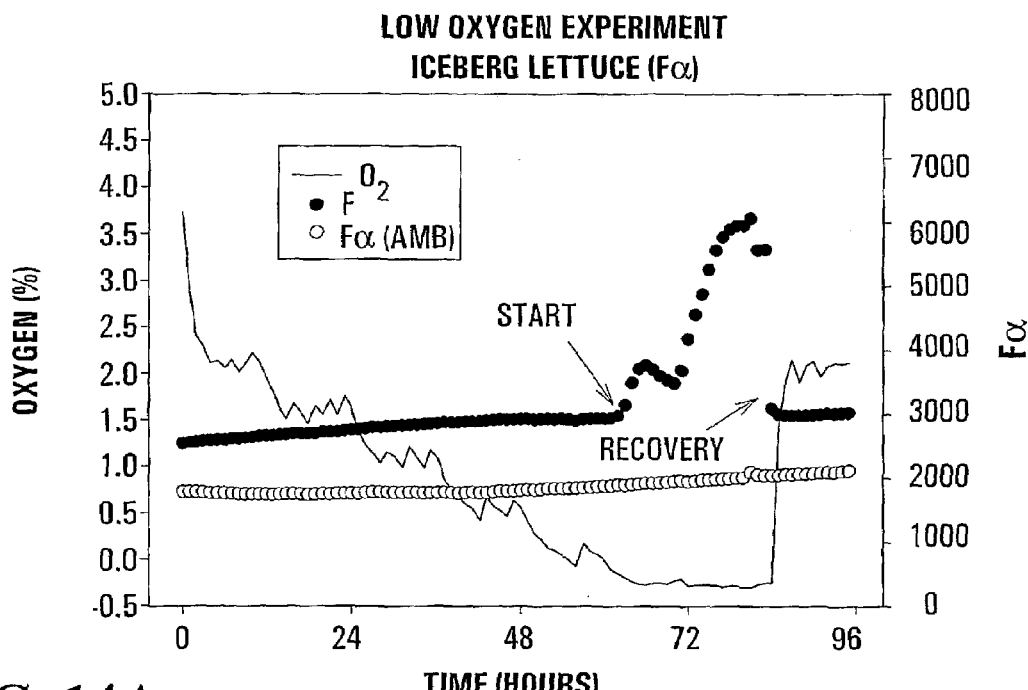
FIGS. 14A to 14D show examples of measurements of low oxygen stress in iceberg lettuce samples.
Figure 14B:
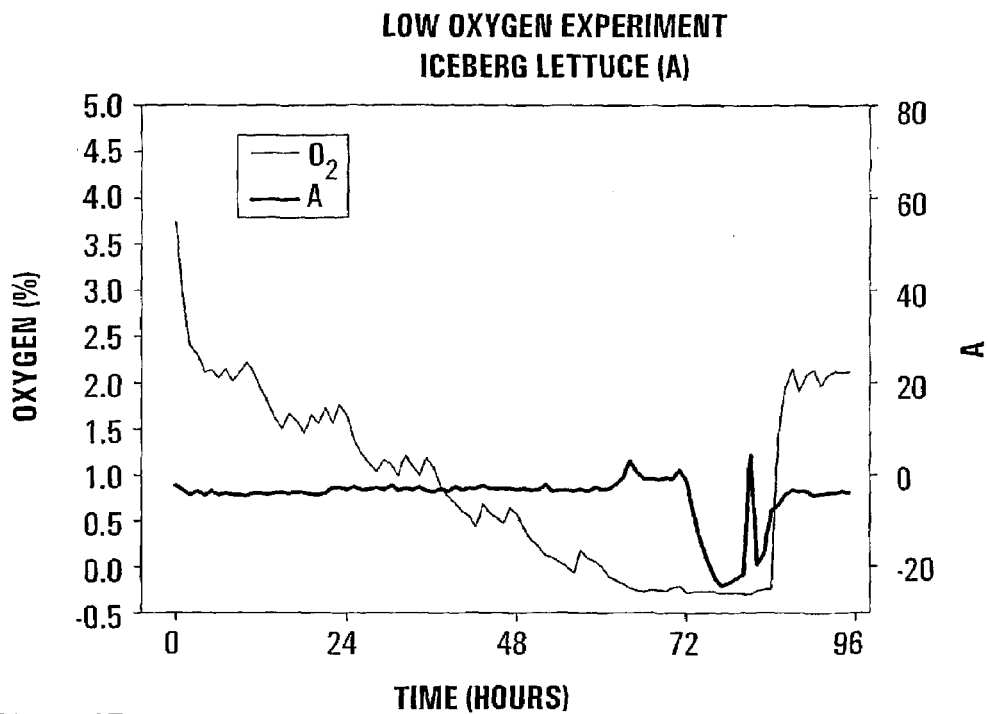
Figure 14C:
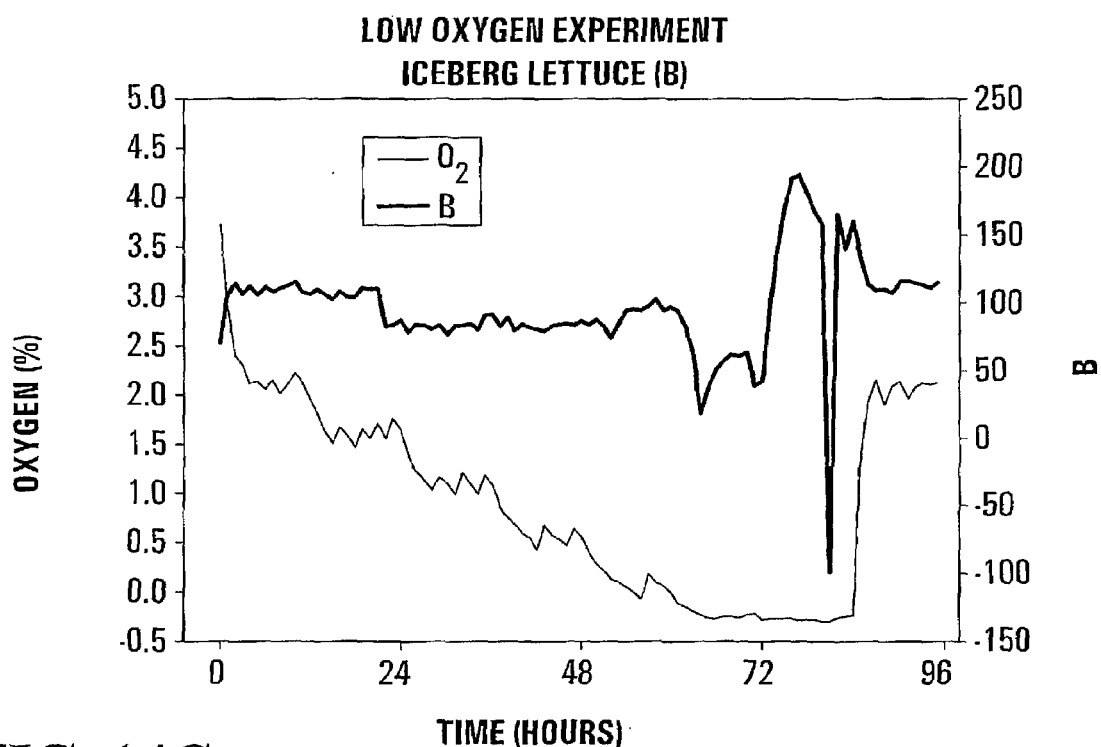
Figure 14D:
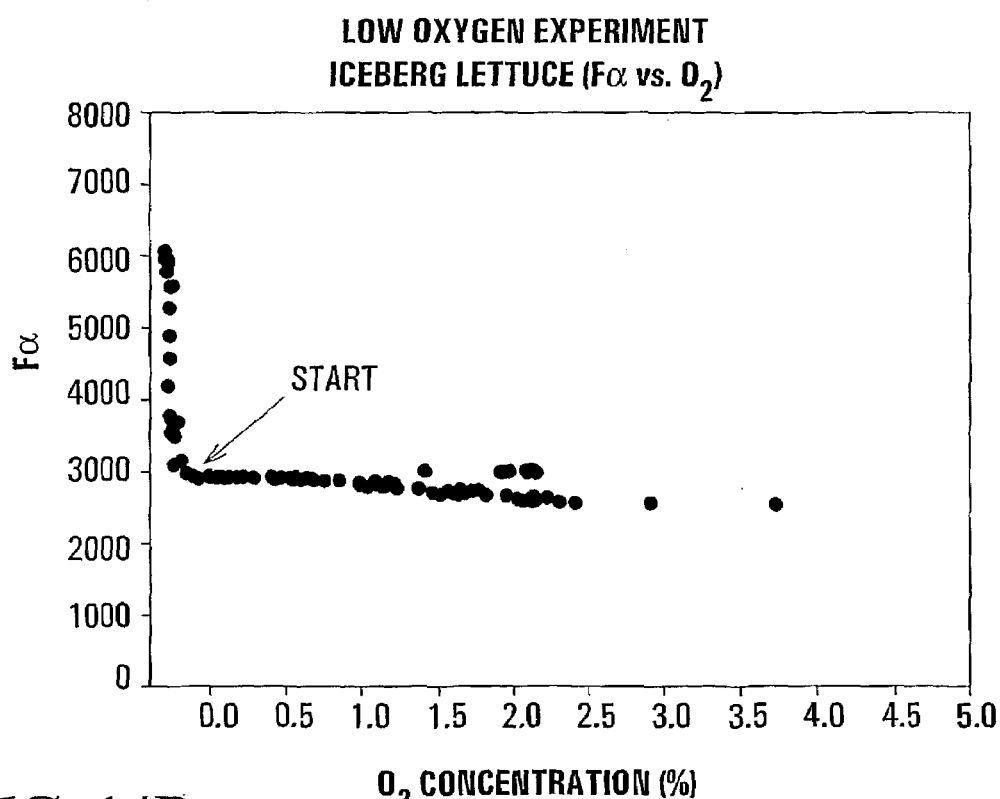

FIG. 11A particularly illustrates the sensitivity of $F_\alpha$ to small fluctuations in the oxygen concentration. Between the time period of hours 24 to 41, the oxygen concentration is switched hourly up and down by about 0.2% between 1.1 and 0.9%, as shown. At these oxygen concentrations, $F_\alpha$ responds by increasing as the oxygen concentration is reduced and decreasing as the oxygen concentration is increased. At oxygen concentrations below the low oxygen stress threshold, the oxygen concentration is occasionally increased during its gradual decrease to 0%. Each time the oxygen concentration is increased, $F_\alpha$ exhibits a corresponding decrease.

FIG. 11A shows that the value of $F_\alpha$ for the control sample gradually decreases as the pear samples ripen over the test period and indicates a loss of chlorophyll. Over the same period, the pear samples were observed to change color from green to yellow.

Monitoring Health in Vegetable Varieties at Low Oxygen Concentrations

The following examples illustrate how embodiments of the present invention can be used to detect the onset of low oxygen stress in vegetable varieties, and for each test, a similar methodology was used as described above for the fruit varieties.

For each vegetable variety, samples of the vegetable were placed in each of two containers. The vegetable samples in one of the containers served as control samples and samples in the other container served as the treatments samples. The containers for the control samples were left open, whereas the treatment containers were sealed and connected to a system which controls and monitors the oxygen levels within the container. A cross-sectional view or a typical treatment container is shown in FIG. 2 and contains a stress monitoring device as described above in connection with FIG. 1. The oxygen concentration was initially lowered to 3% and thereafter the oxygen concentration was reduced to 0% at a rate of 0.5% every 12 hours. Thereafter, the oxygen concentration was reestablished at 3%. This process created a gradual decrease in the oxygen concentration, ensuring that the vegetable samples were subjected to a dangerous oxygen level for their health, followed by a recovery to a healthy oxygen level. For each vegetable variety, the temperature was maintained at approximately 20° C. and $CO_2$ concentrations within the treatment containers were maintained at between 0 and 0.5% by placing small bags of hydrated lime in the containers which absorbed any $CO_2$ produced by the respiration of the vegetables.

EXAMPLE 7

Low Oxygen Stress in Cabbage

FIGS. 12A to 12D show examples of the measured fluorescence response of cabbage samples as the oxygen concentration is progressively reduced. Progressing from higher to lower oxygen concentrations, each of parameters $F_\alpha$, A and B exhibit little change until approximately hour 57 corresponding to an oxygen concentration of about 0.2%. At this oxygen concentration, $F_\alpha$ and parameter A increase abruptly, whereas parameter B exhibits a sharp decrease. $F_\alpha$ continues to increase rapidly as the oxygen concentration is reduced to 0%. Parameter A continues to generally increase and parameter B generally continues to decrease as the oxygen concentration is reduced to 0%. When the oxygen concentration is rapidly re-established to above 1.5%, $F_\alpha$ rapidly decreases to a value slightly above its former value just prior to the onset of low oxygen stress. At a time prior to the re-establishment of the oxygen concentration, parameter A decreases and parameter B increases to approximately their former values just prior to the onset of low oxygen stress.

EXAMPLE 8

Low Oxygen Stress in Green Pepper

FIGS. 13A to 13D show examples of the measured fluorescence response of green pepper samples as the oxygen concentration is varied. Progressing from higher to lower oxygen concentrations, parameters $F_\alpha$ and A initially exhibit a gradual increase, whereas parameter B shows a gradual decrease.

At approximately hour 40, corresponding to an oxygen concentration of about 0.8%, the positive change in both $F_\alpha$ and parameter A increases and parameter B abruptly decreases. $F_\alpha$ continues to increase as the oxygen concentration is lowered to just above 0% at approximately hour 72. Within the same interval, parameter A exhibits a marked increase and parameter B shows a marked decrease. After hour 72, with continued reduction of the oxygen concentration to 0%, $F_\alpha$ and parameter A both decrease to approximately to their former values prior to the onset of low oxygen stress and parameter B rapidly increases, again to its former value prior to the onset of low oxygen stress.

Significant deterioration of the green pepper samples had occurred during the test period and this may account for the decrease in Fα and parameter A and the increase in parameter B prior to the re-establishment of a healthy oxygen concentration.

EXAMPLE 9

Low Oxygen Stress in Iceberg Lettuce

FIGS. 14A to 14D show examples of the measured fluorescence response of iceberg lettuce samples as the oxygen concentration is progressively reduced. Initially, $F_\alpha$ gradually increases as the oxygen concentration is reduced until approximately hour 62 corresponding to an oxygen concentration of just above 0% at which point the positive change in $F_\alpha$ exhibits a marked increase. Initially, parameters A and B remain relatively constant as the oxygen concentration is reduced again until about hour 62, where parameter A exhibits an abrupt increase and parameter B exhibits a marked decrease, indicating the onset of low oxygen stress. $F_\alpha$ generally continues to increase until the oxygen concentration reaches 0%. When the oxygen concentration is rapidly reestablished to a value above the onset of low oxygen stress, $F_\alpha$ rapidly decreases to approximately its value prior to the onset of low oxygen stress, indicating recovery of the iceberg lettuce sample from low oxygen stress.

EXAMPLE 10

Low Oxygen Stress in Romaine Lettuce

Figure 15A:
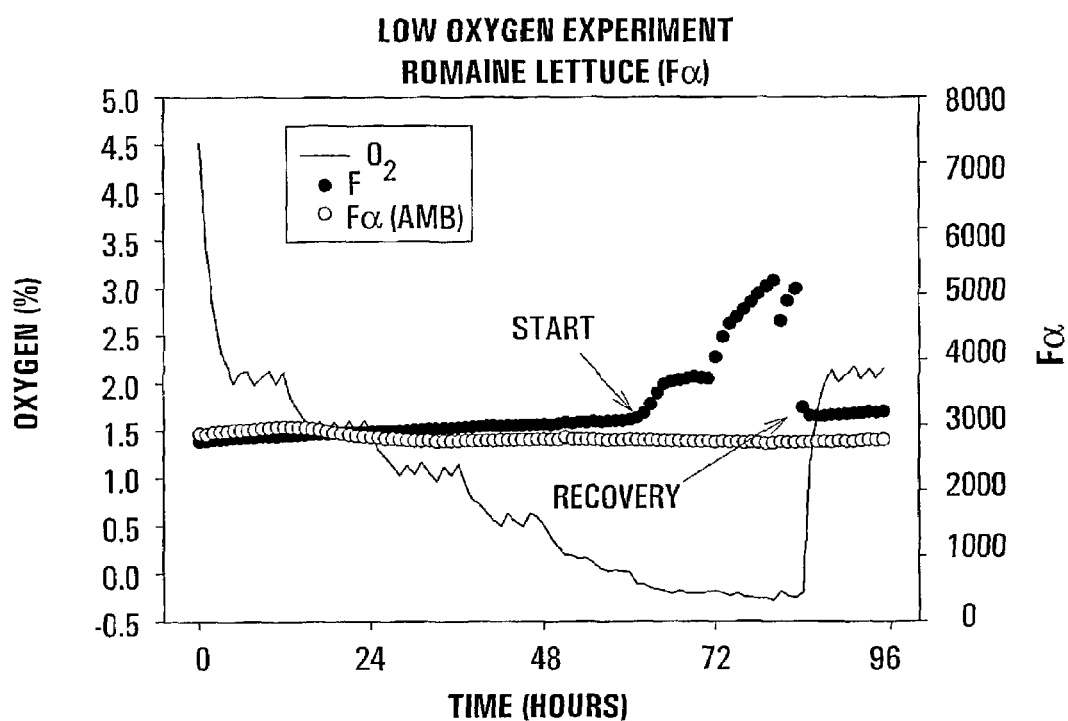
FIGS. 15A to 15D show examples of measurements of low oxygen stress in romaine lettuce samples.
Figure 15B:
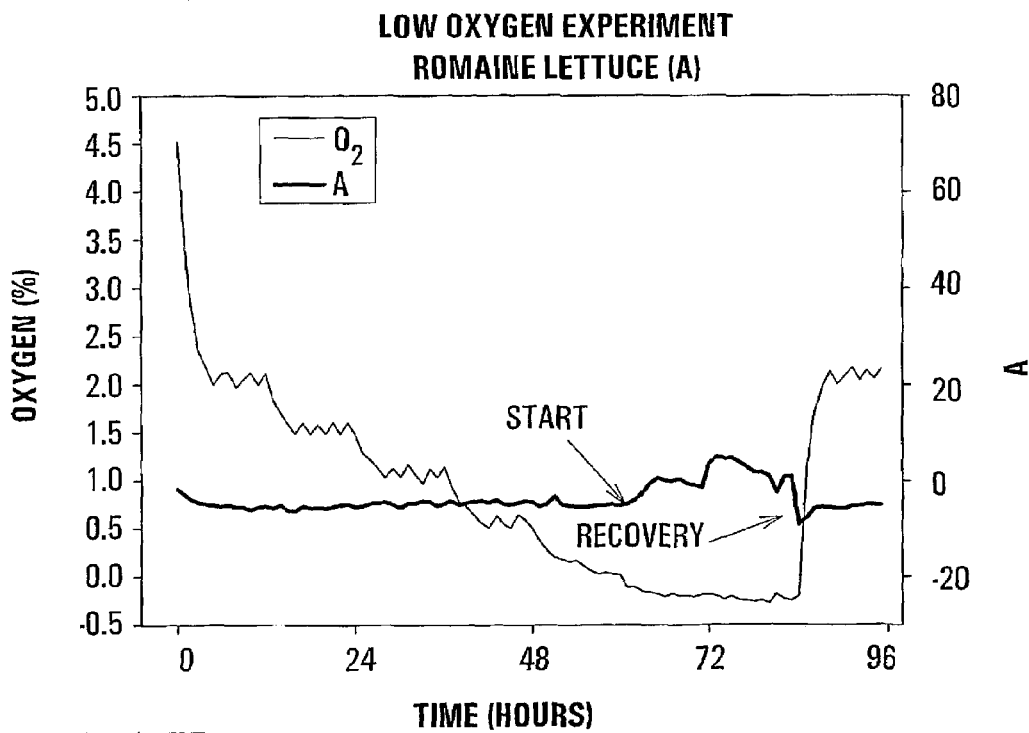
Figure 15C:
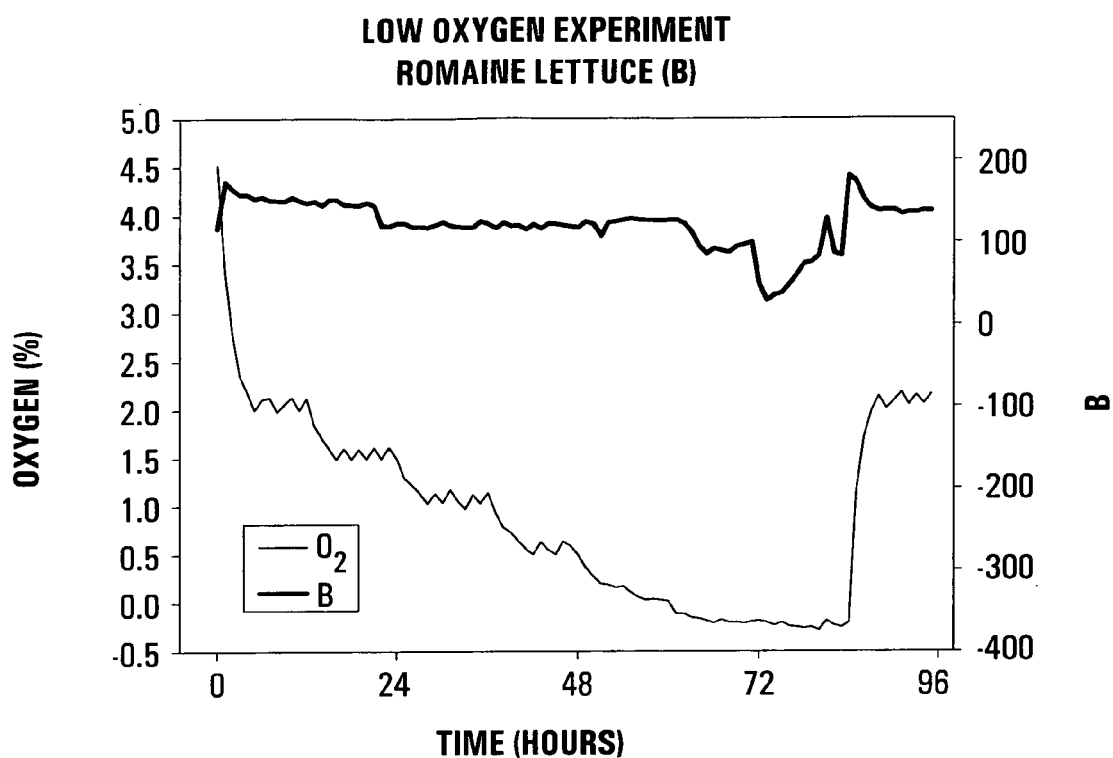
Figure 15D:
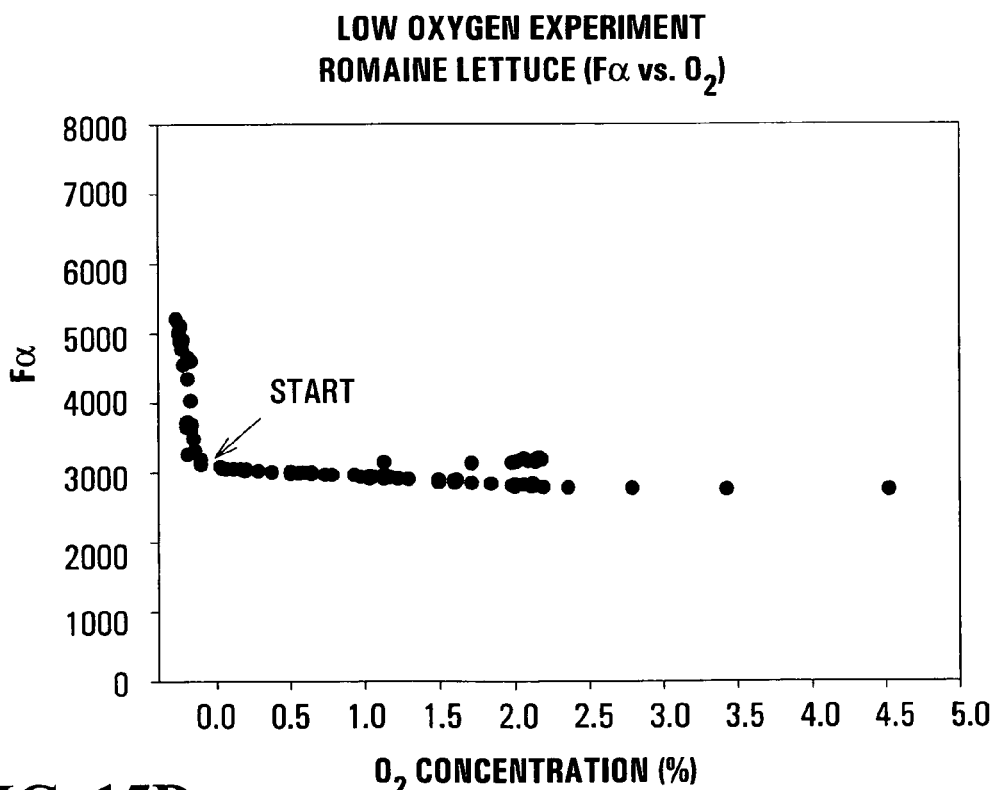

FIGS. 15A to 15D show examples of the measured fluorescence response of romaine lettuce as the oxygen concentration is progressively reduced. Initially, $F_\alpha$ and parameter A exhibit a small gradual increase as the oxygen concentration is lowered until approximately hour 60 corresponding to an oxygen concentration of just above 0%. Over the same period, parameter B exhibits a small gradual decrease. At approximately hour 60, the positive change in both $F_\alpha$ and parameter A exhibit a marked increase indicating the onset of low oxygen stress, and parameter B exhibits an abrupt decrease, again indicating the onset of low oxygen stress. As the oxygen concentration is reduced further to 0%, $F_\alpha$ continues its relatively rapid increase, parameter A continues generally to increase and parameter B continues generally to decrease. When the oxygen concentration is again re-established to a healthy level at approximately hour 84, $F_\alpha$ rapidly decreases to approximately its former value prior to the onset of low oxygen stress indicating recovery of the romaine lettuce sample from low oxygen stress and parameters A and B exhibit a marked decrease and increase, respectively towards their former values prior to the onset of low oxygen stress, again indicating recovery of the romaine lettuce samples from low oxygen stress. As shown in FIG. 15A, the value of $F_\alpha$ of the control sample remains relatively constant over the test period.

Monitoring Health in Chlorophyll Containing Matter in Response to High Carbon Dioxide Concentrations The following example illustrates how embodiments of the present invention can be used to detect the onset of high $CO_2$ stress in chlorophyll containing matter. In the example, the fluorescence response of cabbage samples was measured with varying $CO_2$ levels for two different oxygen concentrations.

The apparatus for monitoring high $CO_2$ stress in this example is the same as that used to monitor low oxygen stress in various fruit and vegetable varieties, described above. Cabbage samples to be treated with high $CO_2$ levels were placed in sealed containers connected to an atmosphere control system for controlling the various levels of nitrogen, oxygen and carbon dioxide. Control samples were also placed in containers and maintained at ambient conditions. $CO_2$ concentrations in the treatment containers initially started at 0% and were increased by 2% every 12 hours until the concentration had risen to 12%. The $CO_2$ concentration was then lowered back to 0%. The temperature was maintained at approximately 20° C. over the test period.

EXAMPLE 11

High $CO_2$ Stress in Cabbage

FIGS. 16A to 16E show examples of the measured fluorescence response of cabbage samples with varying $CO_2$ concentrations. The test shown in FIG. 16A was performed at an oxygen concentration of 4% and the test shown in FIGS. 16B to 16E was performed at an oxygen concentration of 1.5%.

Figure 16A:
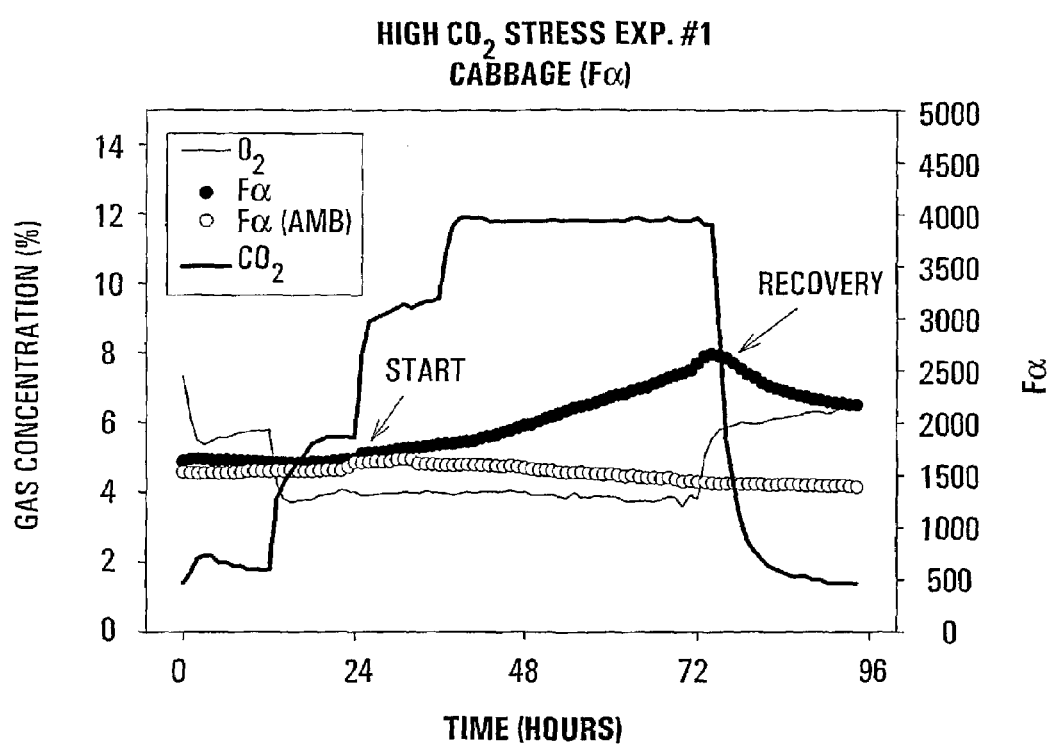
FIGS. 16A to 16E show examples of measurements of high carbon dioxide stress in cabbage samples.

FIG. 16A shows the response of $F_\alpha$ as the $CO_2$ level is varied, together with $F_\alpha$ for the control sample. Initially, as the carbon dioxide level is increased, $F_\alpha$ of the treatment sample remains relatively constant until approximately hour 24 when the $CO_2$ concentration is increased from about 5.5% to about 9%. At the same time, $F_\alpha$ exhibits a noticeable increase, indicating the onset of high $CO_2$ stress in the cabbage sample. Shortly after hour 24, the $CO_2$ concentration increases more slowly to about hour 36 and $F_\alpha$ steadily increases over the same period. At hour 36, the carbon dioxide concentration is again rapidly increased from just below 10% to 12% and is maintained at this level until about hour 72. Shortly after this abrupt increase in carbon dioxide level, $F_\alpha$ increases at a faster rate, indicating that the cabbage samples are experiencing increasing stress as the carbon dioxide levels are increased further. $F_\alpha$ continues to increase at this new accelerated rate over the period at which the $CO_2$ level is held at 12%.

At hour 72, the $CO_2$ concentration is rapidly reduced to 0% and at the same time $F_\alpha$ decreases, indicating recovery of the cabbage samples from $CO_2$ stress. It is observed that the value of $F_\alpha$ does not return to its former value just prior to the onset of high $CO_2$ stress during the 24 hour period following the rapid return of the $CO_2$ concentration to 0%, which may indicate that permanent physiological change has occurred within the cabbage samples. The value of $F_\alpha$ for the control sample varies very little over the test period. Parameters A and B which were measured for the treatment sample over the test period were relatively stable and showed little change in response to the varying $CO_2$ concentration.

Figure 16B:
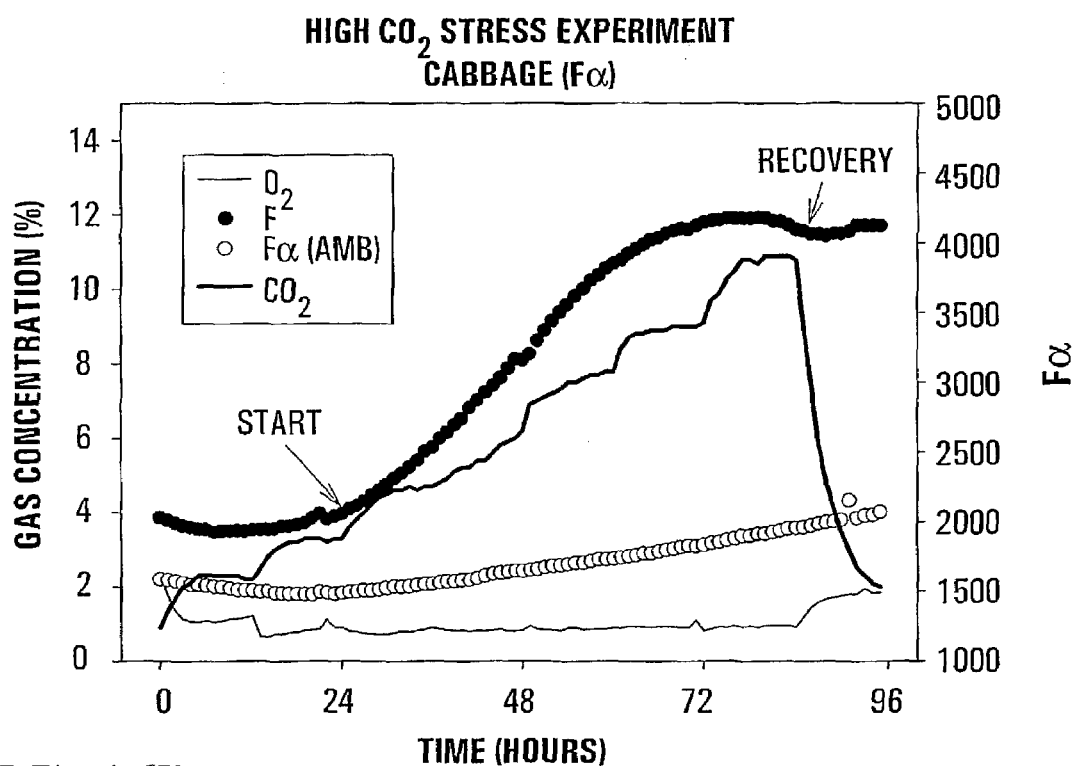

FIG. 16B shows the variation of $F_\alpha$ with $CO_2$ concentration at an oxygen concentration of about 1.5%, together with the variation of $F_\alpha$ for the control sample. As the carbon dioxide level is increased from 0%, $F_\alpha$ initially changes very little, first making a small decrease and then a very gradual increase until about hour 24 corresponding to a carbon dioxide level of about 3%. As the carbon dioxide level is increased above about 3%, the positive change in $F_\alpha$ increases, indicating the onset of high carbon dioxide stress. $F_\alpha$ continues to increase at approximately the same rate with increasing carbon dioxide concentration until about hour 60 and thereafter begins to level off. For this sample, the onset of high carbon dioxide stress occurred at a lower carbon dioxide concentration than for the sample shown in FIG. 16A which may be attributed to differences in the samples tested or to an increase sensitivity to high carbon dioxide concentrations at lower oxygen levels.

The carbon dioxide level is reduced relatively quickly from about hour 84 and it is observed that $F_\alpha$ begins to decrease before the carbon dioxide level is reduced. In comparison to the sample test results shown in FIG. 16A, the cabbage samples of FIG. 16B are held in relatively high carbon dioxide concentrations over a longer period of time and the relatively small decrease in $F_\alpha$ towards the end of the test may indicate that the cabbage sample has sustained permanent physiological change.

Figure 16C:
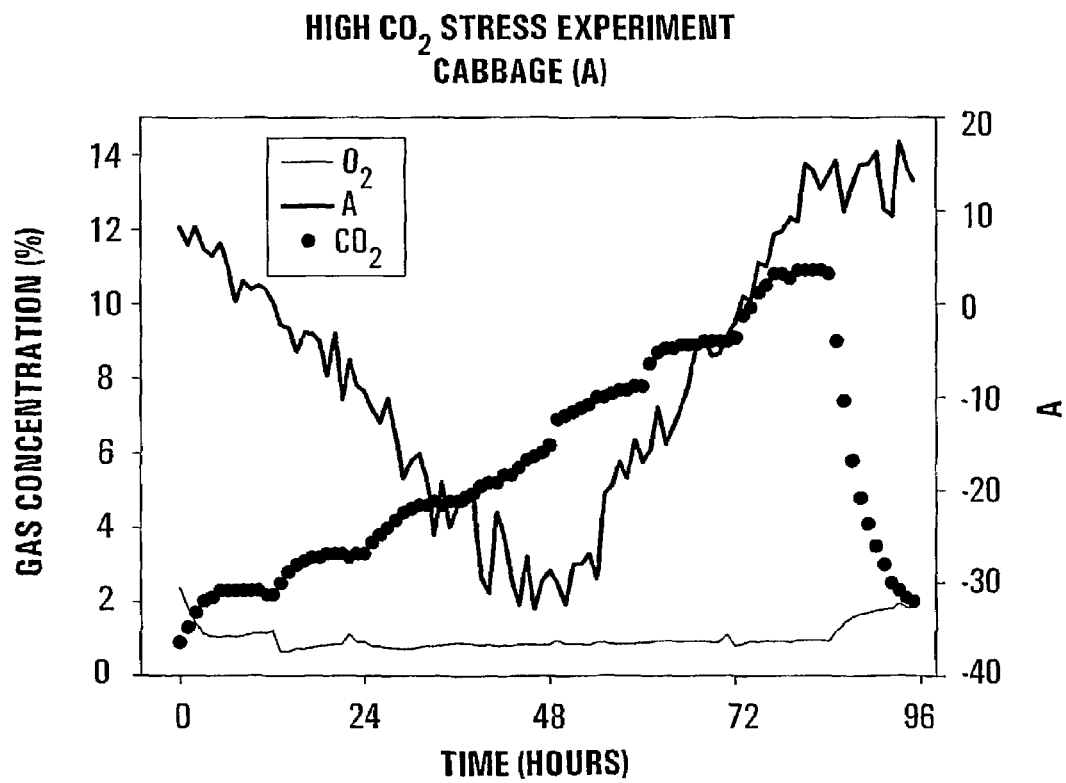
Figure 16D:
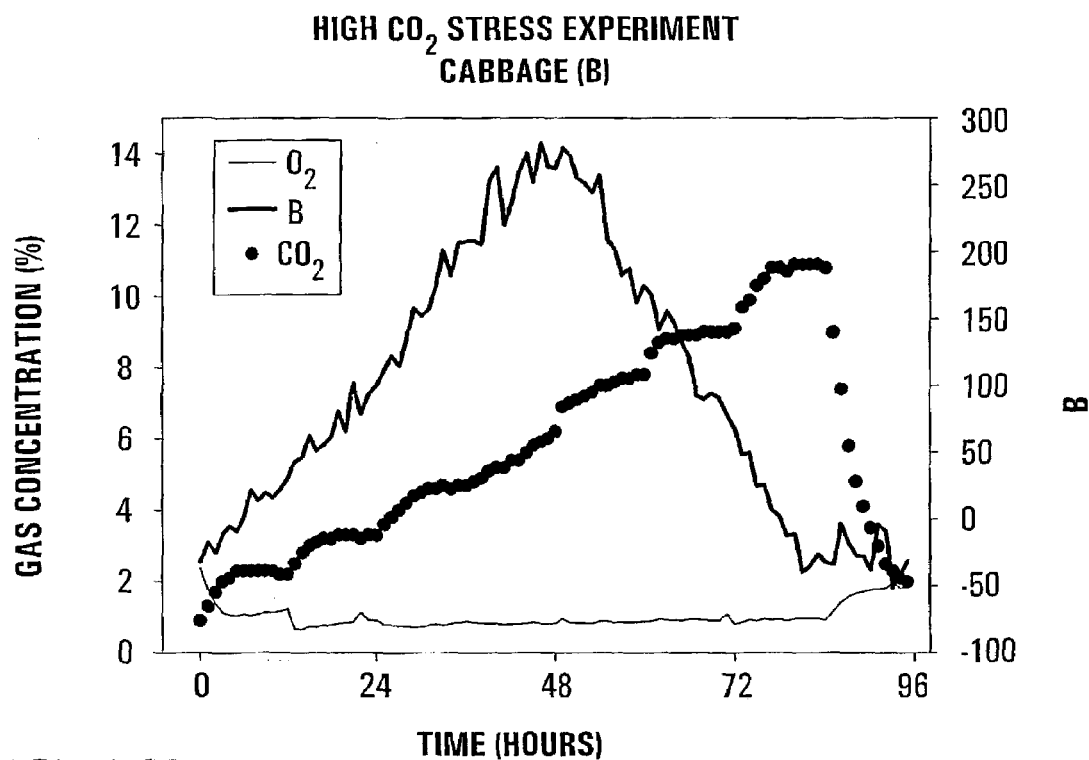
Figure 16E:
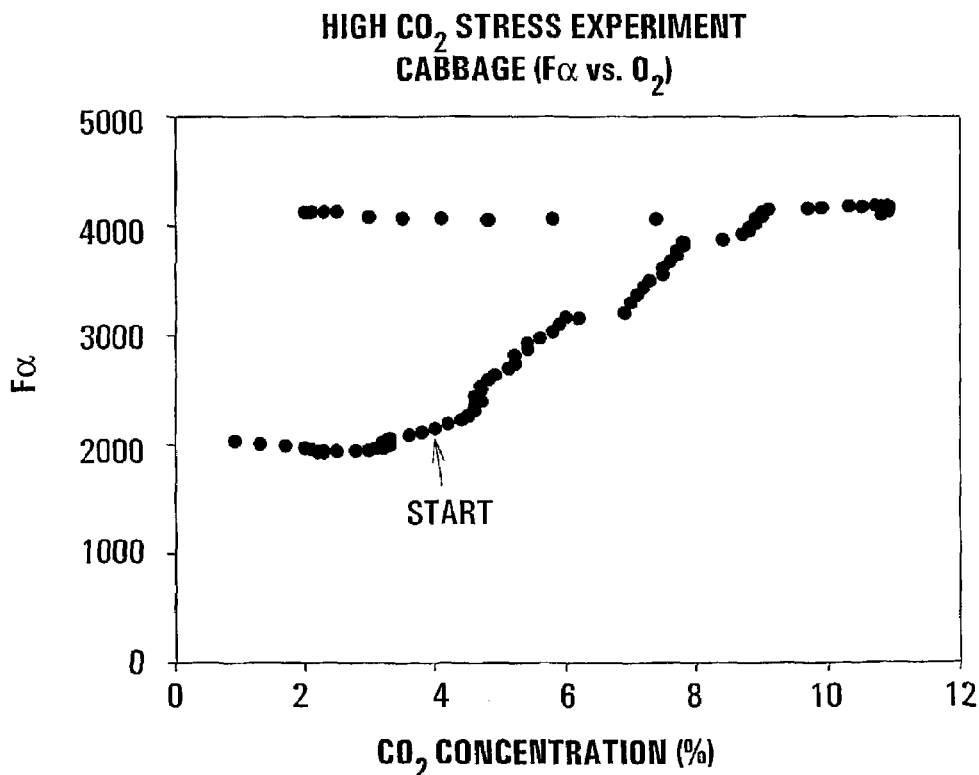

Referring to FIGS. 16C and 16D, parameter A steadily decreases as the carbon dioxide concentration is increased whereas parameter B steadily increases and at a carbon dioxide concentration of about 7%, parameter A passes through a minimum and thereafter gradually increases as the carbon dioxide concentration continues to increase and at the same carbon dioxide concentration (about 7%) parameter B passes through a maximum and thereafter gradually decreases with increasing carbon dioxide concentration. Thus, in addition to $F_\alpha$, parameters A and B are both sensitive to $CO_2$ levels at lower oxygen concentrations and can be used to detect the presence of $CO_2$ and/or to provide an indication of the level of $CO_2$ and may be used to provide a warning of when $CO_2$ levels exceed concentrations for a healthy environment.

Detecting the Reaction of Chlorophyll Containing Matter to Temperature Changes

The following example illustrates how embodiments of the present invention can be used to detect how chlorophyll containing matter responds to temperature changes. In this example, chlorophyll fluorescence monitoring devices as described above and shown in FIG. 1 were used to monitor the fluorescence response of unripened banana samples as the temperature of the room in which the samples were stored was varied. The banana samples which each consisted of a cluster of three bananas were placed in fruit kennels and their fluorescence response was monitored hourly as the room temperature was lowered from 15° to 3° in 3° increments every 24 hours. The fluorescence response of a control sample of bananas was also monitored using a fluorescence monitoring device as shown in FIG. 1 in a room at 22° C.

EXAMPLE 12

Monitoring Temperature Response in Banana Samples

Figure 17A:
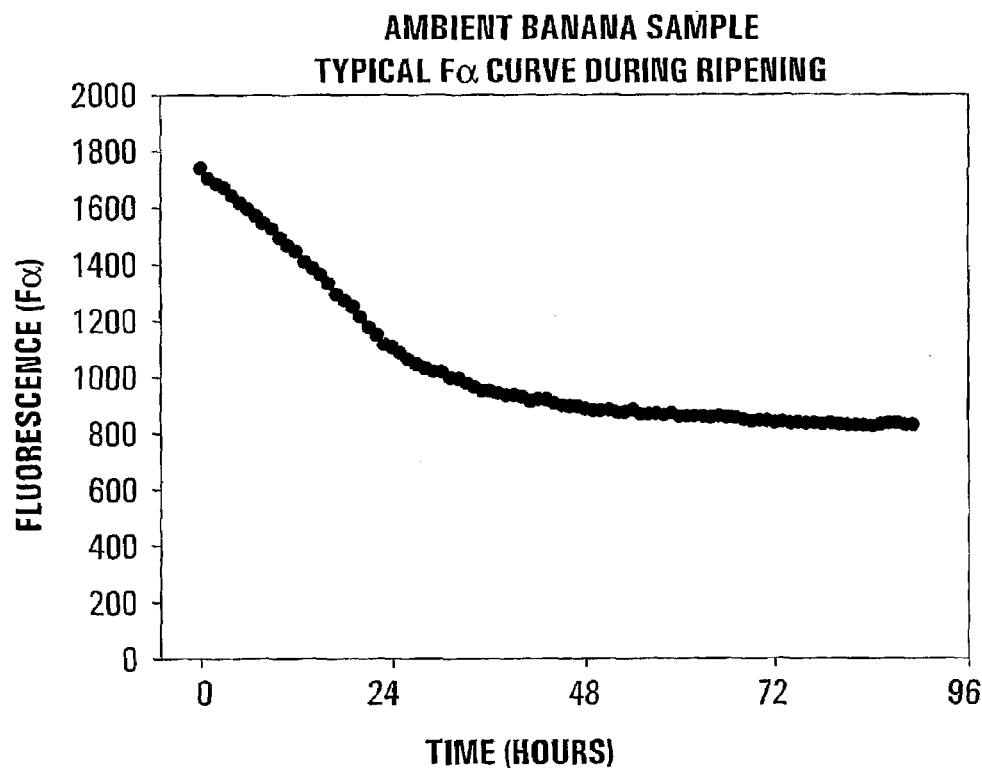
FIGS. 17A to 17C show examples of measurements of low temperature stress in banana samples.

FIG. 17A shows a graph of Fα as a function of time of a banana sample held in ambient atmosphere at 22° C. Over the first 24 hour period, $F_\alpha$ is seen to decrease relatively rapidly and then decrease more slowly over the following 2½ days. This decline in $F_\alpha$ over the test period results from the banana ripening and losing chlorophyll as the banana sample turns from green to yellow at the end of the test period when the banana sample is fully ripened. Thus, embodiments of the present invention may be used to detect the loss of chlorophyll in chlorophyll containing produce, for example as the produce ripens. In further embodiments of the present invention, the detection of loss of chlorophyll resulting, for example in ripening of a stored product may be used to control one or more environmental parameters to reduce the loss of chlorophyll or the rate of loss of chlorophyll and slow the ripening of the produce.

Figure 17B:
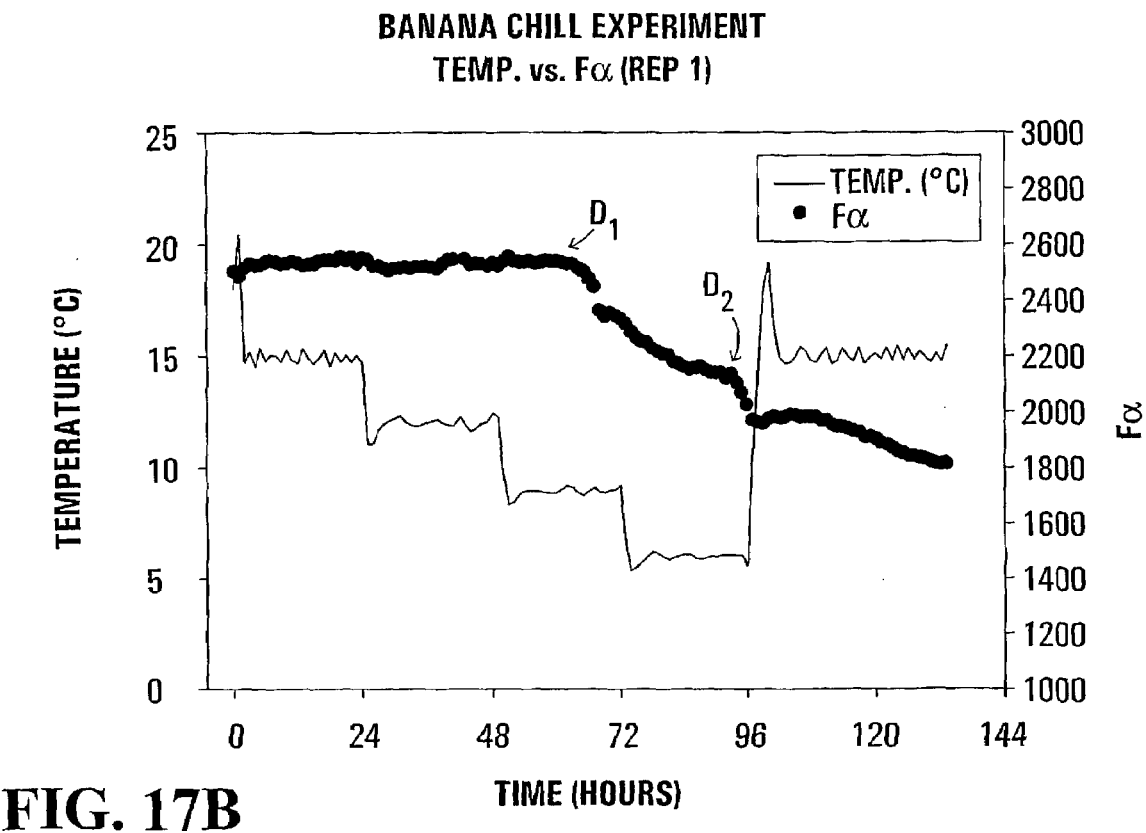

FIG. 17B shows the variation of $F_\alpha$ with temperature as the temperature is lowered incrementally from 15° C. to 6° C. over a four day period and is then returned to 15° C. for a further 24 hour period. $F_\alpha$ remains relatively constant during the first and second 24 hour periods at temperatures of 15 and 12° C., respectively. At about hour 60 during the third 24 hour period at a temperature of 9° C., $F_\alpha$ begins to decrease as indicated at $D_1$. $F_\alpha$ continues to decrease over the next 24 hour period and at about hour 90 during the fourth 24 hour period at a lower temperature at 6° C., $F_\alpha$ decreases at a higher rate, as indicated at $D_2$. $F_\alpha$ continues to decrease at this higher rate until the temperature is quickly increased to above 15° C. at hour 96. At this point, the decline in $F_\alpha$ ceases and $F_\alpha$ remains relatively constant over the next 12 hour period at a temperature of 15° C. before decreasing again at the same temperature The particular banana samples used in this test remained green over the five day test period and beyond but ripened eventually.

The results indicate that Fα can be used to detect the response of chlorophyll containing produce to both decreasing and increasing temperatures. Although the previous results show that the onset of stress in chlorophyll containing produce due to changes in environmental parameters such as oxygen and carbon dioxide concentrations is signified by an increase in Fα, the processes which define the fluorescence response of chlorophyll due to temperature changes are likely to be different and therefore invoke a different response in Fα. Thus, Fα can be used to monitor temperature-induced reactions in chlorophyll containing produce and may be used to monitor independently temperature changes in the environment in which the produce is stored and may further be used to control the temperature of the environment.

Figure 17C:
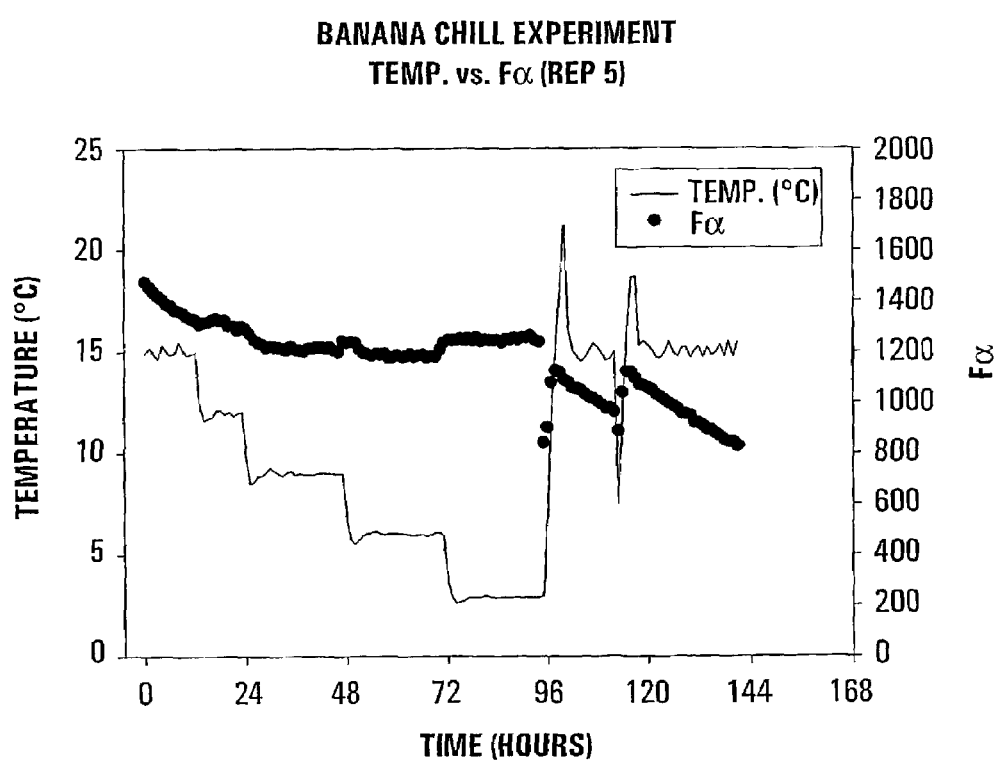

FIG. 17C shows the variation of Fα with temperature for a different banana sample. Over the first 12 hour period at a temperature of 15° C., Fα decreases slightly as the temperature is lowered to 12° C. before decreasing again to a value which remains relatively constant over the next three 24 hour periods until hour 96 when the temperature is quickly raised from 3° C. to about 20°0 C. As the temperature is rapidly increased, Fα rapidly decreases and then increases again to a value below its previous value and thereafter decreases steadily as the temperature is held at about 15° C. Thus, Fα can detect the response of chlorophyll containing produce to thermal shock. At about hour 110, the temperature rapidly fluctuates, initially decreasing to about 7° C. then increasing to about 17° C. and finally settling again at about 15° C. Again, Fα responds to this rapid temperature fluctuation by first decreasing and then rapidly increasing within the same time period as the temperature fluctuation before resuming a gradual decline when the temperature returns to 15° C. Thus, Fα may be used to detect sudden temperature changes of the environment in which chlorophyll containing matter is stored. Detection of such an event may be used to warn an operator or control system so that any appropriate action can be taken.

Monitoring Moisture Stress in Chlorophyll Containing Matter

The following example illustrates how embodiments of the present invention can be used to detect the onset of stress due to moisture loss in chlorophyll containing matter. In this example, the fluorescence response of the leaves of strawberry plants was monitored as the moisture content of the leaves was lost.

In this example, mature potted strawberry plants which had been maintained in a greenhouse and watered regularly to ensure good plant health were used. Individual plants were transferred from the greenhouse to a laboratory to be monitored by fluorescence monitoring devices. Three fluorescence monitoring devices as described above and shown in FIG. 1 were placed over three individual intact strawberry leaves to monitor each leaf separately. The leaves were taped to a plastic sheet to prevent them from moving and the fluorescence monitoring devices were mounted over each leaf at a distance of 7 cm from the leaf surface.

The fluorescence monitoring devices, sampled the leaf fluorescence every 15 minutes throughout a three day period. After approximately 24 hours of measurements, in order to obtain a baseline reading, two of the three leaves were cut from the strawberry plant. The third leaf was kept intact and at this point the plant was also watered. The stem of one of the cut leaves was placed in a beaker of water to provide additional moisture to keep the leaf properly hydrated. The other cut leaf and its stem were simply exposed to air and received no further water for the remaining two days of the test period. This cut leaf with water addition was used to check if the act of cutting the stems from the plant caused a significant fluorescence change in the leaf samples. After cutting, the fluorescence monitoring devices monitored the samples for an additional two days and after three days the plant was removed and replaced with a new healthy plant from the greenhouse and the process repeated.

EXAMPLE 13

Moisture Stress in Strawberry Plants

Figure 18A:
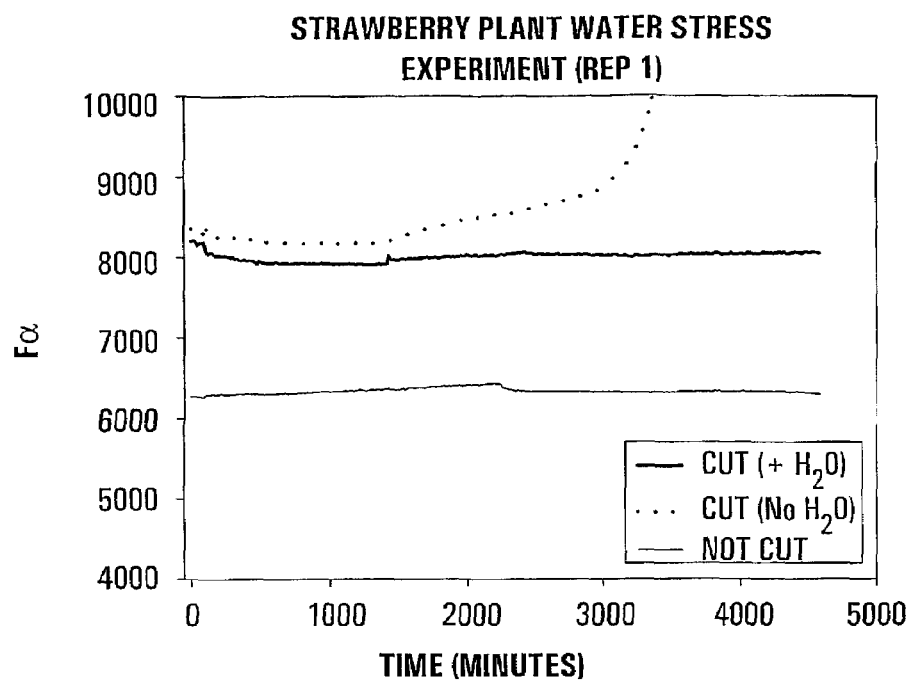
FIGS. 18A and 18B show examples of moisture stress in strawberry plants.
Figure 18B:
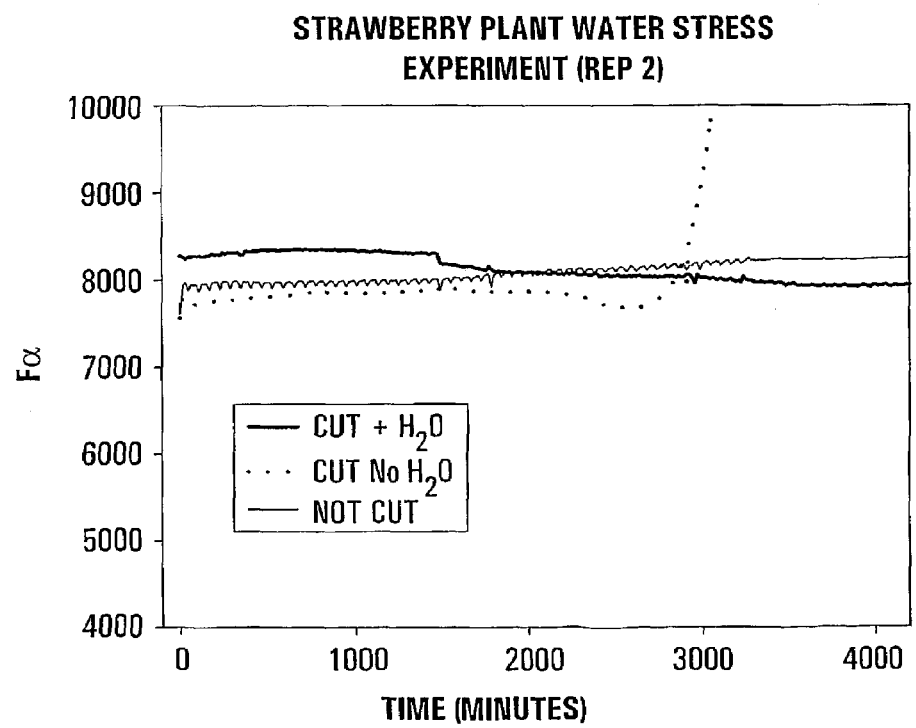

FIGS. 18A and 18B show examples of the fluorescence response of the leaves of two strawberry plants. During the first 24 hour period when none of the monitored leaves were cut, the fluorescence response of all three leaves is relatively stable. $F_\alpha$ for the cut unwatered leaf of the plant of FIG. 18A begins to increase shortly after the leaf is cut indicating the onset of stress due to lack of moisture, and continues to increase at a steady rate over about the next 24 hour period. During the third 24 hour period, i.e. at about 3000 minutes, $F_\alpha$ for the cut unwatered leaf abruptly increases, indicating a more severe increase in moisture loss induced stress. Over the second and third 24 hour periods $F_\alpha$ for the cut, watered leaf and the uncut leaf remain relatively constant.

$F_\alpha$ for the cut, unwatered leaf of the plant of FIG. 18B initially remains relatively constant after the leaf is cut, then decreases slightly during the second 24 hour period and subsequently at about the start of the third 24 hour period increases abruptly indicating the onset of low moisture stress. Over the second and third 24 hour periods, $F_\alpha$ for the cut, watered leaf and the uncut leaf exhibit little change. The visual analysis of the leaves after each test showed that the intact and cut, watered leaves were still healthy but the cut, unwatered leaves had become quite dry. Embodiments of this method of measuring stress due to moisture loss in chlorophyll containing matter using chlorophyll fluorescence may be applied to any suitable plants including both rooted and cut plants and may be used in indoor or outdoor applications for detecting moisture stresses in plant materials. For example, the technique may be used for plants in residential and commercial buildings, greenhouses or in the field.

Embodiments of the stress monitoring method and apparatus may be used to detect the onset of stress or physiological change in any chlorophyll containing matter which exhibits a detectable transition in the change of fluorescence intensity level, or in a parameter derived from the intensity level which is sensitive to stress or physiological change.

The monitoring apparatus and method may be used to monitor the health and well-being of living plants, cultivars, fruits and vegetables so that appropriate action can be taken to maintain a healthy condition. The apparatus and method may be used to provide a warning that an environmental parameter is at an incorrect value and needs to be changed. For example, the apparatus and method could be applied to controlled atmosphere storage to alert an operator that the oxygen concentration is too low or the concentration of carbon dioxide is too high. The apparatus and method can also be applied to determine the optimum environmental conditions for storing fruits and vegetables and/or to dynamically control the environment. Examples of how the apparatus and method may be applied to determine the optimum oxygen concentration for storing fruits and vegetables and/or for controlling the relative gas concentrations in the storage environment will now be described with reference to FIGS. 19 to 31.

Figure 19:
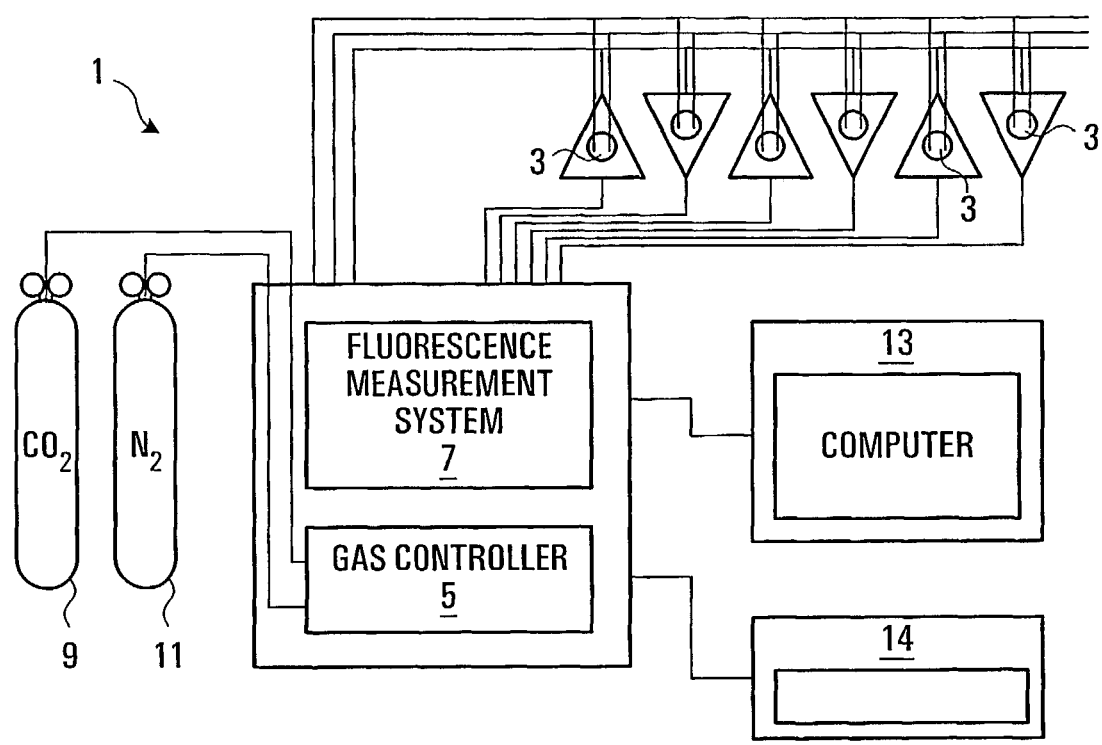
FIG. 19 shows a schematic diagram of a system for performing a method according to an embodiment of the invention.

Referring to FIG. 19, a combined controlled atmosphere and chlorophyll fluorescence measurement system according to an embodiment of the present invention, generally indicated at 1, comprises a plurality of storage jars 3, for containing one or more fruit or vegetable sample, a gas control system 5 for controlling the relative concentrations of different gases contained within each storage jar 3 and a fluorescence measurement system 7 for measuring the level of chlorophyll fluorescence emitted from the fruit or vegetable samples. Gas canisters 9 and 11, serving as sources of carbon dioxide and nitrogen gas, respectively, are connected to the gas control system 5. A computer 13, for example a PC, controls the operation of the gas controller 7 to regulate changes in the concentrations of gases in each storage jar 3, and collects and analyzes data from the fluorescence measurement system 7. The computer 13 may include user interfaces such as a visual display and keyboard 14.

Figure 20:
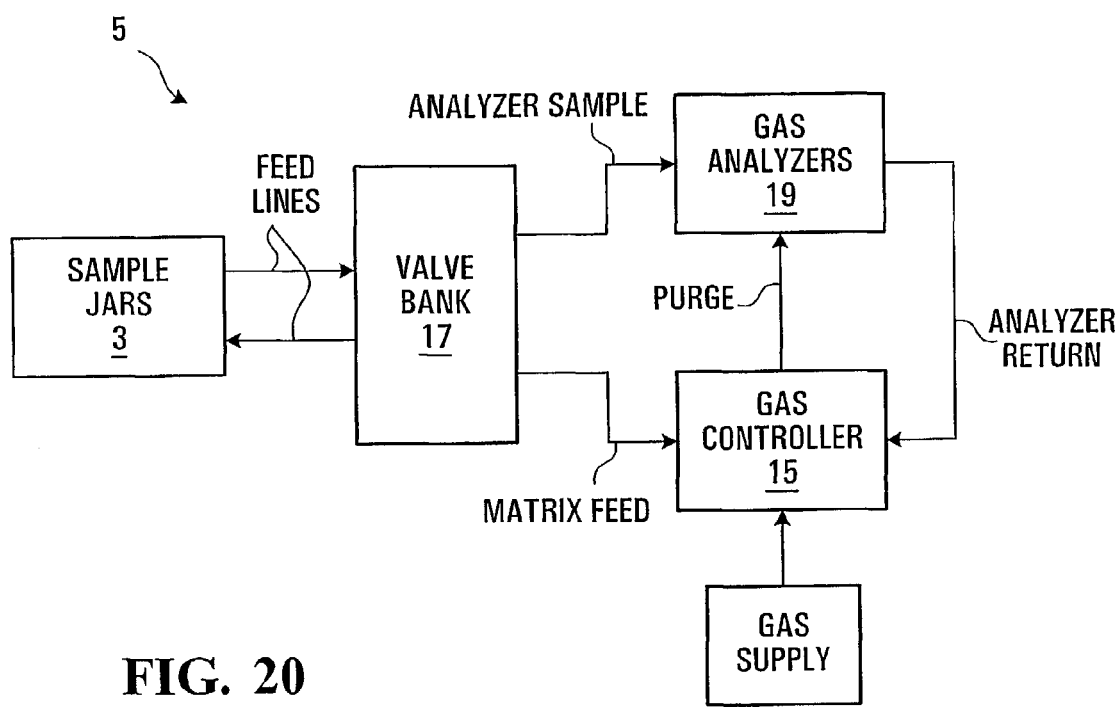
FIG. 20 shows a schematic diagram of the gas control system of FIG. 19.

Referring to FIG. 20, the gas control systems includes a gas controller 15 which receives carbon dioxide ($CO_2$) and nitrogen ($N_2$) from canisters 9,11 and air from the atmosphere, and feeds a specified amount of a selected gas to a particular sample jar. The sample jar is selected under the control of respective gas inlet valves, collectively shown as a valve bank 17, connected to the gas inlet port in each sample jar 3. Each sample jar 3 has a gas outlet port connected to a gas outlet valve, also shown as being grouped within the valve bank 17, which controls the flow of gas from each sample jar to gas analyzers, collectively shown at 19, for analyzing the content of various gases within the sample jars 3. In this embodiment, the gas analyzers measure the levels of carbon dioxide, oxygen and optionally ethanol.

Figure 21:
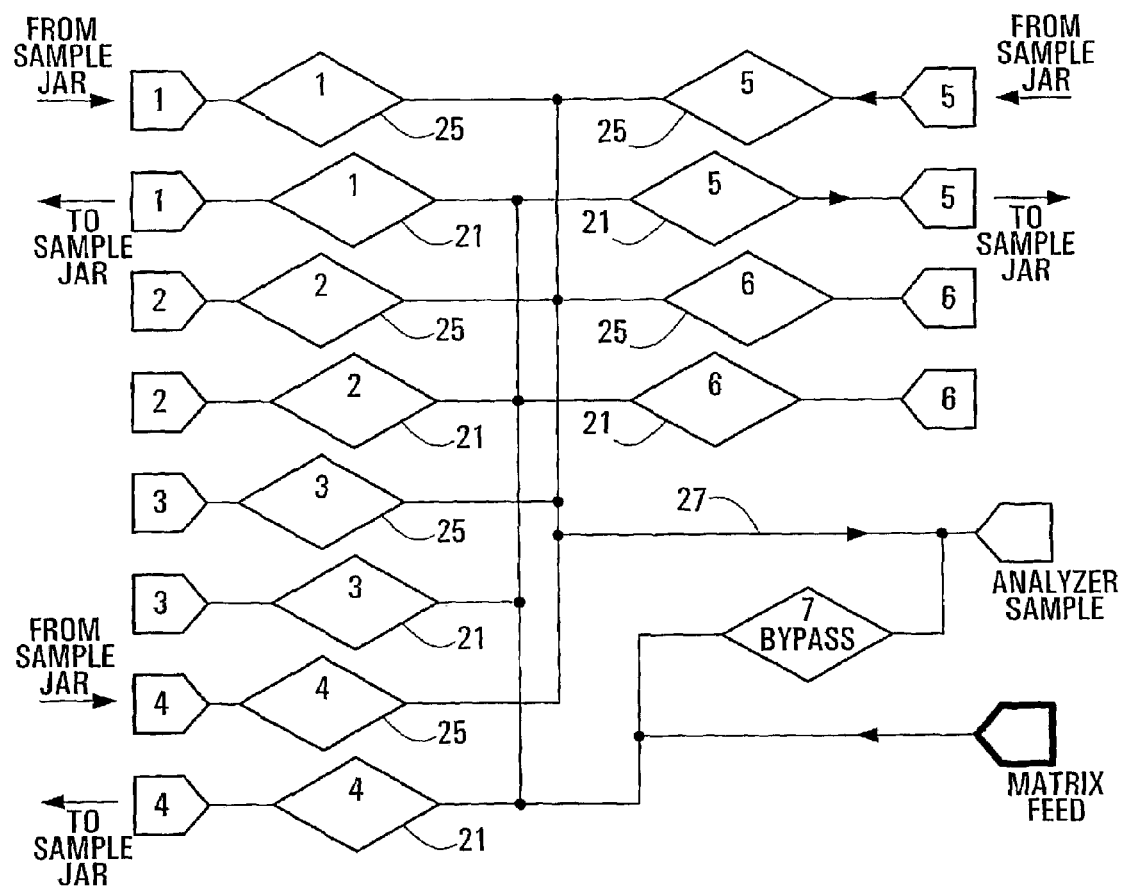
FIG. 21 shows a diagram of the control valve arrangement of the gas control system of FIG. 20.

Referring to FIG. 21, which shows an example of an arrangement of inlet and outlet gas control valves in more detail, each of the inlet valves 21 is connected to a feed line 23 which supplies gas from the gas controller to a particular jar selected according to which gas inlet valve is open. Each gas outlet valve 25 is connected to a common gas feed line 27 which supplies gas from a jar, selected according to which outlet valve is opened, to the gas analyzers 19. The inlet and outlet valves 21, 25 are preferably capable of being actuated electrically so that they can be opened and closed automatically under the control of the computer 13 (FIG. 19). Generally, when the gas in a particular jar is being sampled or its gas content changed, both the inlet and outlet valves of that jar particular are opened and the inlet and outlet valves of all other jars are closed.

Referring to FIG. 22, the gas analyzer system 19 includes a filter 29 connected to receive a gas sample from a selected sample jar and for removing any airborne particles, a pressure sensor 31 for measuring the gas pressure in the selected sample jar, an oxygen sensor 33, a carbon dioxide sensor 35 and, optionally, an ethanol sensor 37, for measuring the oxygen, carbon dioxide and ethanol content, respectively, of the gas in a specified jar. During gas sampling, a portion of the gas is drawn from the jar by a pump (not shown), is passed through each of the gas sensors and returned to the sample jar after analysis.

Between each jar sampling, the analyzers are purged by flushing with nitrogen gas to avoid cross contamination between different sample jars, and the purged gas is subsequently vented after leaving the gas analyzers.

To change the relative concentrations of the gases within a sample jar, a controlled amount of air, nitrogen or carbon dioxide is drawn into the jar by a pump. For example, to increase the oxygen content, air is pumped into the jar, whereas to decrease the oxygen level, nitrogen and/or $CO_2$ is pumped into the jar. In either case, the gas inlet and outlet valves of the selected jar are opened and gas is drawn from the jar, passed through the gas analyzers and returned to the jar. The gas controller 15 introduces the selected additional gas into the gas stream which subsequently mixes with the gases contained in the jar. A pump continues to draw gas from the sample jar and analyzes the gas sample for oxygen, $CO_2$ and ethanol, if required. When the desired gas concentration is obtained, the selected gas supply is stopped and the gas inlet and outlet valves closed. During any gas addition to the system, excess gas is vented so that the gas pressure remains substantially constant.

FIGS. 23 and 24 show an embodiment of a fluorometer used to stimulate and measure chlorophyll fluorescence from fruit or vegetable samples in each jar. The fluorometer 31 comprises three light source/sensing stations 33,35,37 spaced equally around and at equal distances from a sample jar 3, in a triangular arrangement, as shown in FIG. 23. The three light source/sensor station arrangement enables more representative measurements of the sample to be made. Referring to FIG. 24, each station comprises a rectangular array of four light emitting diodes (LEDs) 39,41,43,45, a source of white light 47 positioned within the rectangular array of LEDs and a photodiode 49, all mounted on a support panel 51. The light emitting diodes in each station serve to stimulate a minimal or dark fluorescence Fo in the chlorophyll of the fruit or vegetable sample. In one embodiment, the LEDs generate low intensity red light at wavelengths of about 660 nanometers with an intensity at the sample surface of generally less than 10 $\mu mol.m^{-2}.s^{-1}$. Light from the light emitting diodes is such as to cause chlorophyll fluorescence and is capable of stimulating fluorescence in the regime where all photosystem II reaction centres are open while the photosynthetic membrane is in the non-energized state, i.e. to measure a minimal fluorescence signal Fo. The photodiode 49 in each station detects the intensity of the fluorescence signal Fo. emitted by the chlorophyll which is recorded by the computer 13. The white light source 47 in each station serves to stimulate a maximal fluorescence signal Fm defined as the fluorescence intensity emitted when all photosystem II reaction centres are closed and all non-photochemical quenching processes at a minimum. In one embodiment, the white light source is a 250 Watt Tungsten filament bulb. Again, the photo diode 49 in each station detects the maximal fluorescence signal Fm which is again recorded by the computer 13.

Methods of determining an optimum oxygen level in which to store fruits and vegetables, according to embodiments of the present invention will now be described with reference to FIGS. 25A to 30B.

A fruit or vegetable sample is placed in a sample jar which is then sealed so that gas may only be introduced or drawn from the jar via the inlet and outlet ports under the control of the system control valves. Fruit or vegetable samples may additionally be placed in some or all of the other jars which are also subsequently sealed. The starting point oxygen concentration is then established in each jar and may range for example from 3 to 21 percent as required. A starting point of low oxygen concentrations may be established for fruit and vegetable samples which are known to be capable of tolerating low oxygen level atmospheres without being damaged by low oxygen stress. A measurement of the minimal fluorescence intensity Fo may be made at the oxygen concentration starting point, and, as described above, this is achieved by activating the light emitting diodes in each station of each fluorometer to irradiate portions of the surface of the fruit or vegetable sample to stimulate minimal chlorophyll fluorescence and detecting the fluorescence signal emitted from the chlorophyll by means of the photodiodes. A maximal fluorescence measurement may also be made by activating the white light source and, again, detecting the maximal fluorescence intensity by means of the photodiodes. The initial oxygen concentration and values of minimal and maximal fluorescence intensities are then recorded by the computer.

The oxygen concentration in one or more sample jars is then progressively reduced at a rate, for example 0.2%/h, by introducing additional quantities of nitrogen into the jar using, for example, the gas control system described above. A measurement of the minimal fluorescence intensity signal Fo and optionally the maximal fluorescence intensity signal Fm is made and recorded at each oxygen level.

For each measured oxygen concentration, a rolling average value of the minimal fluorescence intensity Fo is calculated based on the five previous and the current values of Fo. The difference between the current Fo value and the current rolling average value of Fo at each measured oxygen concentration is also calculated to give the change of the current Fo value from the current rolling average, and the fractional or percentage change between the current Fo value and the current rolling average value is then calculated. A current average fractional or percentage change is then calculated from the five previous values and the current value of the fractional or percentage change. The ultra low oxygen (ULO) threshold is determined as the oxygen level below which six consecutive values of the average fractional or percentage change in Fo is greater than 0.01 or 1%, respectively.

If Fm is measured, the value Fv/Fm, where Fv=Fm−Fo, may also be calculated.

Examples of applications of the above described method to determine the optimum oxygen concentration for controlled atmosphere storage of various fruit samples are described below.

EXAMPLE 1

Figure 25A:
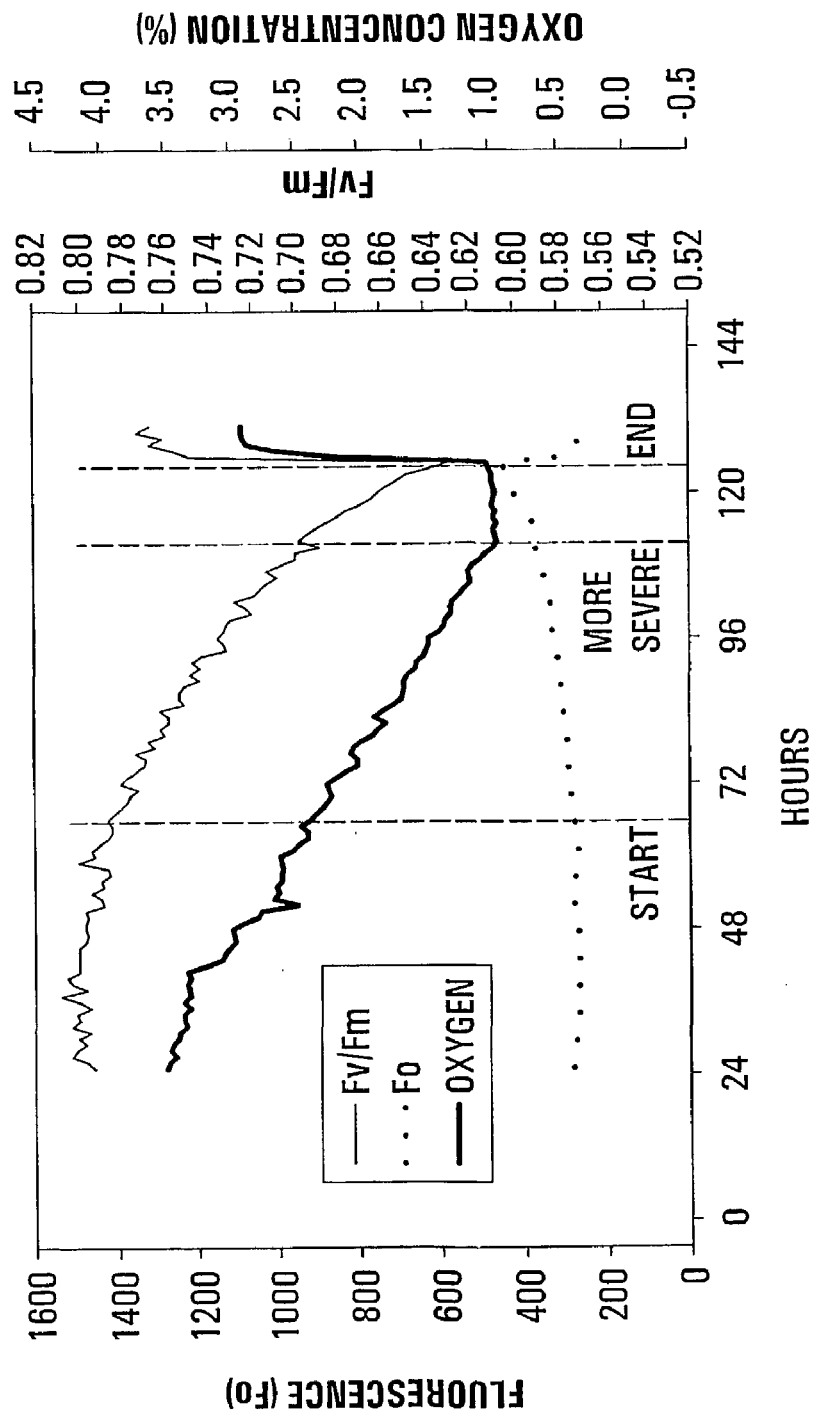
FIG. 25A shows a graph of the variation of chlorophyll fluorescence with oxygen concentration for an apple sample.

The method according to the above described embodiment was applied to an apple sample. FIG. 25A shows a graph of the variation of Fo, Fv/Fm and percentage oxygen concentration with time, and FIG. 25B shows a table of measured values of percentage oxygen content, minimal and, maximal fluorescence intensities Fo and Fm, calculated values of the rolling average of Fo, the change or difference between the current measured Fo and rolling average Fo values, the calculated percentage change and the average percentage change.

Referring to FIG. 25A, the oxygen concentration was progressively and gradually reduced and the minimal and maximal chlorophyll fluorescence intensities were measured every hour along with the oxygen concentration. The graph and table show that Fo remains substantially constant until hour 65, after which time Fo steadily increases and the average percentage change in Fo for the next consecutive 6 hours, i.e. from hour 66 to hour 71 is greater than 1%. The increase in Fo and in its average percentage change indicates a precipitation of low oxygen stress and the onset of possible damage. The optimum oxygen concentration for storing any fruit or vegetable is the lowest value above that which would otherwise cause damage to the product by low oxygen stress. In the present embodiment, the optimum oxygen concentration is determined as that just before the average percentage change reaches a value of greater than 1% for six consecutive readings, which in the present case 2.44%.

Referring again to FIGS. 25A and 25B, Fo continues to increase as the oxygen concentration continues to decrease below the optimum threshold and the change in Fo becomes more severe from hour 108 onwards, as shown by the increase in the average percentage change from this point in the table of FIG. 25B.

Figure 25B:
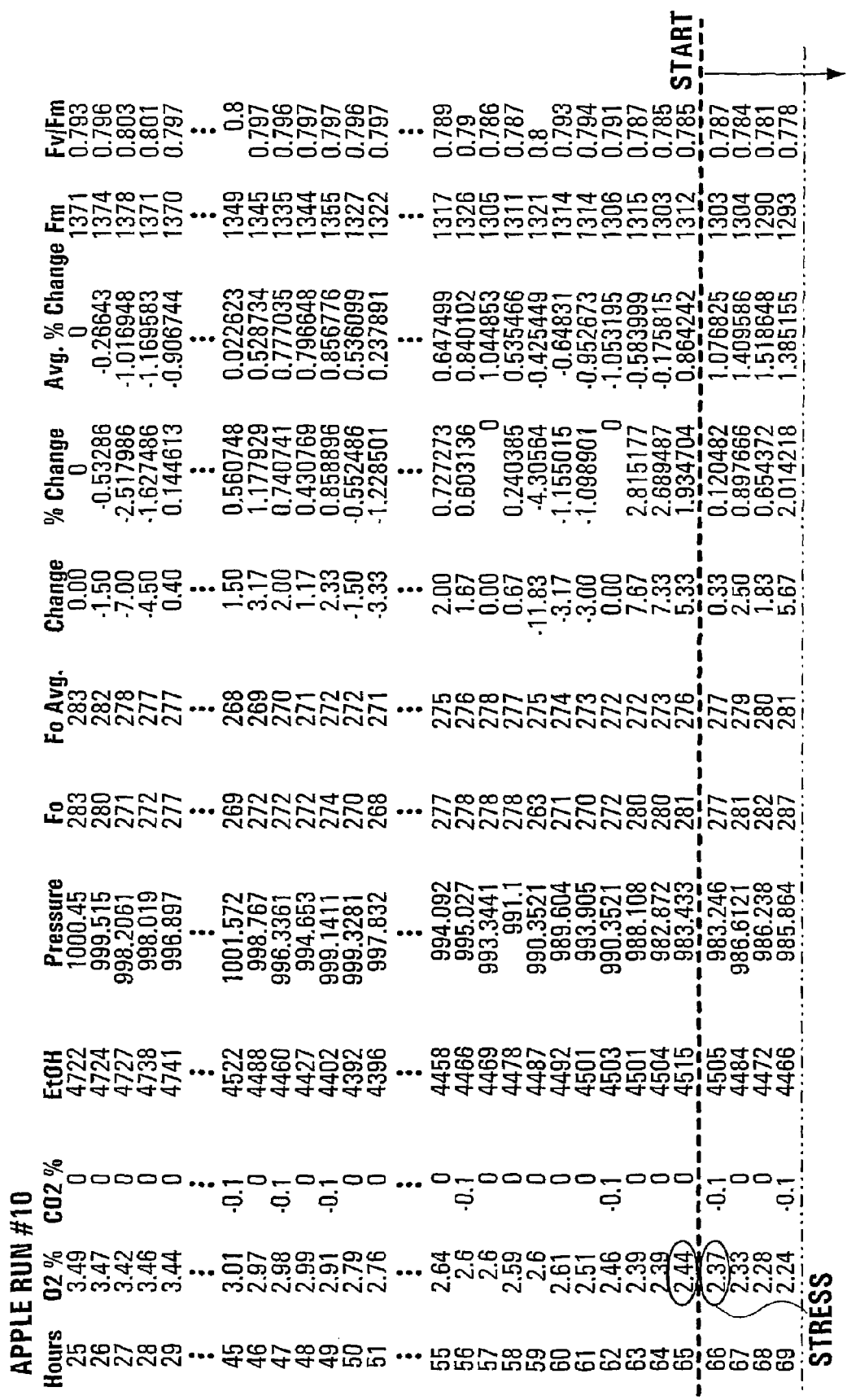
FIG. 25B shows a table of numerical data plotted in the graph of FIG. 25A.

FIGS. 25A and 25B also show that Fv/Fm progressively decreases as the oxygen concentration is reduced and then begins to decrease at a higher rate at a point in time and oxygen concentration which closely corresponds to the optimum oxygen concentration at which the change in Fo begins to increase. As the oxygen concentration is lowered still further, Fv/Fm decreases more abruptly at a position in time and at a value of oxygen concentration closely corresponding to that at which Fo exhibits a more severe increase.

FIG. 25A also shows that when the oxygen concentration is suddenly increased from its lowest level to a value above the optimum threshold level, Fo decreases at a similar rate to a value closely corresponding its former values above the optimum oxygen concentration threshold. Fv/Fm also increases at a similar rate, returning to levels similar to those prior to the onset of the increased change at the optimum oxygen concentration level. This latter behaviour indicates that no permanent damage was sustained by the fruit in the method of determining the optimum oxygen concentration threshold and that the method advantageously provides a means for determining this value without destroying the sample.

EXAMPLE 2

Figure 26A:
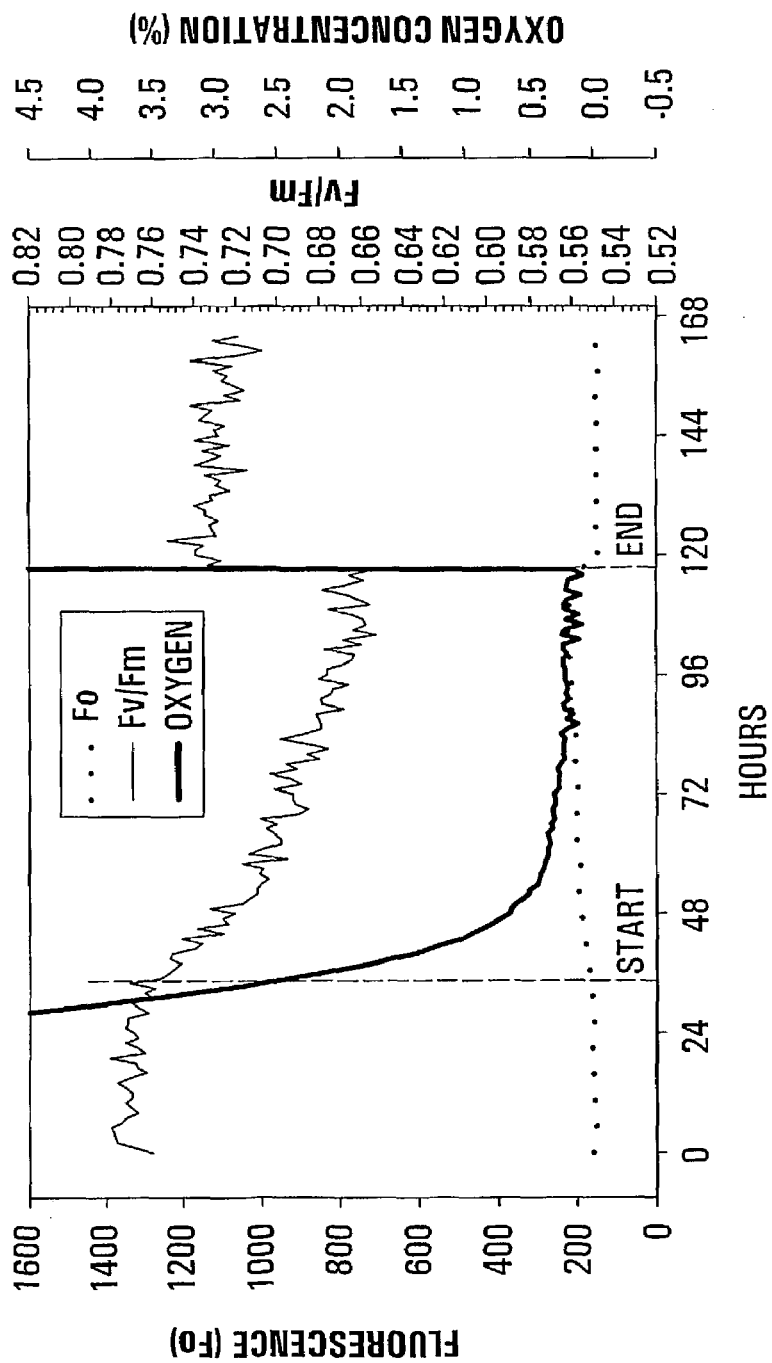
FIG. 26A shows a graph of the variation of chlorophyll fluorescence with oxygen concentration for a kiwi fruit sample.
Figure 26B:
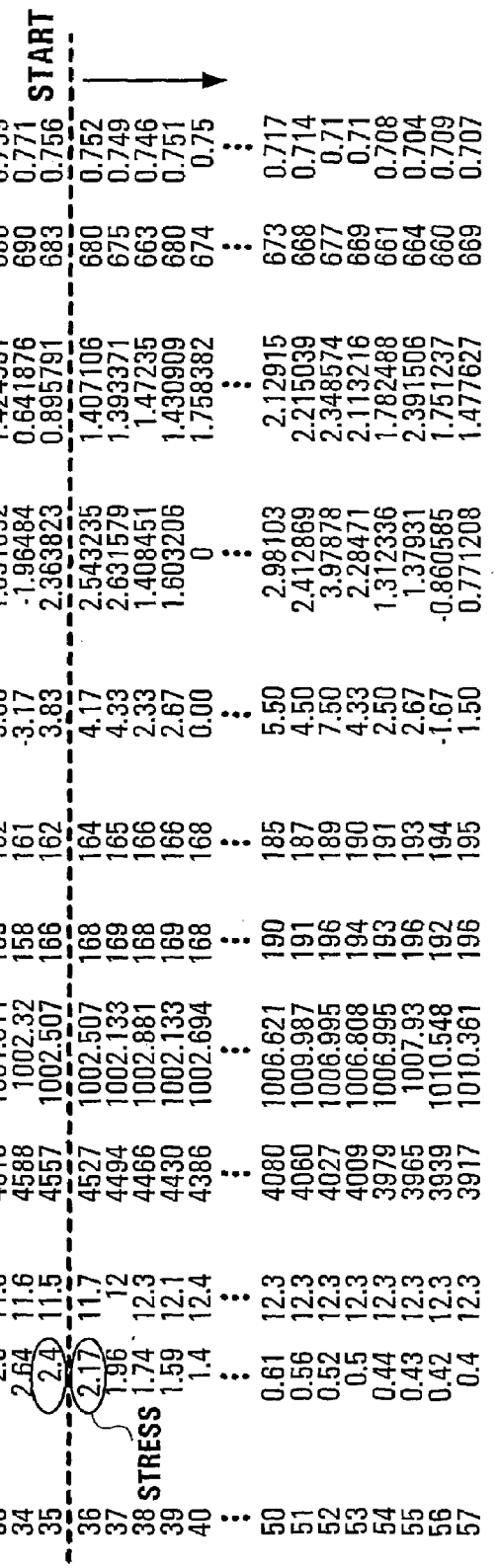
FIG. 26B shows a table of part of the numerical data plotted in the graph of FIG. 26A.

FIG. 26A is a graph showing the variation of Fo and Fv/Fm for a kiwi fruit sample as the oxygen concentration in which the sample is placed is progressively reduced. FIG. 26B shows part of the data plotted in FIG. 26A in tabulated form, and in addition the rolling average of Fo, the change between the current value of Fo and its corresponding rolling average, the percentage change and the average percentage change in Fo, the maximal fluorescence Fm and the calculated value of Fv/Fm. As the oxygen concentration is progressively lowered, Fo remains substantially constant until a time corresponding to hour 36 at which Fo increases and the average percentage change in Fo exceeds 1% and remains above 1% for the next consecutive six points, and beyond, as the oxygen concentration continues to be reduced. This increase in the change of Fo indicates the onset of low oxygen stress in the kiwi fruit sample. The optimal oxygen concentration threshold may be determined as the oxygen concentration just prior to the onset of this increase in the change of Fo, which in the present case is 2.4%.

Returning to FIG. 26A, it can be seen that, initially, at the higher oxygen concentrations, Fv/Fm steadily decreases between hours 0 and 35 (ignoring the periodic fluctuations) and at a time and the same value of oxygen concentration as the change in Fo has started to increase, the change in Fv/Fm also starts to increase. Thus, measuring the change in Fv/Fm may also be used to determine the optimal oxygen concentration threshold.

As the oxygen concentration is progressively reduced below the oxygen threshold measured at hour 35, Fo continues to increase whereas Fv/Fm continues to decrease, both indicating a continued increase in low oxygen stress in the sample. As the oxygen level is suddenly increased just before hour 120, Fo is seen to decrease and Fv/Fm is seen to increase at a similar rate towards their former, pre-oxygen stress levels.

EXAMPLE 3

Figure 27A:
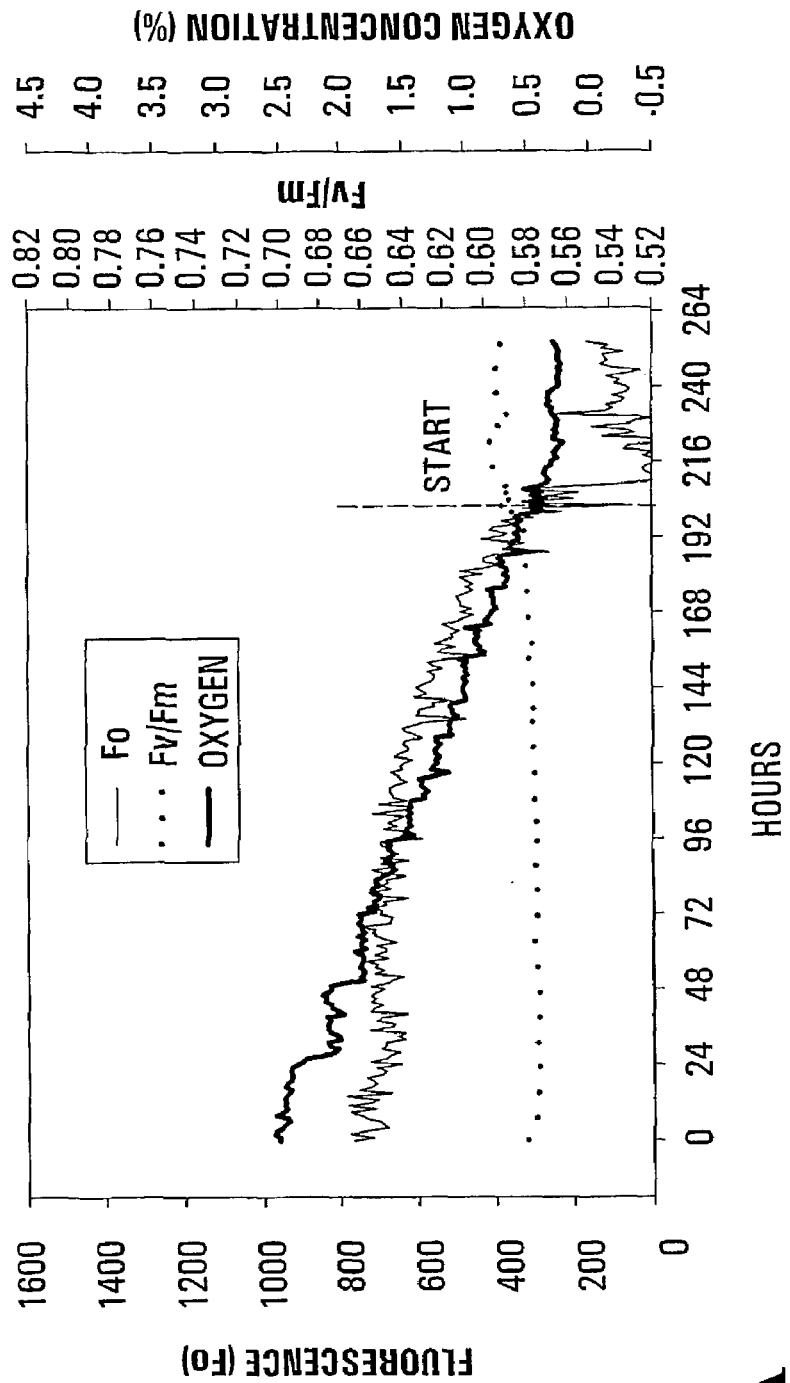
FIG. 27A shows a graph of the variation of chlorophyll fluorescence with oxygen concentration for a mango sample.
Figure 27B:
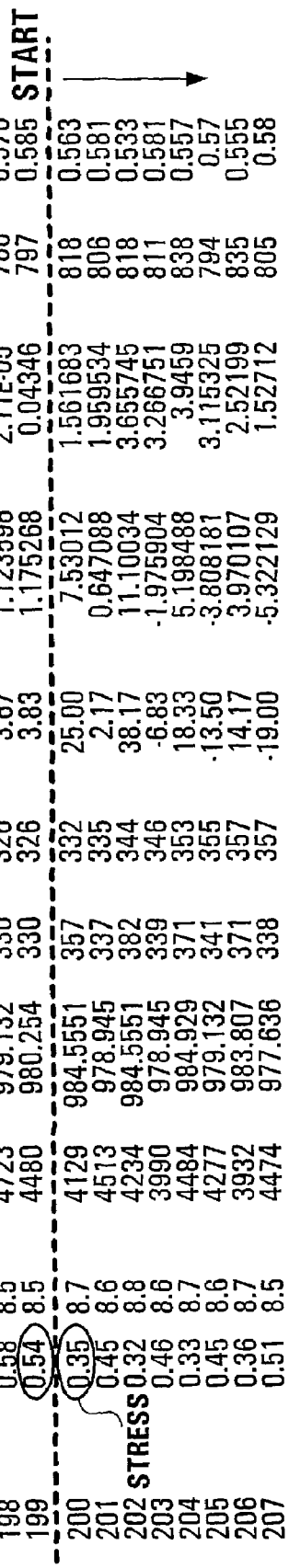
FIG. 27B shows a table of part of the numerical data plotted in the graph of FIG. 27A.

FIGS. 27A and 27B show the variation in Fo and Fv/Fm for a mango sample as the oxygen concentration of the atmosphere in which the sample is placed is progressively reduced. The results indicate that initially the minimal fluorescence intensity Fo remains relatively constant with decreasing oxygen concentration and then at a time corresponding to hour 200, Fo begins to increase such that its average percentage change exceeds 1% for at least the next consecutive six points. The optimum oxygen concentration threshold for the mango sample may then be determined from this transition of the change in Fo as 0.4%: the oxygen concentration at hour 199 just prior to the point at which the average percentage change in Fo continuously exceeds 1%.

As can been seen from FIG. 27A, Fv/Fm steadily decreases with decreasing oxygen concentration and then at a point corresponding to that at which the change in Fo increases, Fv/Fm exhibits a precipitous drop also indicating the onset of low oxygen stress in the mango sample.

EXAMPLE 4

Figure 28A:
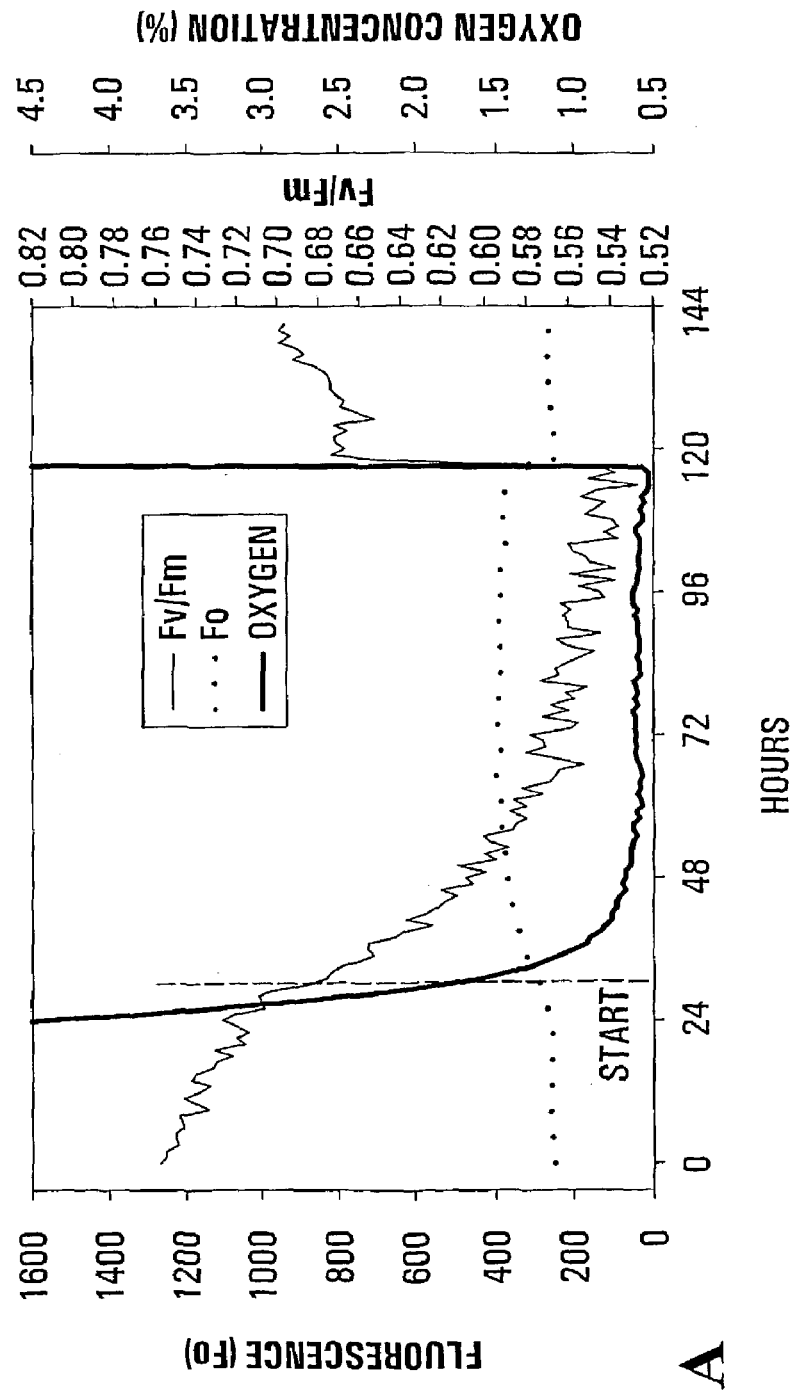
FIG. 28A shows a graph of the variation of chlorophyll fluorescence with oxygen concentration for a pear sample.

FIGS. 28A and 28B show the variation in minimal fluorescence intensity Fo and FV/Fm for a pear sample as the oxygen concentration of the atmosphere in which the pear sample is placed is progressively reduced. The measurements indicate that, initially, Fo remains relatively constant with decreasing oxygen concentration until a time corresponding to hour 28 at which Fo starts to progressively increase, indicating the onset of low oxygen level stress occurring in the sample. At this point, the average percentage change in Fo exceeds and continues to exceed 1%, as shown in the table of FIG. 28B. The optimal oxygen concentration threshold is determined on the basis of this change in Fo and for example may be established as the oxygen concentration of 2.87% just before the onset of the increase in Fo which also corresponds to the oxygen concentration just before the average percentage change in Fo continuously exceeds 1% for at least the next six consecutive points.

Returning to FIG. 28A, Fv/Fm initially exhibits a steady, substantially monotonic decrease (ignoring periodic fluctuations in the data) as the oxygen concentration is progressively reduced and then at a point which substantially corresponds the point at which Fo increases, the decrease in Fv/Fm markedly accelerates.

EXAMPLE 5

Figure 29A:
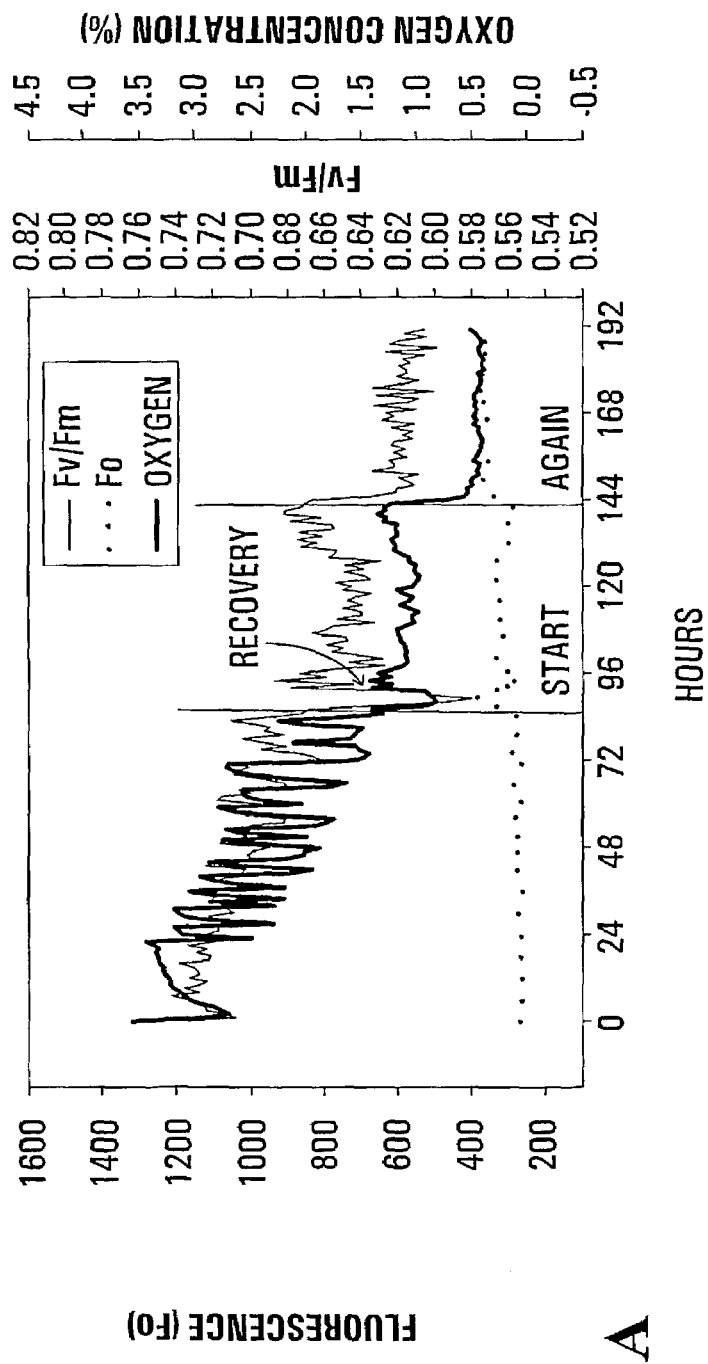
FIG. 29A shows a graph of the variation of chlorophyll fluorescence with oxygen concentration for an avocado sample.
Figure 29B:
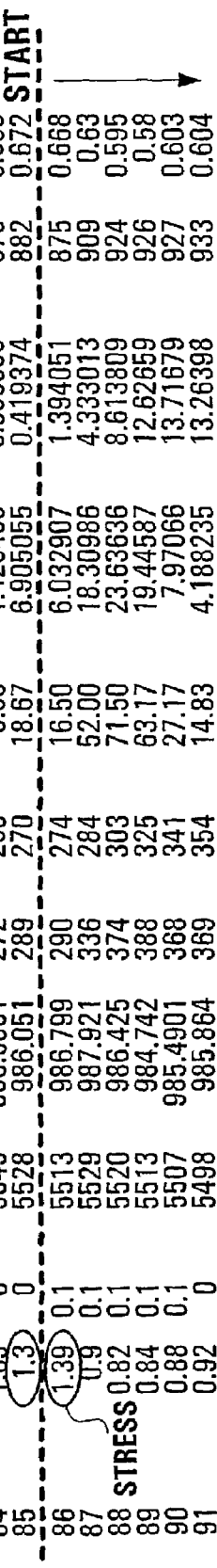
FIG. 29B shows a table of part of the numerical data plotted in the graph of FIG. 29A.

FIGS. 29A and 29B show the variation in the minimal fluorescence intensity Fo and Fv/Vm for an avocado sample as the oxygen concentration of the atmosphere in which the sample is placed, is progressively reduced. Initially, Fo remains substantially constant with decreasing oxygen concentration until, at a time corresponding to hour 86, Fo begins to increase, indicating the onset of low oxygen stress in the sample. The optimal oxygen threshold may be determined on the basis of this increase in Fo and established as for example 1.3% corresponding to hour 85, just prior to the average percentage change continuously exceeding 1% for six consecutive readings.

Referring to FIG. 29A, Fv/Fm initially decreases at a steady rate as the oxygen concentration is progressively lowered (allowing for the frequent, intermediate fluctuations in data) and at a point closely corresponding to that at which Fo increases, Fv/Fm exhibits a precipitous drop as the oxygen concentration is lowered further.

EXAMPLE 6

Figure 30A:
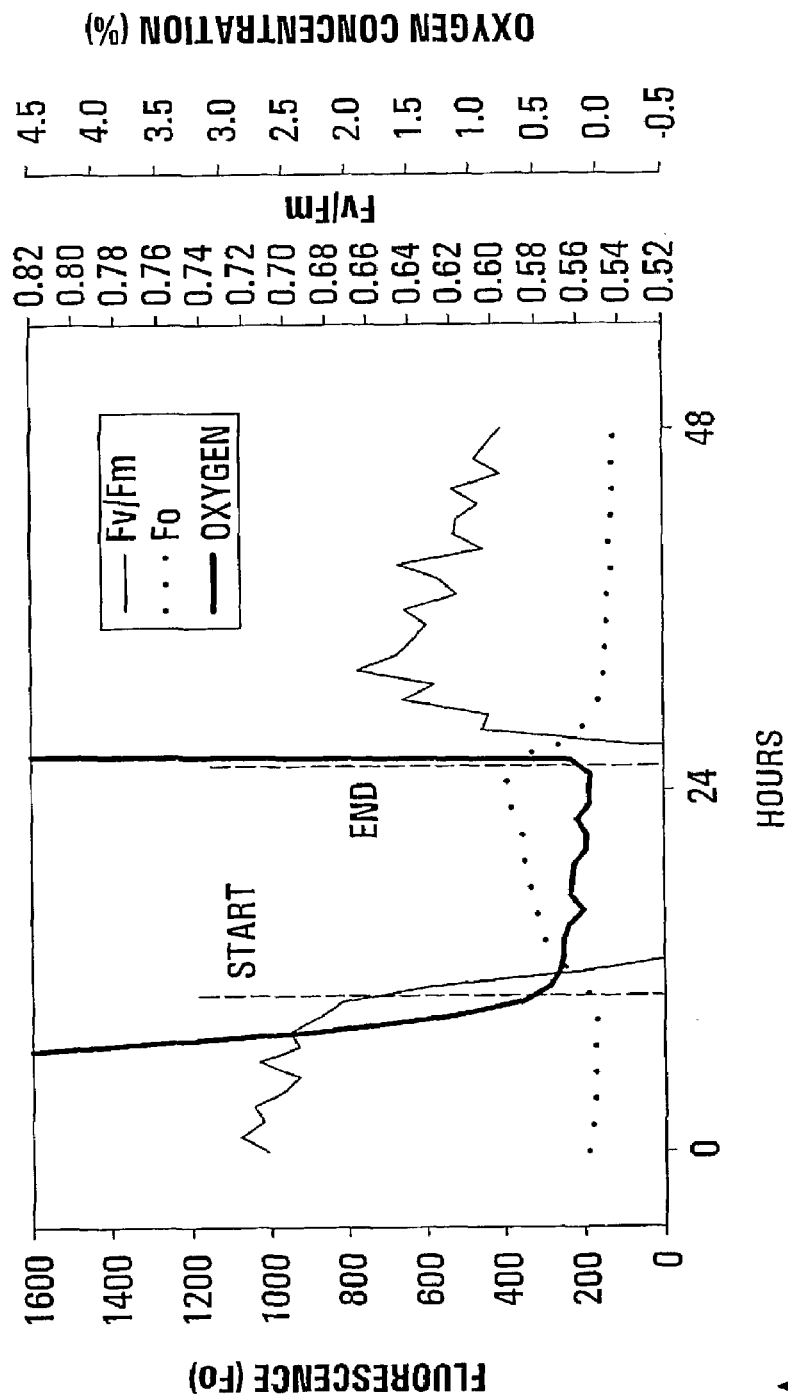
FIG. 30A shows a graph of the variation of fluorescence with oxygen concentration for a banana sample.

FIGS. 30A and 30B show the variation in minimal fluorescence intensity Fo and Fv/Fm for a banana sample as the oxygen concentration of the atmosphere in which the sample is held, is progressively reduced. Initially, at higher oxygen concentrations Fo steadily decreases until a time corresponding to hour 11 at which Fo starts to increase, indicating the onset of low oxygen stress in the sample. The optimal oxygen concentration threshold for storing the banana sample may be determined on the basis of the transition in the change in Fo and for example may be established as an oxygen concentration of 0.61% corresponding to hour 10. Below this oxygen concentration, the average percentage change in Fo exceeds 1% for at least six consecutive readings as the oxygen concentration is lowered further.

Referring to FIG. 30A, at higher oxygen concentrations, Fv/Fm initially exhibits a steady downward progression (allowing for periodic fluctuations in the data) and then, at a point substantially corresponding to that at which Fo begins to increase, the decrease Fv/Fm suddenly accelerates.

The above examples 1 to 6 illustrate that the method according to embodiments of the invention may be used to detect the onset of low oxygen stress in chlorophyll containing produce and to determine the specific optimal oxygen concentration threshold which minimizes respiration without causing damage, for a given product. Advantageously, this allows the time over which the product can be stored without deterioration of quality to be maximized or, if the product is to be stored for a period of time less than the maximum, the method allows any deterioration in the product to be minimized over that time and therefore the quality of the product after the storage time to be improved in comparison to products stored under existing storage techniques.

In any of the above examples, and in practising embodiments of the method for mass fruit and vegetable storage, the optimal oxygen threshold may be determined more accurately by making additional, intermediate measurements of Fo and/or Fv/Fm around the oxygen concentrations where the changes in these parameters begin to increase.

In another embodiment of the present invention, a method of controlling the oxygen concentration in an atmosphere in which chlorophyll containing fruit or vegetables are stored comprises varying the oxygen concentration and monitoring the minimal fluorescence intensity Fo emitted by the stored produce and determining from the measured intensity, the oxygen concentration at which the onset of low oxygen stress in the produce occurs, preferably controlling the oxygen concentration to minimize respiration of the produce without causing low oxygen damage and immediately or after some time has elapsed, again reducing the oxygen concentration to determine any change in the optimum oxygen concentration threshold, and adjusting the oxygen concentration based on any change in the optimum threshold value.

The inventors have found that during storage, a product's tolerance to low oxygen levels before the onset of low oxygen stress can increase with time, so that the optimum oxygen concentration threshold for a particular product can decrease during the storage period. Therefore, the present method allows the storage time to be extended further by periodically reducing the oxygen concentration and monitoring the minimal fluorescence intensity Fo to determine any change in the optimum oxygen concentration threshold. This method effectively uses the stored product to indicate the lowest oxygen concentrations it can tolerate at various times during the storage period so that the oxygen concentration can be dynamically adjusted to provide the optimum conditions for maximizing the storage period for the particular product. An example of this method applied to the storage of apples will now be described under example 7.

EXAMPLE 7

The following test was applied to McIntosh cultivars of Marshall and Red Max apples which were held under controlled atmosphere (CA) conditions for four months. A first sample of the apples were placed storage conditions in which the oxygen and carbon dioxide concentrations were held constant over the 4 month storage period at 2.5% $O_2$ and 4.5% $CO_2$. A second sample of the apples were placed under storage conditions in which the oxygen concentration was periodically stepped down based on what the fluorescence intensity emitted by the fruit indicated was the lowest oxygen concentration they could withstand without inducing damage.

After a period of four months, both samples were removed from storage and subjected to firmness and taste tests, as follows. Immediately after the four month storage period, samples were placed in cold storage for fourteen days at 3° C. and thereafter tested for firmness. The results for two Marshall and one Red Max apple stored in each of the constant (standard) and stepped oxygen concentration conditions are shown in Table 7 of FIG. 31. The results indicate that the apples stored in the stepped controlled atmosphere were on average 1.49 pounds firmer than those stored in the constant controlled atmosphere.

The samples of the apples stored in each of the constant and stepped CA storage conditions were taste tested by twelve panellists. The results show that for Marshall MacIntosh apples, 40% of the panellists expressed a preference for the apples stored under the stepped controlled atmosphere conditions, whereas 25% expressed a preference for the apples stored under the standard conditions.

For the Red Max cultivar, 90% of the panellists expressed a preference for those apples stored under stepped conditions, whereas no panellists expressed a preference for those stored under standard conditions.

Both the Marshall McIntosh and Red Max were also tested for the presence of off-flavours. The results show that for Marshall McIntosh, 70% of panellists detected no off-flavours in the samples stored under the stepped conditions whereas 50% of panellists detected no off-flavours in the apples stored under standard conditions. For Red Max, 90% of panellists detected no off-flavours in the samples stored under stepped conditions, whereas 50% of panellists detected no off-flavours in the Red Max McIntosh samples stored under the standard conditions.

These results collectively indicate that measurements of chlorophyll fluorescence on stored fruit allows the optimum oxygen concentration threshold to be found and that dynamically adjusting the oxygen concentration to track the optimum threshold as the threshold varies over the storage period better preserves the fruit quality.

An embodiment of an apparatus for tracking the optimum concentration threshold during the storage of fruit or vegetables comprises means for detecting an increase in the change in fluorescence intensity with decreasing oxygen concentration, means for controlling the oxygen concentration to a level corresponding to the increase in fluorescence intensity and means for periodically reducing the oxygen concentration and re-establishing the optimal oxygen concentration based on any increase in the change of fluorescence intensity as the oxygen concentration is lowered. The oxygen concentration and fluorescence measurements may be controlled by a microprocessor under the control of a suitable program.

In another embodiment of the method of determining an optimum oxygen concentration threshold for storing a chlorophyll containing product or for storing such a product, the oxygen concentration may initially be lower than the optimum threshold, and the threshold found by progressively increasing the oxygen concentration. In this case, the threshold may be signified by a transition in which the change in Fo and/or the change in Fv/Fm decreases as the oxygen concentration is increased.

Nitrogen Flush Experiment

Figure 32A:
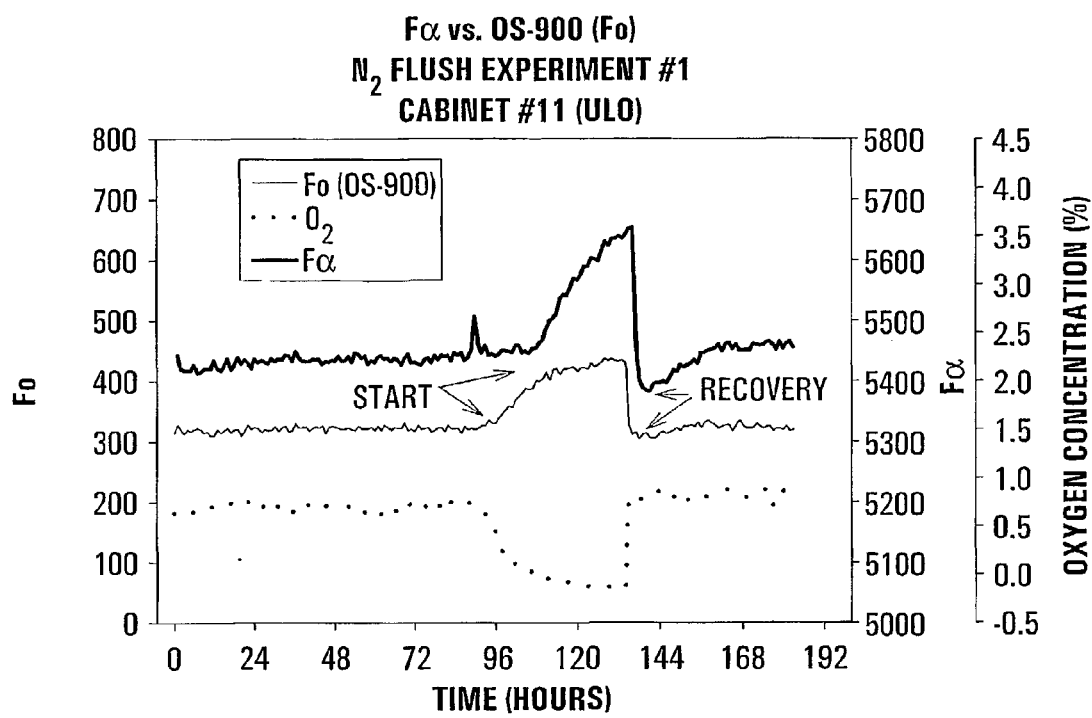
FIGS. 32A and 32B shows a graph of Fα and FO measured during a simulated Nitrogen Flush accident.
Figure 32B:
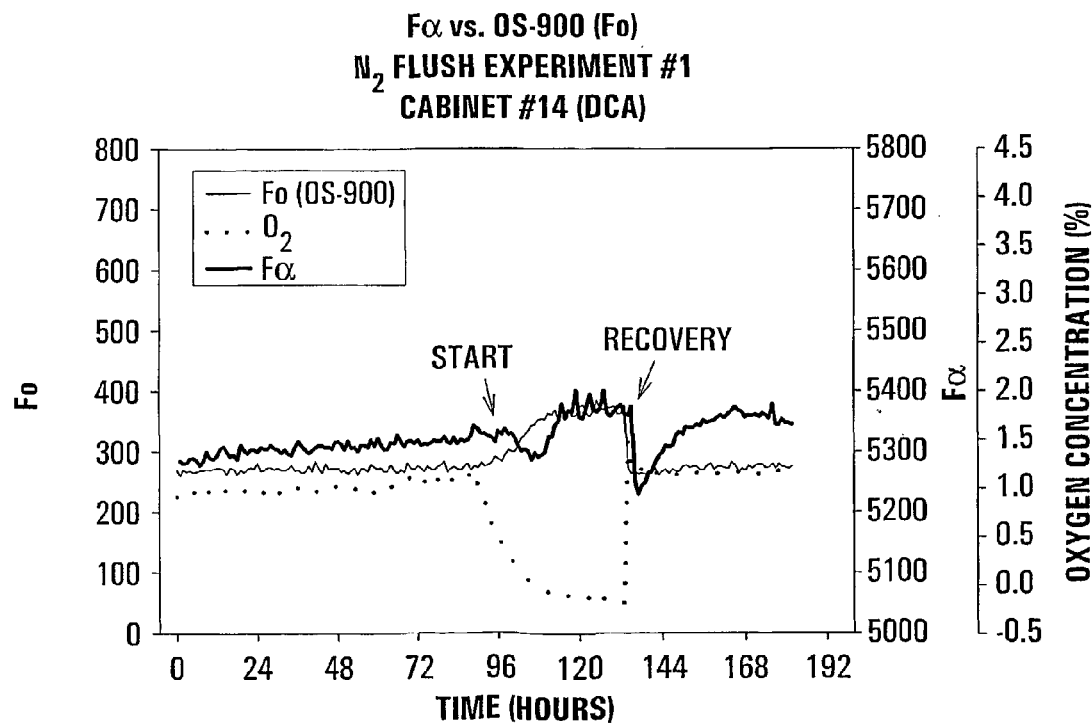

FIGS. 32A and 32B show graphs of Fa and minimal fluorescence Fo in response to a simulated nitrogen flush accident in which the oxygen level in a storage container containing Summerland McIntosh apples remained at very low levels for a period of time. Both FIGS. 32A and 32B show that both Fa and Fo of the chlorophyll fluorescence signal emitted by the apples increased as the oxygen level decreased, indicating a change in their health attributable to low oxygen stress. Thus, embodiments of the fluorescence monitoring apparatus and method can be used independently to detect the presence of oxygen levels which would be detrimental to the health of produce which may occur for example during a CA storage nitrogen flush where the oxygen levels fail to return to a healthy level.

In other embodiments of the present invention, a plurality of fluorescence monitoring devices may be used, each for example comprising a device as shown in FIG. 1. The devices may be controlled by one computer and inter communication between the computer and the devices may be made via a hub, connecting the devices to a computer. Different devices may be controlled by different computers.

A monitoring device may have any number of individual light source elements and light sensors.

In embodiments where the light level is varied, the light level may be actinic, non-actinic or cover a range of non-actinic to actinic levels.

Modifications, alternatives and equivalents to the embodiments described above will be apparent to those skilled in the art.

The invention claimed is:

1. A method of detecting the onset of an at least partially reversible stress condition in chlorophyll-containing matter caused by said chlorophyll-containing matter being exposed to a stress inducing environmental condition, the method comprising:
   (a) exposing the matter to light to cause chlorophyll in the matter to fluoresce and emit a fluorescence signal,
   (b) detecting the emitted fluorescence signal,
   (c) measuring the value of a parameter based on the detected fluorescence signal,
   (d) monitoring the value of said parameter,
   (e) detecting changes in the value of said parameter,
   (f) providing a threshold value of a predetermined level of change in said parameter which only if reached and exceeded signifies the onset of said at least partially reversible stress condition in the chlorophyll-containing matter caused by said stress inducing environmental condition, and
   (g) comparing changes in the value of said parameter with said threshold value, wherein a determination that the value of said parameter reaches and exceeds said threshold value signifies the onset of said at least partially reversible stress condition in the chlorophyll-containing matter caused by said stress inducing environmental condition.

2. The method of claim 1, comprising making a plurality of measurements of said parameter, and reducing the exposure of said matter to said light between each said measurement.

3. The method of claim 1, comprising making a plurality of measurements of said parameter at substantially the same level of photon flux to which said matter is exposed.

4. The method of claim 1, wherein the level of photon flux to which said matter is exposed is below that required to stimulate a maximal fluorescence signal in said chlorophyll-containing matter.

5. The method of claim 1, wherein said level of photon flux is substantially that required to stimulate a minimal fluorescence signal Fo.

6. The method of claim 1, wherein said parameter is the intensity of said fluorescence signal.

7. The method of claim 1, comprising measuring the intensity of the fluorescence signal at each of a plurality of different light levels, and deriving said parameter based on said plurality of fluorescence signal intensity measurements.

8. The method of claim 7, wherein said parameter is based on the relationship between a plurality of measured fluorescence intensities, each measured at a different light level.

9. The method of claim 8, wherein said parameter is a descriptor of said relationship.

10. The method of claim 9, wherein said parameter is a fluorescence intensity based on a plurality of measured fluorescence intensities.

11. The method of claim 10, wherein said parameter is the fluorescence intensity, $F\alpha$, at a level of light exposure of said chlorophyll-containing matter to zero photon flux.

12. The method of claim 8, comprising fitting a mathematical expression to a plurality of measured fluorescence intensities and wherein said parameter comprises a descriptor of said mathematical expression.

13. The method of claim 12, wherein said mathematical expression comprises a polynomial regression.

14. The method of claim 13, wherein said polynomial regression comprises a second order polynomial regression.

15. The method of claim 14, wherein said parameter comprises the value of a constant which qualifies a term of said polynomial regression.

16. The method of claim 7, wherein each of said plurality of different light levels to which said chlorophyll-containing matter is exposed is below that required to stimulate a maximal fluorescence signal in said chlorophyll-containing matter.

17. The method of claim 7, wherein said light comprises red light.

18. The method of claim 1, wherein the step of exposing the matter to light comprises exposing said matter to a predetermined level of photon flux by generating a predefined series of light pulses, said level of photon flux being the integrated photon flux of said series of pulses.

19. The method of claim 18, wherein the step of exposing said matter to light comprises irradiating said matter sequentially with light at a plurality of different levels of photon flux wherein each level of photon flux is generated by generating a predefined series of light pulses, each light level being the integrated photon flux of each series of pulses.

20. The method of claim 19, wherein each different light level is generated by changing a parameter defining said series of pulses.

21. The method of claim 20, wherein the step of changing the integrated photon flux to which said matter is exposed comprises at least one of changing the pulse frequency, changing the pulse width, changing the intensity of the pulses and changing the time over which said series of pulses extends.

22. The method of claim 21, further comprising measuring the intensity of the fluorescence signal emitted in response to each of a plurality of said pulses within a series.

23. The method of claim 22, further comprising the step of calculating the average value of the fluorescence intensity from said plurality of intensity measurements.

24. The method of claim 23, further comprising calculating the average fluorescence intensity at each of a plurality of different values of integrated photon flux.

25. The method of claim 24, comprising the step of deriving said parameter from said plurality of calculated average fluorescence intensities.

26. The method of claim 1, further comprising monitoring said stress inducing environmental condition.

27. The method of claim 26, wherein the step of monitoring said environmental condition comprises monitoring a parameter affecting the health of said chlorophyll-containing matter.

28. The method of claim 27, said method further comprising the step of recording the value of said parameter affecting the health of said chlorophyll-containing matter when said change in said parameter based on the detected fluorescent signal exceeds said predetermined level.

29. The method of claim 1, further comprising changing the level of exposure of said chlorophyll-containing matter to a condition.

30. The method of claim 29, wherein the step of changing the level of exposure comprises changing said condition.

31. The method of claim 30, wherein changing said condition comprises changing said condition between a value that is insufficient to stress said chlorophyll-containing matter and a value that is sufficient to stress said chlorophyll-containing matter.

32. The method of claim 1, further comprising controlling the level of exposure of said chlorophyll-containing matter to said environmental condition based on the detection of a change in said parameter above said predetermined level.

33. The method of claim 32, wherein said environmental condition comprises at least one of a material absorbed by or taken up by said chlorophyll-containing matter, the concentration of a gas or liquid in the atmosphere to which said chlorophyll-containing matter is exposed, temperature, humidity and the pressure to which said chlorophyll containing matter is exposed.

34. The method of claim 1, said method further comprising the steps of performing steps (a), (b) and (c) before said matter is exposed to a stress inducing condition, periodically repeating steps (a), (b) and (c) before said matter is exposed to a stress inducing condition, determining a base level of any change in said parameter based on two or more measurements of said parameter made before said matter is exposed to a stress inducing condition, and determining a level above said base level as said predetermined level of change.

35. The method of claim 34, comprising repeating step (c) at predetermined successive intervals of time before said matter is exposed to a stress inducing condition.

36. The method of claim 1, wherein said predetermined level is substantially equal to or greater than about 1%.

37. The method of claim 1, wherein said change in said parameter above said predetermined level of change occurs with an increase in the intensity of the detected fluorescence signal.

38. The method of claim 1, comprising exposing said chlorophyll-containing matter to an atmosphere containing a predetermined gas, progressively changing the level of said predetermined gas to which said chlorophyll-containing matter is exposed from a level which is insufficient to induce stress in said chlorophyll-containing matter to a level which is sufficient to induce stress in said chlorophyll-containing matter, and said detecting comprises detecting the onset of said at least partially reversible stress condition caused by exposing said chlorophyll-containing matter to a level of said predetermined gas.

39. The method of claim 38, wherein said gas comprises oxygen and the step of progressively changing comprises progressively reducing the level of oxygen to which said chlorophyll containing matter is exposed.

40. The method of claim 38, wherein said predetermined gas comprises carbon dioxide, and the step of progressively changing comprises progressively increasing the level of carbon dioxide to which said chlorophyll-containing matter is exposed.

41. The method of claim 1, wherein step (a) comprises exposing said chlorophyll-containing matter to at least three different levels of light to cause chlorophyll in the matter to fluoresce and emit a fluorescence signal at each different light level, each different light level being below that required to stimulate a maximal fluorescence signal in said chlorophyll-containing matter, measuring the intensity of the fluorescence signal emitted from the chlorophyll-containing matter at each different light level, and step (c) comprises determining from the measured intensities, a relationship between the measured intensities as a function of a parameter indicative of level of light to which the chlorophyll-containing matter is exposed, and deriving the value of said parameter from said relationship.

42. The method of claim 41, wherein said parameter comprises any one of the fluorescence intensity, $f\alpha$, at a level of light exposure of said $f\alpha$ to zero photon flux, and the value of a coefficient of a term of a polynomial regression describing the relationship between said measured intensities.

43. An apparatus for detecting the onset of an at least partially reversible stress condition in chlorophyll-containing matter, comprising:
(a) a light source for causing chlorophyll in chlorophyll-containing matter to fluoresce and emit a fluorescence signal,
(b) a detector for detecting the fluorescence signal,
(c) measuring means for measuring the value of a parameter based on the detected fluorescent signal,
(d) monitoring means for monitoring changes in the value of said parameter,
(e) a device storing a threshold value of a predetermined level of change in said parameter, which only if reached and exceeded signifies the onset of said at least partially reversible stress condition in said chlorophyll-containing matter caused by exposure of said chlorophyll-containing matter to a stress inducing environmental condition,
(f) comparing means which compares measured changes in the value of said parameter with said threshold value, and
(g) detection means adapted to detect an increase in the change of said parameter above said threshold value.

44. The apparatus of claim 43, further comprising a controller for controlling the intensity of said light source.

45. The apparatus of claim 44, wherein said controller is arranged to expose said chlorophyll-containing matter to a predetermined level of photon flux successively at predetermined intervals of time and said measuring means is arranged to measure said parameter based on the detected fluorescence signal emitted in response to each successive exposure to said predetermined level of photon flux.

46. The apparatus of claim 44, wherein said controller is arranged to successively activate said light source to cause chlorophyll in said matter to fluoresce and after each activation to reduce the intensity of said light source.

47. The apparatus of claim 43, comprising a controller arranged to control said light source to emit a predetermined integrated photon flux by causing said light source to emit a predefined series of light pulses, said integrated photon flux being the integrated photon flux of said series of light pulses.

48. The apparatus of claim 47, further comprising means for measuring a parameter based on the intensity of said fluorescence signal emitted in response to said series of light pulses.

49. The apparatus of claim 48, wherein said measuring means is arranged to measure the intensity of the fluorescent signal emitted in response to each of a plurality of said pulses within said senes.

50. The apparatus of claim 49, further comprising means arranged to calculate a value of fluorescence intensity based on said plurality of fluorescence intensities.

51. The apparatus of claim 50, wherein said calculating means is arranged to calculate said fluorescence intensity based on the average value of the fluorescence intensity from said plurality of intensity measurements.

52. The apparatus of claim 51, wherein said controller is arranged to expose said chlorophyll to a plurality of different levels of integrated photon flux within the range of about 0.001 to 20 $\mu mol/m^2/s$.

53. The apparatus of claim 47, further comprising means for measuring the fluorescence intensity after one or more of said light pulses in a series of light pulses, when the intensity of light from said light source is substantially zero.

54. The apparatus of claim 53, comprising means for subtracting the value of a fluorescence intensity measured after a light pulse from the value of a fluorescence intensity measured during a light pulse.

55. The apparatus of claim 54, wherein said predetermined level of change is determined from a plurality of measured fluorescence intensities.

56. The apparatus of claim 43, comprising a controller for exposing said chlorophyll-containing matter sequentially to a plurality of different light levels.

57. The apparatus of claim 56, wherein said controller is arranged to expose said chlorophyll-containing matter sequentially to at least three different light levels.

58. The apparatus of claim 56, comprising measuring means arranged to measure the intensity of the fluorescence signal at each of said plurality of different light levels, and means for deriving said parameter based on said plurality of fluorescence signal intensity measurements.

59. The apparatus of claim 58, wherein said parameter is based on the relationship between at least three measured fluorescence intensities, each measured at a different light level.

60. The apparatus of claim 59, wherein said parameter is a descriptor of said relationship.

61. The apparatus of claim 60, wherein said parameter is a fluorescence intensity based on a plurality of measured fluorescence intensities.

62. The apparatus of claim 61, wherein said parameter is the fluorescence intensity, $F\alpha$ at a level of light exposure of said chlorophyll-containing matter to zero photon flux.

63. The apparatus of claim 59, further comprising means for fitting a mathematical expression to a plurality of measured fluorescence intensities, and wherein said parameter comprises a descriptor of said mathematical expression.

64. The apparatus of claim 63, wherein said mathematical expression compnses a polynomial regression.

65. The apparatus of claim 64, wherein said polynomial regression comprises a second order polynomial regression.

66. The apparatus of claim 64, wherein said parameter comprises the value of a constant which qualifies a term of said polynomial regression.

67. The apparatus of claim 59, wherein each of said at least three different light levels to which said chlorophyll-containing matter is exposed is below that required to stimulate a maximal fluorescence signal in said chlorophyll containing matter.

68. The apparatus of claim 43, comprising a controller arranged to irradiate said matter sequentially with light at a plurality of different levels of photon flux, wherein said controller is arranged to generate each level of photon flux by generating a predefined series of light pulses, each light level being the integrated photon flux of each series of pulses.

69. The apparatus of claim 68, wherein said controller is arranged to generate each different light level by changing a parameter defining said series of pulses.

70. The apparatus of claim 69, wherein said controller is arranged to change the integrated photon flux to which said matter is exposed by changing at least one of the pulse frequency, the pulse width, the intensity of the pulses, and the time over which said series of pulses extends.

71. The apparatus of claim 69, wherein said measuring means is arranged to measure the intensity of the fluorescence signal emitted in response to each of a plurality of said pulses within a series.

72. The apparatus of claim 71, said apparatus comprising means for calculating the average value of the fluorescence intensity from said plurality of intensity measurements.

73. The apparatus of claim 72, said apparatus further comprising means for calculating the average fluorescence intensity at each of a plurality of different values of integrated of photon flux.

74. The apparatus of claim 73, comprising means for deriving said parameter from said plurality of calculated average fluorescence intensities.

75. The apparatus of claim 43, further comprising a monitor for monitoring a parameter affecting the health of said chlorophyll-containing matter.

76. The apparatus of claim 43, further comprising recording means for recording the value of said parameter affecting the health of said chlorophyll-containing matter when said change in said parameter exceeds said predetermined level.

77. The apparatus of claim 43, further comprising means for controlling the value of a parameter affecting the health of said chlorophyll-containing matter.

78. The apparatus of claim 43, further comprising a controller for controlling the value of said parameter affecting the health of said chlorophyll-containing matter in response to a change in said measured parameter above said predetermined level.

79. An apparatus as claimed in claim 43, further comprising:
a controller arranged to expose said chlorophyll-containing matter sequentially to at least three different light levels to cause said chlorophyll-containing matter to fluoresce and emit a fluorescent signal at each light level, said at least three different light levels each being below that required to stimulate a maximal fluorescence signal in said chlorophyll-containing matter,
said measuring means being arranged to measure the intensity of the fluorescent signal emitted from said chlorophyll-containing matter at each of said different light levels, and
determining means arranged to determine a relationship between said measured fluorescence intensities as a function of a parameter indicative of light level to which said chlorophyll-containing matter is exposed, and to provide, as said value of said parameter based on the detected fluorescent signal, the value of a parameter based on said determined relationship.

80. The apparatus of claim 79, wherein said parameter is a descriptor of said relationship.

81. The apparatus of claim 79, wherein said descriptor comprises any one of the fluorescence intensity, $f\alpha$, at a level of light exposure of said chlorophyll-containing matter to zero photon flux, and the value of a coefficient of a term of a polynomial regression describing the relationship between said measured intensities.

82. The apparatus of claim 43, wherein said light comprises red light.

83. The apparatus of claim 43, wherein said change in said parameter above said predetermined level of change occurs with an increase in the intensity of the detected fluorescence signal.

84. A method of detecting the recovery from an at least partially reversible stress condition in chlorophyll-containing matter, the method comprising:
 (a) providing chlorophyll-containing matter exposed to a stress affecting environmental condition,
 (b) exposing the matter to light to cause chlorophyll in the matter to fluoresce and emit a fluorescence signal,
 (c) detecting the emitted fluorescence signal,
 (d) measuring the value of a parameter based on the detected fluorescence signal,
 (e) monitoring the value of said parameter,
 (f) detecting changes in the value of said parameter,
 (g) providing a threshold value of a predetermined level of change in said parameter which only if reached and exceeded signifies the recovery from said at least partially reversible stress condition in the chlorophyll-containing matter caused by said stress affecting environmental condition, and
 (h) comparing changes in the value of said parameter with said threshold value, wherein a determination that the value of said parameter reaches and exceeds said threshold value signifies recovery from said at least partially reversible stress condition in the chlorophyll-containing matter caused by said stress affecting environmental condition.

85. An apparatus for detecting the recovery from an at least partially reversible stress condition in chlorophyll-containing matter comprising:
 (a) a light source for causing chlorophyll in chlorophyll-containing matter to fluoresce and emit a fluorescence signal,
 (b) a detector for detecting the fluorescence signal,
 (c) measuring means for measuring the value of a parameter based on the detected fluorescence signal,
 (d) monitoring means for monitoring changes in the value of said parameter,
 (e) a device storing a threshold value of a predetermined level of change in said parameter, which only if reached and exceeded signifies the recovery from said at least partially reversible stress condition in said chlorophyll-containing matter caused by exposure of said chlorophyll-containing matter to a stress affecting environmental condition,
 (f) comparing means which compares changes in the value of said parameter with said threshold value, and
 (g) detection means adapted to detect an increase in the change of said parameter above said threshold value.

* * * * *